United States Patent [19]

Ok et al.

[11] Patent Number: 5,208,228

[45] Date of Patent: May 4, 1993

[54] AMINOMACROLIDES AND DERIVATIVES HAVING IMMUNOSUPPRESSIVE ACTIVITY

[75] Inventors: Hyun O. Ok, Edison; Thomas R. Beattie, Scotch Plains; Michael H. Fisher, Ringoes; Matthew J. Wyvratt, Mountainside; Mark Goulet, Westfield, all of N.J.

[73] Assignee: Merck & Co., Inc., Rahway, N.J.

[21] Appl. No.: 698,888

[22] Filed: May 13, 1991

Related U.S. Application Data

[63] Continuation-in-part of Ser. No. 598,440, Oct. 22, 1990, abandoned, which is a continuation-in-part of Ser. No. 434,158, Nov. 13, 1989, abandoned.

[51] Int. Cl.$^5$ .................. A61K 31/33; A61K 31/535; A61K 31/44; C07D 498/12
[52] U.S. Cl. .................. 514/183; 514/230.5; 514/291; 514/294; 540/455; 540/456; 544/105
[58] Field of Search .................. 540/455, 456, 457; 514/183, 230.5, 294, 291; 544/105

[56] References Cited

U.S. PATENT DOCUMENTS

| 4,650,803 | 3/1987 | Stella et al. | 514/291 |
|---|---|---|---|
| 4,894,366 | 1/1990 | Okuhara et al. | 514/63 |
| 4,916,138 | 4/1990 | Ueda et al. | 514/294 |
| 4,929,611 | 5/1990 | Okuhara et al. | 514/183 |
| 4,956,352 | 9/1990 | Okuhara et al. | 514/63 |
| 4,981,792 | 1/1991 | Inamine et al. | 435/119 |
| 4,987,139 | 1/1991 | Chen et al. | 514/321 |
| 5,064,835 | 11/1991 | Bochis et al. | 514/291 |

FOREIGN PATENT DOCUMENTS

| 0315978 | 5/1989 | European Pat. Off. |
| 0323042 | 7/1989 | European Pat. Off. |
| 0349061 | 1/1990 | European Pat. Off. |
| 0353678 | 2/1990 | European Pat. Off. |
| 0356399 | 2/1990 | European Pat. Off. |
| 0369344 | 5/1990 | European Pat. Off. |
| 0388152 | 9/1990 | European Pat. Off. |
| 0388153 | 9/1990 | European Pat. Off. |
| 0427680 | 5/1991 | European Pat. Off. |
| 0428169 | 5/1991 | European Pat. Off. |
| 0428365 | 5/1991 | European Pat. Off. |
| WO89/05304 | 6/1989 | World Int. Prop. O. |
| WO90/14826 | 12/1990 | World Int. Prop. O. |
| WO91/02736 | 3/1991 | World Int. Prop. O. |
| WO91/04025 | 4/1991 | World Int. Prop. O. |
| WO91/13889 | 9/1991 | World Int. Prop. O. |

OTHER PUBLICATIONS

Tanaka, et al., *J. Am. Chem. Soc.*, 1987, 109, 5031–5033.
Bierer, et al., *Science*, 1990, 250, 556–559.
Donald, et al., *Tetrahedron Lett.*, 1991, 32, 1375–1378.
C. Arita, et al., *Clin. Exp. Immunol*, 1990, 82, 456–461.
N. Murase, et al., *Diabetes*, 1990, 39, 1584–1586.
J. McCauley, et al., *Lancet*, 1990, 335, 674.
K. Takabayashi, et al., *Clin. Immunol. Immunopathol.*, 1989, 51, 110–117.
U.S. Ser. No. 486,700 Bochis, et al. Mar. 1, 1990.
U.S. Ser. No. 516,598 Goulet, et al. Apr. 30, 1990.
U.S. Ser. No. 551,811 Beattie, et al. Jun. 25, 1990.
U.S. Ser. No. 596,177 Bochis, et al. Oct. 11, 1990.
U.S. Ser. No. 598,440 Ok, et al. Oct. 22, 1990.
U.S. Ser. No. 687,366 Goulet Apr. 18, 1991.
U.S. Ser. No. 698,886 Goulet, et al. May 13, 1991.
U.S. Ser. No. 698,889 Sinclair, et al. May 13, 1991.
U.S. Ser. No. 699,407 Goulet, et al. May 13, 1991.

*Primary Examiner*—Cecilia Tsang
*Attorney, Agent, or Firm*—Charles M. Caruso; J. Eric Thies

[57] ABSTRACT

Aminomacrolides of the general structural Formula I:

(Abstract continued on next page.)

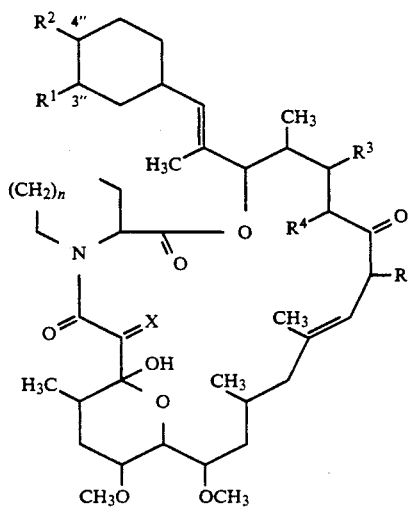

27 Claims, No Drawings have been prepared from suitable precursors by incorporation of a nitrogen substituent at C-3" and/or C-4" of the cyclohexyl ring. These macrolide immunosuppressants are useful in a mammalian host for the treatment of autoimmune diseases, infectious diseases and/or the prevention of rejection of foreign organ transplants. In addition, these macrolide immunosuppressants are useful in the topical treatment of inflammatory and hyperproliferative skin diseases and cutaneous manifestations of immunologically-mediated illnesses. Also, these macrolides are useful in the treatment of reversible obstructive airways disease, particularly asthma.

AMINOMACROLIDES AND DERIVATIVES HAVING IMMUNOSUPPRESSIVE ACTIVITY

This application is a continuation-in-part of copending application Ser. No. 598,440, filed Oct. 22, 1990, now abandoned which is in turn a continuation-in-part of copending application Ser. No. 434,158, filed Nov. 13, 1989, now abandoned.

SUMMARY OF THE INVENTION

The present invention is related to compounds which are useful in a mammalian host for the treatment of autoimmune diseases (such as juvenile-onset or recent-onset diabetes mellitus, multiple sclerosis, rheumatoid arthritis, liver disease, posterior uveitis, allergic encephalomyelitis, and glomerulonephritis), infectious diseases, the prevention of rejection of foreign organ transplants, e.g. bone marrow, kidney, liver, heart, skin, small-bowel, and pancreatic-islet-cell transplants, the topical treatment of inflammatory and hyperproliferative skin diseases, cutaneous manifestations of immunologically-mediated illnesses (such as psoriasis, atopical dermatitiis, contact dermatitis and further eczematous dermatitises, seborrhoeic dermatitis, Lichen planus, Pemphigus, bullous Pemphigoid, *Epidermolysis bullosa*, urticaria, angioedemas, vasculitides, erythemas, cutaneous eosinophilias, *Lupus erythematosus* or *Alopecia areata*), reversible obstructive airways disease, particularly asthma, and/or hepatic injury associated with ischemia. In addition, some of the compounds of this invention have antagonistic properties and so may have utility in the reversal of immunosuppressive activity and/or diminishing the toxicity of other immunosuppressive agents.

More particularly, this invention relates to compounds of the general structural Formula I:

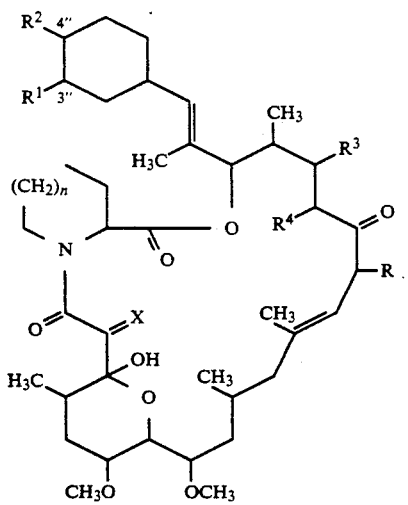

wherein R, $R^1$, $R^2$, $R^3$, $R^4$, X, and n are hereinafter defined.

This invention also relates to pharmaceutical compositions containing the compounds and to a method of use of the present compounds and other agents for the treatment of autoimmune diseases, infectious diseases, the rejection of foreign organ transplants, inflammatory and hyperproliferative skin diseases, cutaneous manifestations of immunologically-mediated illnesses, and/or reversible obstructive airways diesase, and further for modifying the activity and/or toxicity of other immunosuppressive agents.

BRIEF DESCRIPTION OF DISCLOSURES IN THE ART

Fujisawa United States, European and Japanese patents and applications (U.S. Pat. No. 4,894,366, issued Jan. 16, 1990, EPO Publication No. 0,184,162 and PBJ Disclosure 63-17884) and publications (*J. Am. Chem. Soc.*, 1987, 109, 5031 and *J. Antibiotics* 1987, 40, 1249) disclose 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (FR-900506, FK-506 L-679,934), 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (FR-900520) and related compounds which are the starting materials for the preparation of the compounds described. The synthetic preparation of the aforementioned starting material (FR-900506) has recently been reported (*J. Am. Chem Soc.*, 1989, 111, 1157). A Sandoz European patent application (EPO Publication No. 0,356,399) discloses stereoisomers of FR-900506 and derivatives at the 17-position. Fisons European and WIPO patent applications (EPO Publication No. 0,323,042 and PCT Publication No. WO89/05304) disclose various derivatives of FR-900506, FR-900520 and related compounds.

Fujisawa United States patents (U.S. Pat. No. 4,929,611, issued May 29, 1990 and U.S. Pat. No. 4,956,352, issued Sep. 11, 1991) disclose the use of FK-506-type compounds in treating resistance to transplantation. A Sandoz European patent application (EPO Publication No. 0,315,978) discloses the use of FR-900506 and related compounds in the topical treatment of inflammatory and hyperproliferative skin diseases and of cutaneous manifestations of immunologically-mediated illness. A Fisons WIPO patent application (PCT Publication WO 90/14826) discloses the use of FR-900506 and related compounds in the treatment of reversible obstructive airways disease, particularly asthma. Various studies have suggested the efficacy of FK-506 in the treatment of a number of ailments, including rheumatoid arthritis (C. Arita, et al., *Clincial exp. Immunol.*, 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al., *Lancet*, 1990, 336, 373–74), posterior uveitis (H. Kawashima, *Invest. Ophthalmol. Vis. Sci.*, 1988, 29, 1265–71), hepatic injury associated with ischemia (M. Sakr, et al., *Life Sci.*, 1990, 47, 687–91) allergic encephalomyelitis (K, Deguchi, et al., *Brain Nerve*, 1990, 42, 391–97), glomeralonephritis (J. McCauley, et al., *Lancet*, 1990, 335, 674) and systemic lupus erythematosus (K. Takabayashi, et al., *Clin. Immunol. Immunopathol.*, 1989, 51, 110–117).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Chrons disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAIDs and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was licensed by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, FR-900506, FK-506,

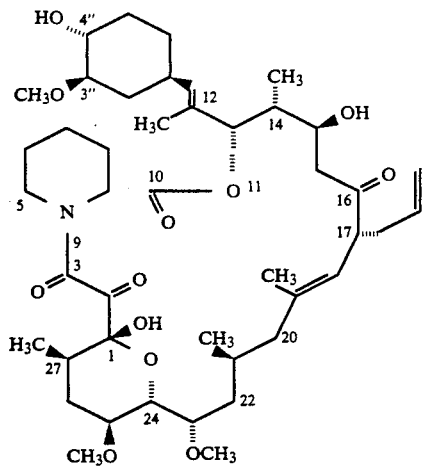

and related compounds which were isolated and characterized by Tanaka, Kuroda, and co-workers at Fujisawa Pharmaceutical Co. in Japan, see *J. Am. Chem. Soc.*, 1987, 109, 5031, and U.S. Pat. No. 4,894,366, issued Jan. 16, 1990) have been shown to possess exceptional immunosuppressive activity. A Fujisawa United States patents (U.S. Pat. No. 4,929,611, issued May 29, 1990 and U.S. Pat. No. 4,956,352, issued Sep. 11, 1990) disclose the use of FK-506-type compounds in treating resistance to transplantation. In particular, the compound FR-900506 has been reported to be 100 times more effective than cyclosporin in the supression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), rheumatoid arthritis (C. Arita, et al., *Clincial exp. Immunol.*, 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al., *Lancet*, 1990, 336, 373–74), posterior uveitis (H. Kawashima, *Invest. Ophthalmol. Vis. Sci.*, 1988, 29, 1265–71), hepatic injury associated with ischemia (M. Sakr, et al., *Life Sci.*, 1990, 47, 687–91) allergic encephalomyelitis (K, Deguchi, et al., *Brain Nerve*, 1990, 42, 391–97), glomerulonephritis (J. McCauley, et al., *Lancet*, 1990, 335, 674) and systemic lupus erythematosus (K. Takabayashi, et al., *Clin. Immunol. Immunopathol.*, 1989, 51, 110–117).

Accordingly, an object of the present invention is to provide new analogs of these tricyclomacrolides which will (1) restore the balance of the help-and-suppression mechanism of the immune system by acting at an earlier point than the anti-inflammatory agents and (2) induce specific long-term transplantation tolerance through a suppressor cell circuit without increasing the body's susceptibility to infection.

An additional object of the present invention is to provide new analogs of these tricyclomacrolide immunosuppressants which have antagonistic properties. These analogs would find utility in the reversal of the immunosuppressive activity of other immunosuppressive agents and so provide antidotes for overdoses of the immunosuppressants. These analogs would further find utility in diminishing the toxicity of other immunosuppressive agents allowing higher dosages of such agents while minimizing their toxic effects.

Another object of the present invention is to provide analogs of these tricyclo-macrolides which posses topical activity in the treatment of inflammatory and hyperproliferative skin diseases and cutaneous manifestations of immunologically-mediated illnesses.

An additional object of the present invention is to provide pharmaceutical compositions for administering to a patient in need of the treatment one or more of the active immunosuppressive agents of the present invention.

Still a further object of this invention is to provide a method of controlling graft rejection, autoimmune and chronic inflammatory dieases by administering a sufficient amount of one or more of the novel immunosuppressive agents in a mammalian species in need of such treatment.

Finally, it is the object of this invention to provide processes for the preparation of the active compounds of the present invention.

DETAILED DESCRIPTION OF THE INVENTION

A. Scope of the Invention

The novel compound of this invention has structural Formula I:

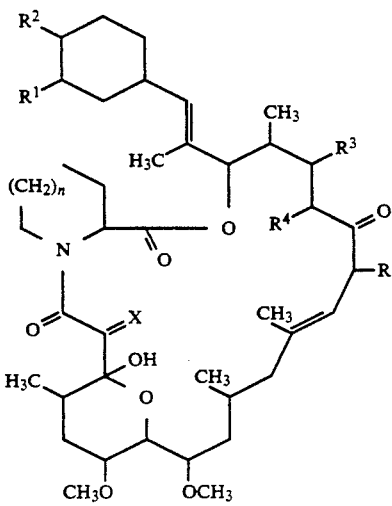

or a pharmaceutically acceptable salt thereof, wherein:

R is
1) methyl,
2) ethyl,
3) propyl, or
4) allyl;

$R^1$ and $R^2$ are, independently,
1) —$N_3$;
2) —NHCN;
3) —$NR^5R^6$, wherein $R^5$ and $R^6$ are independently,
   a) hydrogen,
   b) $C_1$-$C_{12}$ alkyl, unsubstituted or substituted with $R^7$ and $R^8$, wherein $R^7$ and $R^8$ are independently selected from the group consisting of:
      i) hydrogen,
      ii) —OH,
      iii) $C_1$-$C_6$ alkoxy,
      iv) —O—CO—$C_1$-$C_6$ alkyl,
      v) —$NR^9R^{10}$, wherein $R^9$ and $R^{10}$ are independently, hydrogen, or $C_1$-$C_6$ alkyl, unsubstituted or substituted with phenyl
      vi) —$CONR^9R^{10}$,
      vii) —$CO_2H$,
      viii) —CO—O—$C_1$-$C_6$ alkyl,
      ix) —S—$C_1$-$C_6$ alkyl,
      x) —SO—$C_1$-$C_6$ alkyl,
      xi) —$SO_2$—$C_1$-$C_6$ alkyl,
      xii) halo, such as Cl, Br, F or I,
      xiii) $C_3$-$C_7$-cycloalkyl,
      xiv) phenyl, unsubstituted or substituted with M, W and Y, wherein M, W and Y are independently selected from the group consisting of:
         A) hydrogen,
         B) $C_1$-$C_6$ alkyl,
         C) —OH,
         D) $C_1$-$C_6$ alkoxy,
         E) —O—CO—$C_1$-$C_6$ alkyl,
         F) —$NR^9R^{10}$, wherein $R^9$ and $R^{10}$ are as defined above,
         G) —$CONR^9R^{10}$,
         H) —$CO_2H$,
         I) —CO—O—$C_1$-$C_6$ alkyl,
         J) halo, such as Cl, Br, F or I,
         K) —$NO_2$,
         L) —CN, and
         N) —$CF_3$,
      xv) naphthyl, unsubstituted or substituted with M, W and Y, wherein M, W and Y are as defined above, and
      xvi) —$CF_3$,
   c) $C_3$-$C_{12}$ alkenyl, unsubstituted or substituted with $R^7$ and $R^8$, wherein $R^7$ and $R^8$ are as defined above,
   d) $C_3$-$C_7$ cycloalkyl, unsubstituted or substituted with $R^7$ and $R^8$, wherein $R^7$ and $R^8$ are as defined above,
   e) phenyl, unsubstituted or substituted with M, W and Y, wherein M, W and Y are as defined above,
   f) naphthyl, unsubstituted or substituted with M, W and Y, wherein M, W and Y are as defined above,
   g) —$SO_2$—phenyl, wherein phenyl is unsubstituted or substituted with with M, W and Y, wherein M, W and Y are as defined above,
   h) —$SO_2$—$C_1$-$C_6$ alkyl,
   i) or where $R^5$ and $R^6$ and the N to which they are attached may form an unsubstituted or substituted 3- to 7-membered heterocyclic ring which may include one or two additional heteroatoms independently selected from the group consisting of O, S, or $NR^9$, wherein $R^9$ is as defined above, such as morpholine, thiomorpholine, piperidine, piperizine, and where the substituent(s), attached to the carbon atom(s) in the heterocyclic ring is/are independently selected form the group consisting of:
      i) hydrogen,
      ii) —OH,
      iii) $C_1$-$C_6$ alkoxy,
      iv) —O—CO—$C_1$-$C_6$ alkyl,
      v) —$NR^9R^{10}$, wherein $R^9$ and $R^{10}$ are independently, hydrogen, or $C_1$-$C_6$ alkyl, unsubstituted or substituted with phenyl,
      vi) —$CONR^9R^{10}$,
      vii) —$CO_2H$,
      viii) —CO—O—$C_1$-$C_6$ alkyl,
      ix) —SH,
      x) halo, such as Cl, Br, F or I,
      xi) phenyl, unsubstituted or substituted with M, W and Y, wherein M, W and Y are as defined above,
      xii) naphthyl, unsubstituted or substituted with M, W and Y, wherein M, W and Y are as defined above, and
      xiii) —$CF_3$;
4) —$N(R^5)CO$—O—$R^{11}$, wherein $R^5$ is as defined above and $R^{11}$ is $C_1$-$C_{12}$ alkyl, unsubstituted or substituted with $R^7$ and $R^8$, wherein $R^7$ and $R^8$ are as defined above;
5) —$N(R^5)CO$—$R^{12}$, wherein $R^5$ is as defined above and $R^{12}$ is
   a) hydrogen,
   b) $C_1$-$C_{12}$ alkyl, unsubstituted or substituted with $R^7$ and $R^8$, wherein $R^7$ and $R^8$ are as defined above,
   c) $C_3$-$C_{12}$ cycloalkyl, unsubstituted or substituted with $R^7$ and $R^8$, wherein $R^7$ and $R^8$ are as defined above, d) phenyl, unsubstituted or substituted with M, W and Y, wherein M, W and Y are as defined above, e) naphthyl, unsubstituted or substituted with M, W and Y, wherein M, W and Y are as defined above, or f) where $R^5$ and $R^{12}$ and the —NCO— to which they are attached may form an unsubstituted or substituted 5- to 7-membered heterocyclic ring which may include one or two additional heteroatoms independently selected from the group consisting of O, S, or $NR^9$, wherein $R^9$ is as defined above, such as pyrrolidone, or piperidinone;

6) —N($R^{13}$)COCH($R^{17}$)$NR^5R^6$ wherein $R^5$ and $R^6$ are as defined above, $R^{13}$ is selected from the definitions of $R^5$, and $R^{17}$ is a) hydrogen, b) $C_1$-$C_4$ alkyl, unsubstituted or substituted with $R^{18}$, wherein $R^{18}$ is selected from the group consisting of:
i) —OH,
ii) $C_1$-$C_6$ alkoxy,
iii) —O—CO—$C_1$-$C_6$ alkyl,
iv) —SH,
v) —S—$C_1$-$C_6$ alkyl,
vi) —$NR^9R^{10}$, wherein $R^9$ and $R^{10}$ are as defined above,
vii) —$CO_2H$,
viii) —$CONH_2$,
ix) imidazolyl,
x) indolyl,
xi) phenyl, and
xii) p-hydroxyphenyl, or c) phenyl;

7) —N($R^{13}$)CO($CH_2$)$_m$$NR^5R^6$, wherein m is 0 or 2–6, $R^5$ and $R^6$ are as defined above, and $R^{13}$ is selected from the definitions of $R^5$, or where $R^{13}$ and $R^5$ and the —NCO($CH_2$)$_m$N— to which they are attached may form an unsubstituted or substituted 5- to 7-membered heterocyclic ring, such as 2-imidazolidone;

8) —N=C($R^{13}$)—$NR^5R^6$, wherein $R^5$ and $R^6$ are as defined above, and $R^{13}$ is selected from the definitions of $R^5$, and wherein if either $R^5$ or $R^6$ are hydrogen, the tautomeric structure —NHC($R^{13}$)=$NR^{5\ or\ 6}$ is also possible;

9) —N($R^{14}$)$_3^+$$A^-$, wherein $R^{14}$ is $C_1$-$C_6$ alkyl, unsubstituted or substituted with phenyl or naphthyl, and wherein $A^-$ is a counterion;

10)

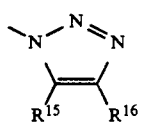

wherein $R^{15}$ and $R^{16}$ are independently,
a) hydrogen,
b) phenyl, unsubstituted or substituted with M, W and Y, wherein M, W and Y are as defined above;
c) naphthyl, unsubstituted or substituted with M, W and Y, wherein M, W and Y are as defined above,
d) —CN,
e) —$CF_3$,
f) —CO—$C_1$-$C_6$ alkyl, or
g) —CO—O—$C_1$-$C_6$ alkyl;

11) hydroxy or $C_1$-$C_6$ alkoxy, with the proviso that $R^1$ and $R^2$ are not simultaneously hydroxy, $C_1$-$C_6$ alkoxy, or combinations thereof; or 12) where $R^1$ and $R^2$ may both be connected to form a 3- to 7-membered heterocyclic ring of the form:

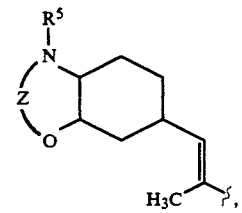

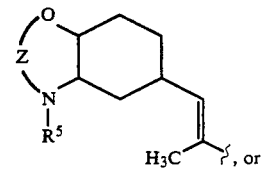

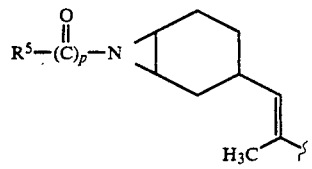

wherein p is zero or one, $R^5$ is as defined above, and Z is
a) —CO—,
b) —CS—,
c) —CO—$C_1$-alkyl,
d) —CS—$C_1$-alkyl, or
e) $C_1$-$C_2$-alkyl, wherein the alkyl may be unsubstituted or substituted with one or more of the following:
i) —OH,
ii) $C_1$-$C_6$ alkyl,
iii) $C_1$-$C_6$ alkoxy,
iv) —O—CO—$C_1$-$C_6$ alkyl,
v) —$NR^9R^{10}$, wherein $R^9$ and $R^{10}$ are as defined above,
vi) —$CONR^9R^{10}$,
vii) —$CO_2H$,
viii) —CO—O—$C_1$-$C_6$ alkyl,
ix) —S—$C_1$-$C_6$ alkyl,
x) —SO—$C_1$-$C_6$ alkyl,
xi) —$SO_2$—$C_1$-$C_6$ alkyl,
xii) halo, such as Cl, Br, F or I
xiii) phenyl, unsubstituted or substituted with M, W and Y, wherein M, W and Y are as defined above, or
xiv) naphthyl unsubstituted or substituted with M, W and Y, wherein M, W and Y are as defined above;

$R^3$ is hydrogen, hydroxy, or $C_1$-$C_6$ alkoxyl;

$R^4$ is hydrogen, or $R^3$ and $R^4$ taken together form a double bond;

X is O or (H,OH); and n is 1 or 2.

The compounds of the present invention have asymmetric centers and this invention includes all of the optical isomers and mixtures thereof.

In addition compounds with carbon-carbon double bonds may occur in Z- and E-forms with all isomeric forms of the compounds being included in the present invention.

When any variable (e.g., alkyl, aryl, $R^5$, $R^6$, $R^7$, $R^8$, $R^9$, $R^{10}$, $R^{11}$, $R^{12}$, $R^{13}$, etc.) occurs more than one time in any variable or in Formula I, its definition on each occurrence is independent of its definition at every other occurrence.

As used herein, "alkyl" is intended to include both branched- and straight-chain saturated aliphatic hydrocarbon groups having the specified number of carbon atoms, representative examples being methyl, ethyl, isopropyl, tert-butyl, and sec-butyl; "alkoxy" represents an alkyl group of indicated number of carbon atoms attached through an oxygen bridge; and "$C_3$-$C_7$-cycloalkyl" is intended to include saturated ring groups, such as cyclopropyl, cyclobutyl, cyclopentyl, cyclohexyl and cycloheptyl. "Alkanoyl" is intended to include those alkylcarbonyl groups of specified number of carbon atoms, which are exemplified by formyl, acetyl, propanoyl and butanoyl; "alkenyl" is intended to include hydrocarbon chains of either a straight- or branched-configuration and one unsaturation, which may occur at any point along the chain, such as ethenyl, propenyl, butenyl, pentenyl, and the like, and includes E and Z forms, where applicable; and "arylalkyl" represents aryl groups as herein defined which are attached through a straight- or branched-chain alkyl group of specified number of carbon atoms, such as, for example, benzyl, phenethyl, 3,3-diphenylpropyl, 3-indolylmethyl, and the like. "Halo", as used herein, means fluoro, chloro, bromo and iodo, and "counterion" is used to represent a small negatively-charged species, such as chloride, bromide, iodide, hydroxide, nitrate, acetate, citrate, benzoate, perchlorate, benzene sulfonate, tartrate, hemitartrate, maleate, and the like.

The aliphatic acyl may include lower alkanoyl (of one to six carbon atoms) which may have one or more suitable substituent(s) (e.g. formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.), cyclo(lower)alkyloxy(lower)alkanoyl which may have one or more suitable substituent(s) such as lower alkyl (e.g. cyclopropyloxyacetyl, cyclobutyloxypropionyl, cycloheptyloxybutyryl, methyloxyacetyl, methyloxypropionyl, methyloxybutyryl, methyloxyheptanoyl, methyloxyhexanoyl, etc.), and the like.

The aromatic acyl may include aroyl and substituted aroyl. Examples of aromatic acyl include benzoyl, toluoyl, xyloyl, naphthoyl, nitrobenzoyl, dinitrobenzoyl, nitronaphthoyl, etc.

The aliphatic acyl substituted with aromatic group may include aryl(lower)alkanoyl which may have one or more suitable substitutent(s) such as lower alkoxy and trihalo(lower)alkyl (e.g. phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.), and the like.

The aryl or aromatic group may include phenyl or naphthyl which is optionally-substituted by from one- to three-members independently selected from the group consisting of amino, $C_1$-$C_4$ alkoxy, $CO_2$-$C_1$-$C_4$-alkyl, $CO_2H$, $C_1$-$C_7$ alkyl, cyano, halo, hydroxy, nitro, thio and trifluoromethyl.

In the present invention it is preferred that in compounds of Formula I:

R is
1) ethyl,
2) propyl, or
3) allyl;

$R^1$ and $R^2$ are, independently,
1) —$N_3$;
2) —$NR^5R^6$, wherein $R^5$ and $R^6$ are independently,
   a) hydrogen,
   b) $C_1$-$C_{12}$ alkyl, unsubstituted or substituted with $R^7$ and $R^8$, wherein $R^7$ and $R^8$ are independently selected from the group consisting of:
      i) hydrogen,
      ii) —OH,
      iii) $C_1$-$C_6$alkoxy,
      iv) —O—CO—$C_1$-$C_6$alkyl,
      v) —$NR^9R^{10}$, wherein $R^9$ and $R^{10}$ are independently, hydrogen, or $C_1$-$C_6$alkyl, unsubstituted or substituted with phenyl,
      vi) —$CONR^9R^{10}$,
      vii) —CO—O—$C_1$-$C_6$alkyl,
      viii) halo, such as Cl, Br, F or I,
      xiv) phenyl, unsubstituted or substituted with M, W and Y, wherein M, W and Y are independently selected from the group consisting of:
         A) hydrogen,
         B) $C_1$-$C_6$alkyl,
         C) —OH,
         D) $C_1$-$C_6$alkoxy,
         E) —O—CO—$C_1$-$C_6$alkyl,
         F) —$NR^9R^{10}$, wherein $R^9$ and $R^{10}$ are as defined above,
         G) —$CONR^9R^{10}$,
         H) —$CO_2H$,
         I) —CO—O—$C_1$—$C_6$ alkyl,
         J) halo, such as Cl, Br, F or I,
         K) —$NO_2$,
         L) —CN, and
         N) —$CF_3$,
      xv) naphthyl, unsubstituted or substituted with M, W and Y, wherein M, W and Y are as defined above, and
      xi) —$CF_3$,
   c) $C_3$-$C_{12}$ alkenyl, unsubstituted or substituted with $R^7$ and $R^8$, wherein $R^7$ and $R^8$ are as defined above,
   d) $C_3$-$C_7$ cycloalkyl, unsubstituted or substituted with $R^7$ and $R^8$, wherein $R^7$ and $R^8$ are as defined above,
   e) phenyl, unsubstituted or substituted with M, W and Y, wherein M, W and Y are as defined above,
   f) naphthyl, unsubstituted or substituted with M, W and Y, wherein M, W and Y are as defined above,
   g) —$SO_2$-phenyl, wherein phenyl is unsubstituted or substituted with with M, W and Y, wherein M, W and Y are as defined above,
   h) —$SO_2$—$C_1$—$C_6$ alkyl;
3) —$N(R^5)CO$—O—$R^{11}$, wherein $R^5$ is as defined above and $R^{11}$ is $C_1$-$C_{12}$ alkyl, unsubstituted or substituted with $R^7$ and $R^8$, wherein $R^7$ and $R^8$ are as defined above;
4) —$N(R^5)CO$—$R^{12}$, wherein $R^5$ is as defined above and $R^{12}$ is a) hydrogen,
b) $C_1$-$C_{12}$ alkyl, unsubstituted or substituted with $R^7$ and $R^8$, wherein $R^7$ and $R^8$ are as defined above,
c) $C_3$-$C_{12}$ cycloalkyl, unsubstituted or substituted with $R^7$ and $R^8$, wherein $R^7$ and $R^8$ are as defined above,
d) phenyl, unsubstituted or substituted with M, W and Y, wherein M, W and Y are as defined above, or
e) naphthyl, unsubstituted or substituted with M, W and Y, wherein M, W and Y are as defined above;

5) —N($R^{13}$)COCH($R^{17}$)$NR^5R^6$ wherein $R^5$ and $R^6$ are as defined above, $R^{13}$ is selected from the definitions of $R^5$, and $R^{17}$ is
a) hydrogen,
b) $C_1$-$C_4$ alkyl, unsubstituted or substituted with $R^{18}$, wherein $R^{18}$, wherein $R^{18}$ is selected from the group consisting of:
  i) —OH
  ii) $C_1$-$C_6$ alkoxy,
  iii) —O—CO—$C_1$-$C_6$ alkyl,
  iv) —SH,
  v) —S—$C_1$-$C_6$ alkyl,
  vi) —$NR^9R^{10}$, wherein $R^9$ and $R^{10}$ are as defined above,
  vii) —$CO_2H$,
  viii) —$CONH_2$,
  ix) imidazolyl,
  x) indolyl,
  xi) phenyl, and
  xii) p-hydroxyphenyl, or
c) phenyl;

6) —N($R^{13}$)CO($CH_2$)$_m$$NR^5R^6$, wherein m is 0 or 2-6, $R^5$ and $R^6$ are as defined above, and $R^{13}$ is selected from the definitions of $R^5$;

7) —N=C($R^{13}$)—$NR^5R^6$, wherein $R^5$ and $R^6$ are as defined above, and $R^{13}$ is selected from the definitions of $R^5$, and wherein if either $R^5$ or $R^6$ are hydrogen, the tautomeric structure —NHC($R^{13}$)=N-$R^{5 or 6}$ is also possible;

8) —N($R^{14}$)$_3^+$$A^-$, wherein $R^{14}$ is $C_1$-$C_6$ alkyl, unsubstituted or substituted with phenyl or naphthyl, and wherein $A^-$ is a counterion;

9) 1-(1,2,3-triazolyl), substituted with $R^{15}$ and $R^{16}$, wherein $R^{15}$ and $R^{16}$ are
a) hydrogen,
b) phenyl, or
c) —CO—O—$C_1$-$C_6$ alkyl;

10) hydroxy or $C_1$-$C_6$ alkoxy, with the proviso that $R^1$ and $R^2$ are not simultaneously hydroxy, $C_1$-$C_6$ alkoxy, or combinations thereof; or 11) where $R^1$ and $R^2$ may both be connected to form a 3- to 7-membered heterocyclic ring of the form:

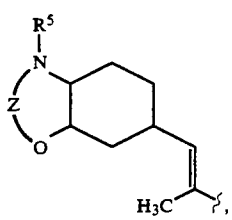

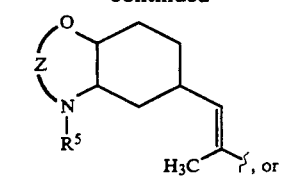

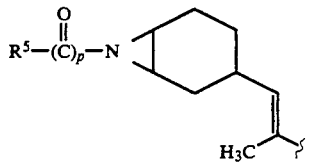

wherein p is one, $R^5$ is as defined above, and Z is
a) —CO—,
b) —CO—$C_1$-alkyl, or
c) $C_1$-$C_2$-alkyl;
$R^3$ is hydrogen or hydroxy;
$R^4$ is hydrogen;
X is O or (H, OH); and
n is 1 or 2;
or a pharmaceutically acceptable salt thereof.

In the present invention it is even more preferred that in compounds of Formula I:
R is ethyl, propyl or allyl;
$R^1$ and $R^2$ are, independently, $N_3$—; $H_2N$—; $CH_3NH$—; $(CH_3)_2N$—; $PhCH_2NH$—; $HOCH(CH_3)CH_2NH$—; $CH_2=CHCH_2NH$—; $^+(CH_3)_3N$—; $CH_3CONH$—; $CH_3COOCH_2CONH$—; $PhNHCONH$—; $HCONH$—; $CH_3CH_2OCONH$—; $CH_3OCONH$—; $PhCH_2OCONH$—; $HN=C(CH_3)NH$—; $HN=C(CH_2Ph)NH$—; $HN=CHNH$—; (N'-t-butoxycarbonyl-D-phenylalanine)amido; (N'-t-butoxycarbonyl-L-phenylalanine)amido; (D-phenylalanine)amido; (L-phenylalanine)amido; cyclopropylcarboxamido; adamantylcarboxamido; 1-(4,5-dicarboethoxy-1,2,3-triazole); or hydroxy or $C_1$-$C_6$ alkoxy, with the proviso that $R^1$ and $R^2$ are not simultaneously hydroxy, $C_1$-$C_6$ alkoxy, or combinations thereof;
$R^3$ is hydrogen or hydroxy;
$R^4$ is hydrogen;
X is O; and
n is 2;
or pharmaceutically acceptable salts thereof.

Preferred compounds of the present invention are the compounds identified as follows:
17-Ethyl-1,14-dihydroxy-12-[2'-(4"-azido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-1,14-dihydroxy-12-[2'-(4"-amino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-1,14-dihydroxy-12-[2'-(4"-acetylamino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-1,14-dihydroxy-12-[2'-(4"-N-(2-propenyl)amino-3"-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-N-methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-N-methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-1'''-adamantane carboxamido-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-cyclopropanecarboxamido-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-formamido-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-{2'-[4''-(4''',5'''-dicarboethoxy-1''',2''',3'''-triazole)-3''-methoxycyclohexyl]-1'-methylvinyl}-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-acetylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-amino-3''-hydroxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(3''-amino-4''-hydroxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-acetylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1-hydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1-hydroxy-12-[2'-(4''-acetylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-amino-3''-hydroxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-hydroxy-3''-aminocyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-beta-amino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-alpha-amino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-beta-amino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-alpha-amino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-amino-3''-isopropyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-amino-3''-isopropyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-amino-3''-n-propyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-amino-3''-n-propyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-amino-3''-ethoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-amino-3''-ethoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-methylcarbamate-3''-methoxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-1-hydroxy-12-[2'-(4''-benzylcarbamate-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-acetamidine-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-benzamidine-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-formamidine-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(L-phenyl alanyl)amido-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(L-phenyl alanyl)amido-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(D-phenyl alanyl)amido-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(D-phenyl alanyl)amido-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(amino acetylamino)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(aminoacetylamino)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(2-hydroxypropyl amino)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(2-hydroxypropyl amino)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(1-aza-4-oxabicyclo[4.4.0]dec-6-yl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(1-aza-4-oxabicyclo[4.4.0]dec-6-yl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-trimethylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone Iodide;

17-Allyl-1,14-dihydroxy-12-[2'-(4''-amino-3''-isopropoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4''-amino-3''-isopropoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Propyl-1-hydroxy-12-[2'-(4''-amino-3''-propyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-acetylamino-3''-isopropyloxycyclohexy)-1'-methylvinyl]-23,25-dimethoxy-13,19,21,27-tetramethyl-11,28-dioxa-4-azatricyclo-[22.31.0⁴,⁹]octacos-18-ene-2,3,20,26-tetraone;

17-Ethyl-1,14-dihydroxy-12-[2'-[4''-(N'-t-butoxycarbonyl-D-phenylalanine)amido-3''-n-propyloxycyclohexyl]-1'-methylvinyl]23,25-dimethoxy-13,19,21,27-tetra-methyl-11,28-dioxa-4-azatricyclo[22.3.1.0⁴,⁹]octacos-18-ene-2,3,10,16-tetraone;

17-Ethyl-1,14-dihydroxy-12-[2'-[4''-(N'-t-butoxycarbonyl-L-phenylalanine)amido-3''-n-propyloxycyclohexyl]-1'-methylvinyl]-23,25-dimethoxy-13,19,21,27-tetra-methyl-11,28-dioxa-4-azatricyclo[22.3.1.0⁴,⁹]octacos-18-ene-2,3,10,16-tetraone;

17-Ethyl-1,14-dihydroxy-12-[2'-(4''-acetoxyacetylamino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1''''-adamantane carboxamido)-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-cyclo propanecarbox-amido-3''-isopropyloxycyclohexyl)-1'-methylvinyl]-23,25-dimethoxy-13,19,21,27-tetramethyl-11,28-dioxa-4-aza-tricyclo[22.3.1.0⁴,⁹]octacos-18-ene-2,3,10,16-tetraone;

17-Ethyl-1,14-dihydroxy-12-[2-(4''-formamido-3''-n-propyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-{2'-[4''',5'''-dicarboethoxy-1''',2''',3'''-triazole)-3''-n-propyloxycyclohexyl]-1'-methyl-vinyl}-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-benzylamino-3''-isopropyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4''-trimethylamino-3'-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone Iodide;

17-Ethyl-1,2,14-trihydroxy-12-[2'-(4''-acetylamino-3''-n-propyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-3,10,16-trione;

17-Ethyl-1,14-dihydroxy-12-{2'-[4''-(N'-phenylaminocarbonyl)amino-3''-isopropyloxycyclohexyl]-1'-methylvinyl}-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-{2'-[4''-(ethoxycarbonyl)amino-3''-n-propyloxycyclohexyl]-1'-methylvinyl}-23,25-di-methoxy-13,19,21,27-tetramethyl-11,28-dioxa-4-azatri-cyclo[22.3.1.0⁴,⁹]octacos-18-ene-2,3,10,16-tetraone;

17-Ethyl-1-hydroxy-12-[2'-(4''-acetylamino-3''-n-propyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-dimethylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-dimethylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-benzylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-benzylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-dimethylamino-3''-isopropyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-dimethylamino-3''-n-propyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-benzylamino-3''-isopropyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-benzylamino-3''-n-propyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-(2-phenyl-2-hydroxyethyl)amino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-morpholino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-morpholino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-amino-3''-n-butyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-amino-3''-butyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-amino-3''-(3-methylbutyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-amino-3''-(3-methylbutyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-amino-3''-(2-methylbutyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-amino-3''-(2-methylbutyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4'''-(N-(2-methyl-3-(4-hydroxyphenyl)propenyl)amino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4'''-(N-(2-methyl-3-(4-hydroxyphenyl)propenyl)amino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-(N-(3-(4-hydroxyphenyl)propenyl)amino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(N-(3-(4-hydroxyphenyl)propenyl)amino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(N-3-p henylpropenyl)amino-3''-methoxycyclohexyl)-1'-methylvinyl]-23,24-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-(N-3-phenylpropenyl)amino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetrone; and 17-Ethyl-1-hydroxy-12-[2'-(4''-(L-Trp)amido-3''-methoxycyclohexyl)-1'-methylvinyl]-23,25-dimethoxy-13,19,21,27-tetramethyl-11,28-dioxa-4-azatricyclo[22.3.1.0^{4,9}]pctacps-18-ene-2,3,10,16-tetraone;

and pharmaceutically acceptable salts thereof.

B. Preparation of Compounds Within the Scope of the Present Invention

The starting materials for the preparation of the compounds of this invention are represented by Formula II:

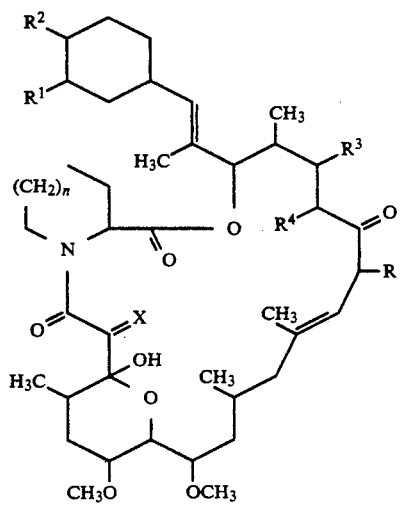

II wherein R is methyl, ethyl, propyl or allyl; $R^1$ and $R^2$ are, independently, hydroxy or methoxy; $R^3$ is hydrogen, hydroxyl, or $C_1$-$C_6$ alkoxy; $R^4$ is hydrogen, or $R^3$ and $R^4$ taken together form a double bond; X is O; and n is 1 or 2.

The production and characterization of compounds of Formula II is well known in the literature (see U.S. Pat. No. 4,894,366 issued Jan. 16, 1990; U.S. Pat. No. 4,929,611 issued May 29, 1990; U.S. Pat. No. 3,244,592 issued Apr. 15, 1966; EPO Publication No. 0,323,042; EPO Publication No. 0,356,399; PBJ Disclosure 63-17884; *J. Am. Chem. Soc.*, 1987, 109, 5031 and *J. Antibiotics*, 1987, 40, 1249). Both biological fermentation and synthetic processes may be found. A synthetic route to compounds of Formula II can involve modifications of a route described in *J. Am. Chem. Soc.*, 1989, 111, 1157.

Biological fermentation followed by synthetic modification is presently favored in the art as the method to produce compounds of Formula II. Organisms belonging to the genus Streptomyces such as *Streptomyces tsukubaensis*, No. 9993 and *Streptomyces hygroscopicus*, No. 7238 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where R is allyl, $R^1$ is methoxy, $R^2$ and $R^3$ are hydroxyl, $R^4$ is hydrogen, X is O and n is 2; (B) where R is ethyl, $R^1$ is methoxy, $R^2$ and $R^3$ are hydroxyl, $R^4$ is hydrogen, X is O and n is 2; (C) where R is methyl, $R^1$ is methoxy, $R^2$ and $R^3$ are hydroxyl, $R^4$ is hydrogen, X is O and n is 2; and (D) where R is allyl, $R^1$ is methoxy, $R^2$ and $R^3$ are hydroxyl, $R^4$ is hydrogen, X is O and n is 1.

A lyophilized sample of the isolated *Streptomyces tsukubaensis*, No. 9993 was deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposit date: Oct. 5, 1984), and then converted to Budapest Treaty route of the same depository on Oct. 19, 1985 under the new deposit number of FERM BP-927.

Using the four compounds produced in fermentation above, the remaining compounds of Formula II may be easily produced. The allyl of R may be conveniently reduced to propyl by well known methods, for example as disclosed in U.S. Pat. No. 4,894,366. The hydroxy's of $R^2$ or $R^3$ may be protected by well known methods, for example as disclosed in EPO Publication No. 0,323,042. The hydroxy of $R^2$ may be converted to methoxy by methods described in EPO Publication No. 0,323,042. In addition, the hydroxy of $R^3$ may be reduced to a hydrogen or eliminated to form a double bond with $R^4$ (by methods disclosed in U.S. Pat. No. 4,894,366 or EPO Publication 0,323,042). The hydroxy of $R^2$ may be oxidized to the ketone when $R^3$ is a protected hydroxy by methods as disclosed herein. The carbonyl of X may be reduced to a hydroxy by methods disclosed in EPO Publication 0,323,042 or by methods disclosed in copending U.S. Patent Application Ser. No. 486,700, filed Mar. 1, 1990.

The methoxy of $R^1$ as produced may be replaced with hydroxy or demethylated and subsequently protected as desired, if necessary. This demethylation of $R^1$ may be carried out in a fermentation reaction using the compounds of Formula II as a feedstock. For instance, compound A named under Formula II above may be demethylated at $R^1$ above by using the microorganism Actinomycetales ATCC No. 53771 (described in U.S. Pat. No. 4,981,792 issued Jan. 1, 1991). Similarly, compound B named under Formula II above may be demethylated at $R^1$ above using the microorganism Actinoplanacete sp. ATCC No. 53771 (described in EPO Publication No. 0,349,061). In addition the compound of Formula II wherein $R^1$ is hydroxy, $R^2$ is hydroxy, X is O, $R^3$ is hydroxy, $R^4$ is hydrogen, R is ethyl and n is 2 may be produced directly by fermentation using the mutant microorganism *Streptomyces hygroscopicus* sup. ascomyceticus, No. 53855 (being a blocked mutant of *Streptomyces hygroscopicus* sup. ascomyceticus, No. 14891) (as described in EPO Publication No. 0,388,152). Similarly, the compound of Formula II wherein $R^1$ is hydroxy, $R^2$ is hydroxy, X is O, $R^3$ is hydroxy, $R^4$ is hydrogen, R is methyl and n is 2 may be produced directly by fermentation using the mutant microorganism *Streptomyces hygroscopicus* sup. ascomyceticus, No. 53855 (being a blocked mutant of *Streptomyces hygroscopicus* sup. ascomyceticus, No. 14891) (as described in EPO Publication No. 0,388,153). Also, the compound of Formula II wherein $R^1$ is hydroxy, $R^2$ is hydroxy, $R^3$ is hydroxy, $R^4$ is hydrogen, R is allyl, X is O and n is 2 and the compound of Formula II wherein $R^1$ is keto, $R^2$ is hydroxy, $R^3$ is hydroxy, $R^4$ is hydrogen, R is allyl, X is O and n is 2 may be produced directly by fermentation using the microorganism *Streptomyces tsukubaensis*, No. 9993 (described in EPO Publication No. 0,353,678). The hydroxy of C-3" may be protected by methods similar to those known for the protection of the hydroxy's of $R^3$ and/or C-4", for example as disclosed in U.S. Pat. No. 4,894,366.

Suitable protecting groups for hydroxyl include those groups well known in the art which are: 1-(lower alkylthio)(lower)alkyl, wherein "lower alkyl" indicates a straight, cyclic or branched chain of one to six carbon atoms, such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be $C_1$-$C_4$ alkylthiomethyl and the most preferred one may be $C_1$-$C_4$ alkylthiomethyl methylthiomethyl; trisubstituted silyl such as tri(lower)alkylsilyl (e.g. trimethylsilyl, triethylsilyl, tributysilyl, tri-i-propylsilyl, t-butyldimethylsilyl, tri-t-butylsilyl, etc.), lower alkyldiarylsilyl (e.g. methyl-diphenylsilyl, ethyl-diphenylsilyl, propyl-diphenylsilyl, t-butyldiphenylsilyl, etc.), and the like, in which the preferred one may be tri($C_1$-$C_4$)alkylsilyl and $C_1$-$C_4$ alkyldiphenylsilyl, and the most preferred one may be tert-butyl-dimethylsilyl, tri-i-propylsilyl and tert-butyl-diphenylsilyl; acyl such as aliphatic acyl, aromatic acyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in U.S. Pat. No. 4,894,366, issued Jan. 16, 1990 and U.S. Pat. No. 4,929,611, issued May 29, 1990.

The compounds of the present invention which are represented by Formula I are prepared by the methods shown in the following Reaction Schemes wherein R, $R_1$, $R_2$, $R_3$, $R_4$, X and n are as defined above unless otherwise indicated. It will be readily apparent to one of ordinary skill in the art reviewing the synthetic route depicted below that other compounds within Formula I can be synthesized by substitution of appropriate reactants and agents in the synthesis shown below.

As shown in Reaction Scheme A the C-14-OTIPS protected macrolide is prepared from the 4'',14-dihydroxy macrolide and reacted with diphenyl phosphoryl azide in the presence of triphenyl phosphine and diethyl azodicarboxylate to introduce the azide substituent at the C-4'' position. The protecting group at C-14 is removed and reduction of the azide with triphenylphosphine/water gives the C-4'' amino compound. This route may be modified to prepare C-3'' amino macrolides as well.

An alternate route to C-4'' or C-3'' amino substituted compounds is shown in Reaction Scheme B. The macrolide is protected if necessary and reacted with o-nitrobenzenesulfonyl chloride or trifluoromethanesulfonyl anhydride in the presence of an amine base to give the mono- or di- C-4'' and/or C-3'' o-nitrobenzenesulfonyl or trifluoromethanesulfonyl derivative. The leaving group is displaced by treatment with sodium azide (or an alternative nucleophilic amine), the protecting group is removed, if necessary, by treatment with hydrogen fluoride and, if necessary, the azide is reduced with triaryl phosphine/water or trialkyl phosphine/water to give the amino compound. Azides can be reduced with other reagents known in the art, such as with hydrogen sulfide, propane-1,3-dithol, or thioacetic acid or by catalytic hydrogenation over a suitable catalyst.

As shown in Reaction Scheme C, the opposite stereochemistry of the resultant amino compound can be obtained by proceeding thru an epoxide as a synthetic intermediate. Reaction of the C-3''-beta, C-4''-alpha dihydroxy macrolide (wherein $R^3$ is hydrogen or protected hydroxy) with o-nitrobenzenesulfonyl chloride followed by separation of the isomers and treatment with a tertiary amine base, such as triethylamine, gives the two possible epoxides. The beta-epoxide may be opened by treatment with azide to give the C-3''-beta-hydroxy C-4''-alpha-azido macrolide. The C-3''-hydroxyl group may be alkylated or protected, prior to reduction of the azide to the amine (by the methods of Reaction Scheme B), and the resultant amine may be further modified by methods described in Reaction Scheme E.

An amino substituent may also be introduced at C-4'' by reductive amination of a keto-substituted macrolide as shown in Reaction Scheme D. The ketone at C-4'' is prepared by Swern oxidation of a suitably protected hydroxy-macrolide. Reductive amination of the ketone with an appropriate amine gives the corresponding amino-macrolide as a mixture of epimers at C-4''.

Compounds bearing a C-3'' and/or a C-4'' amino substituent may be further modified by methods which are known in the art as exemplified in Reaction Scheme E. These methods include, but are not limited to such methods as: acylation with an appropriate acid halide or acid anhydride in the presence of an amine base to give the corresponding amide, coupling with an appropriate carboxylic acid to give the corresponding amide, reaction with an isocyanate to give the urea derivative, treatment with an ethyl chloroformate equivalent to give the corresponding urethane or alkylation with an appropriate alkyl halide to give the corresponding secondary, tertiary or quarternary alkyl amine.

An amino substituent may also be modified at C-3'' and/or C-4'' by reductive amination of an amino-substituted macrolide as shown in Reaction Scheme F (wherein $R^{5a}/R^{5b}$ and $R^{6a}/R^{6b}$ are respectively equivalent to $R^5$ and $R^6$ absent one methylene group). The imine is prepared by reaction of the amine with an appropriate aldehyde or ketone. Reduction of the imine with sodium cyanoborohydride or similar reducing agent gives the corresponding amino-macrolide. The reductive amination may be repeated to give the mixed-disubstituted amino macrolides.

As shown in Reaction Scheme G, (wherein $R^2$ is $C_{1-6}$ alkyl, or $C_{2-6}$ alkenyl) a solution of the 3'', 4''-dihydroxy macrolide in an inert organic solvent such as methylene dichloride, chloroform, pentane, hexane, cyclohexane, heptane or the like or mixtures thereof is treated with a trichloroacetimidate (prepared by the reaction of an appropriate sodium alkoxide with trichloracetonitrile, such as described by Wessel, H.P., Iversen, T., Bundle, D.R., *J. Chem., Soc.*, Perkins Trans. I, 1985, 2247) in the presence of a mild acid catalyst such as trifluoromethanesulfonic acid, p-toluenesulfonic acid, methanesulfonic acid, benzensulfonic acid, p-nitrobenzenesulfonic acid, p-bromobenzenesulfonic acid, p-chlorobenzensulfonic acid, or p-methoxybenzenesulfonic acid, or mixtures thereof at a temperature of 20°-50° C., preferably 40° C., for a period of one hour to seven days, preferably 6 hours, to give a mixture of the 3''-0-alkyl or -alkenyl 4''-hydroxy macrolide and the 3''-hydroxy 4''-0-alkyl or -alkenyl macrolide.

The free hydroxyl group at C-3'' or C-4'' may be converted to an amino-containing functionality by the procedures described in Reaction Schemes A thru F.

As shown in Reaction Scheme H the macrolide (where $R^2_a$ is alkenyl or alkynyl and wherein $R^3_a$ is hydroxy or $C_{1-6}$ alkoxy, $R^4_a$ is hydrogen, or $R^3_a$ and $R^4_a$ taken together form a double bond) is reduced under an atmosphere of hydrogen in the presence of a noble metal catalyst, such as rhodium on carbon catalyst or rhodium on alumnina catalyst, at a pressure of atmospheric pressure to a pressure of 40 psig, at or near room temperature in an organic solvent such as ethyl acetate or ethanol for about 1 to 24 hours, or until the requisite amount of hydrogen is absorbed to reduce the olefin and give the reduced macrolide.

The procedures described in Reaction Schemes A thru F may optionally be conducted following the procedures of Reaction Scheme G and H.

REACTION SCHEME A
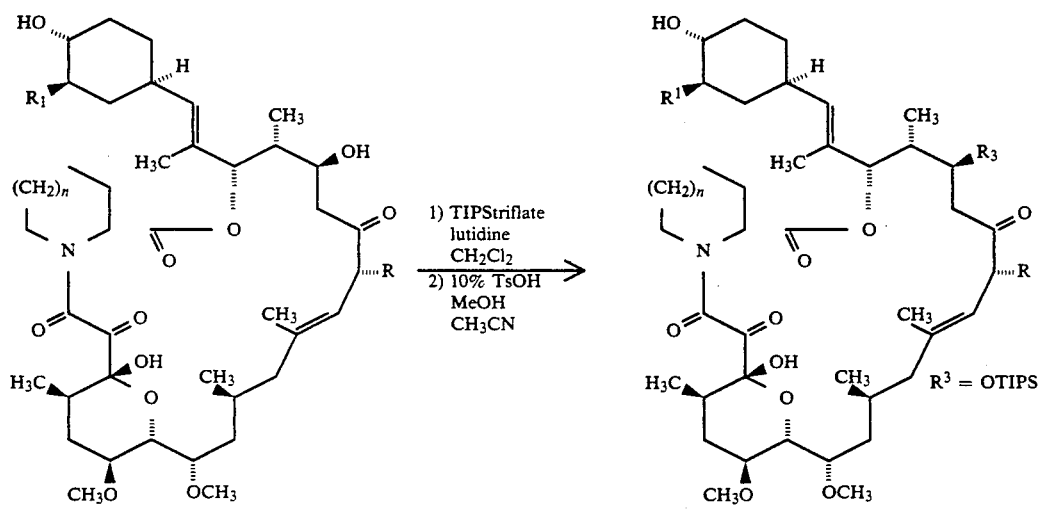
R = Et
R¹ = OCH₃
n = 2
1) Ph₃P, DEAD
   (PhO)₂P(O)N₃
   THF
2) HF(48%), CH₃CN
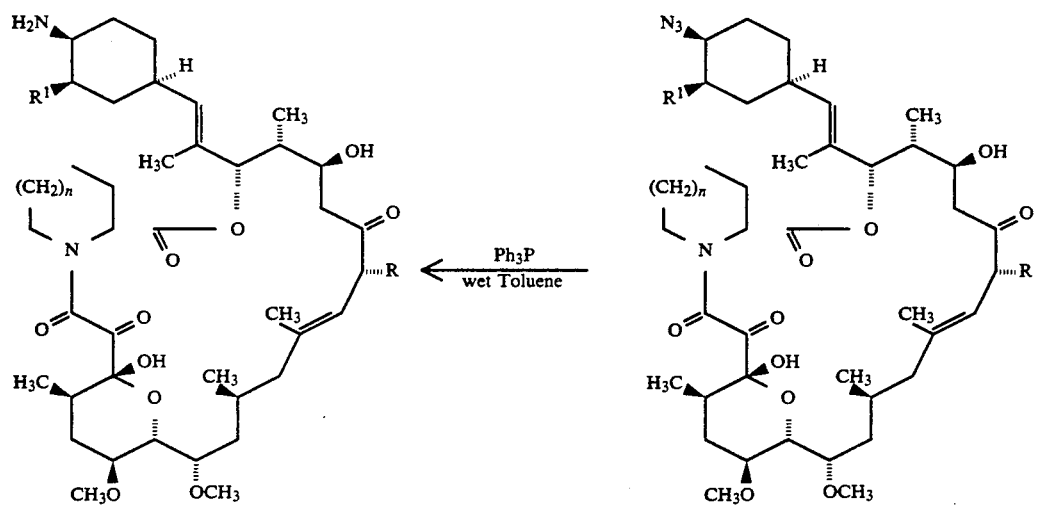

REACTION SCHEME B
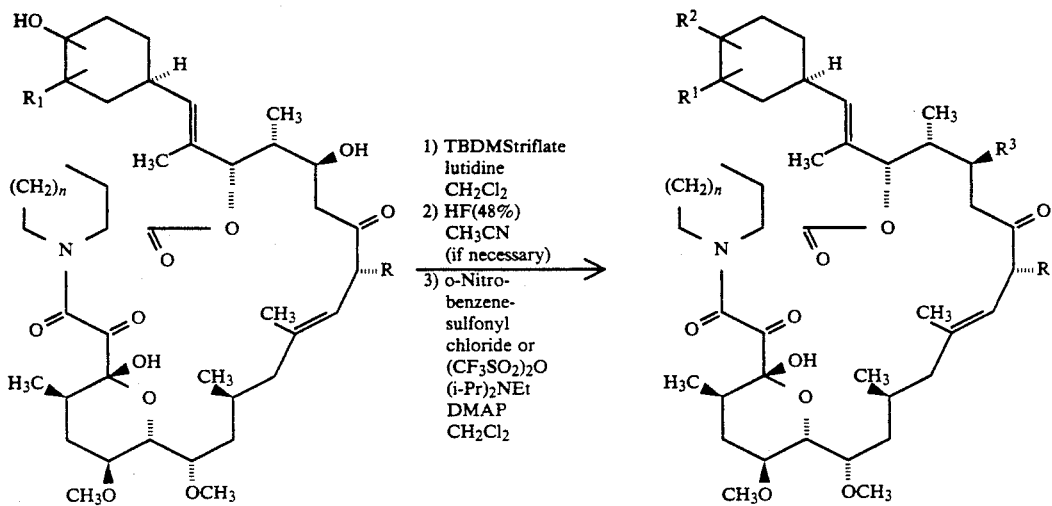
$R^1$ = OCH$_3$ or OH
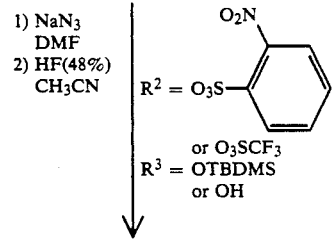
$R^2$ = O$_3$S−(o-NO$_2$-C$_6$H$_4$) or O$_3$SCF$_3$
$R^3$ = OTBDMS or OH
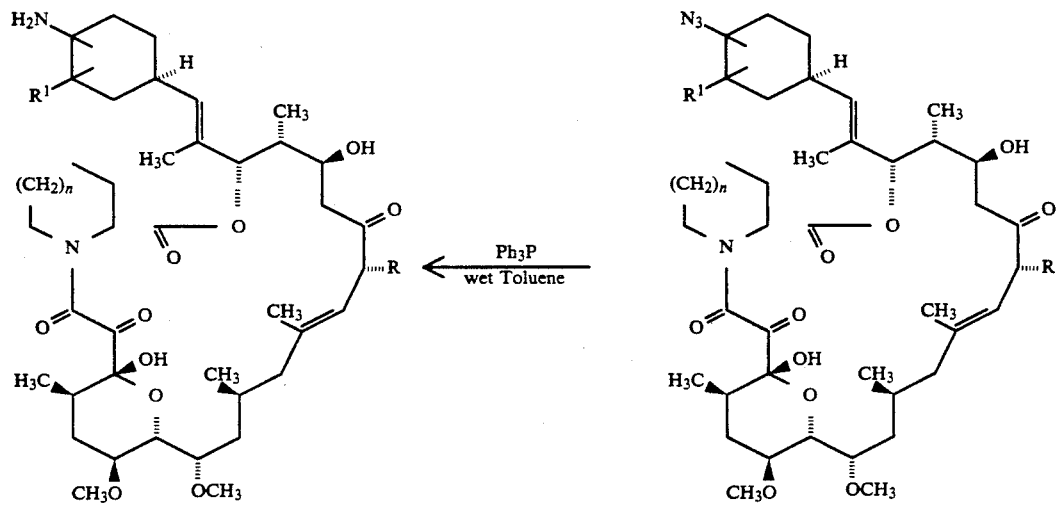

REACTION SCHEME C
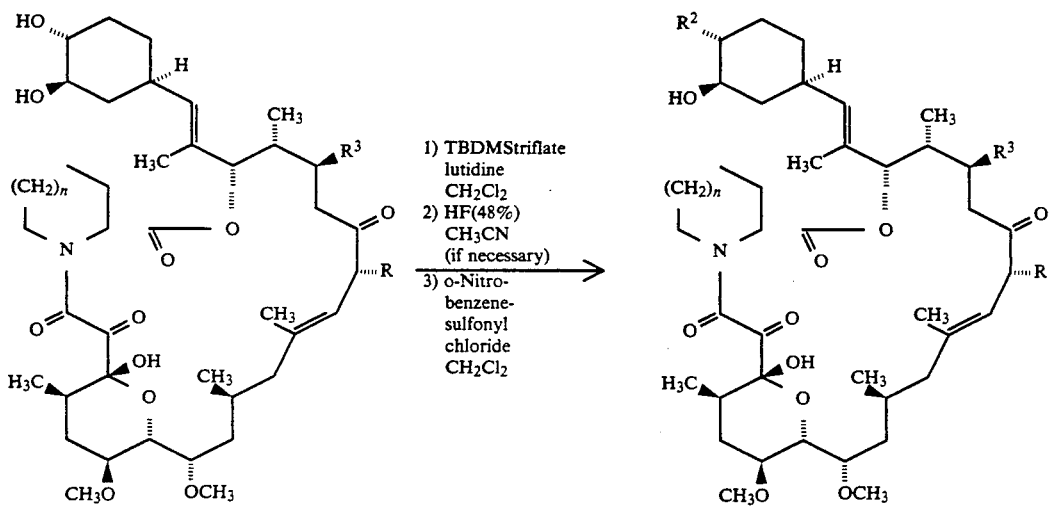
R³ = OH or H
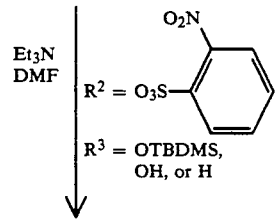
Et₃N
DMF
R² = O₃S-(2-nitrophenyl)
R³ = OTBDMS, OH, or H
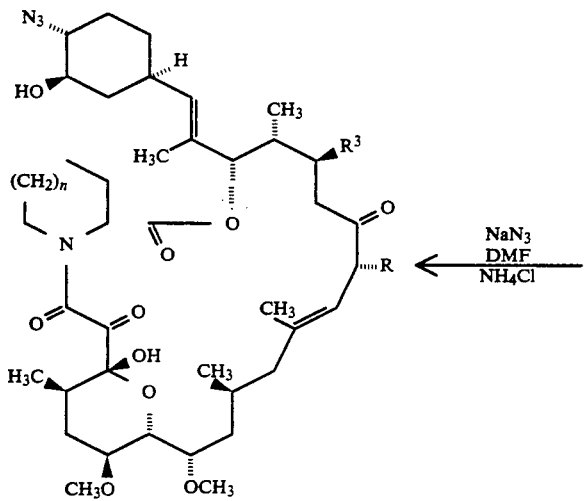
← NaN₃ / DMF / NH₄Cl
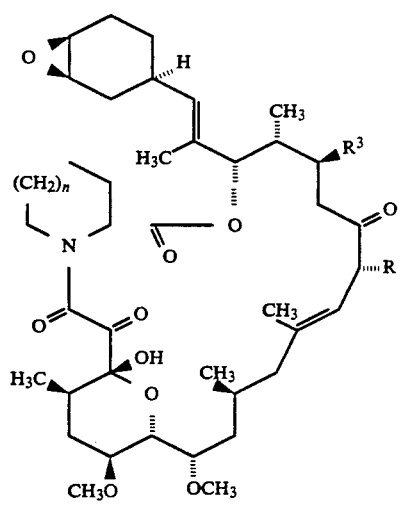

REACTION SCHEME D
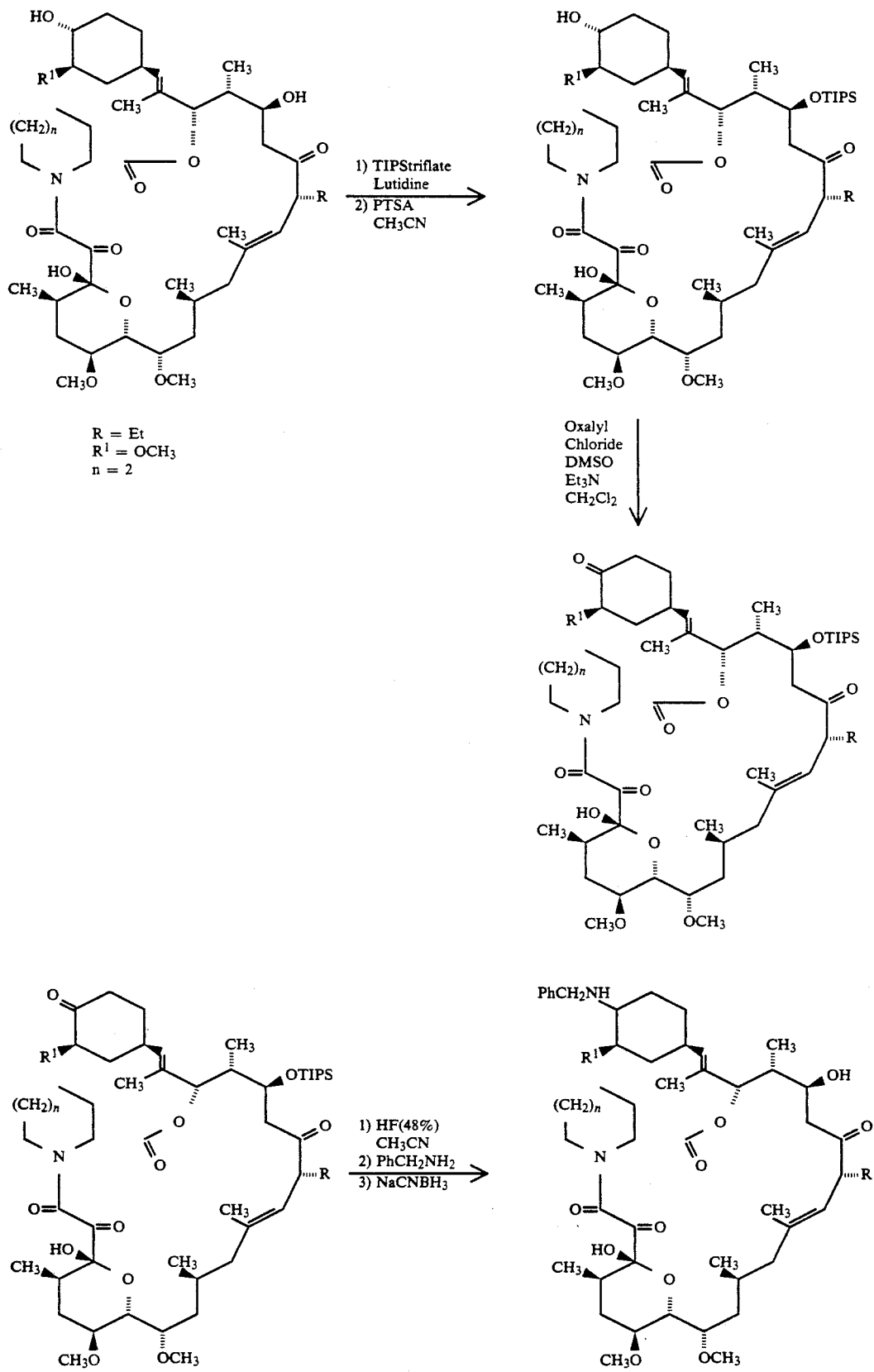

REACTION SCHEME E
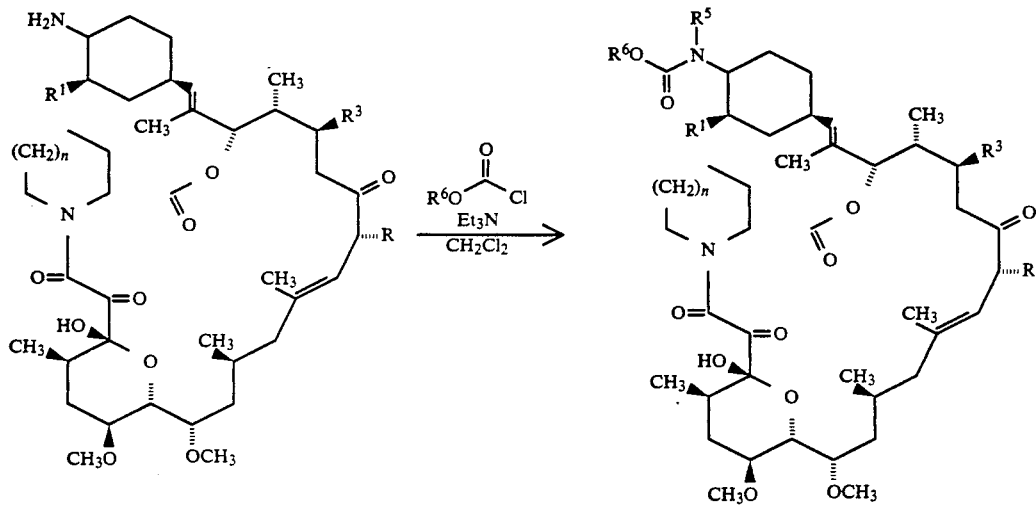
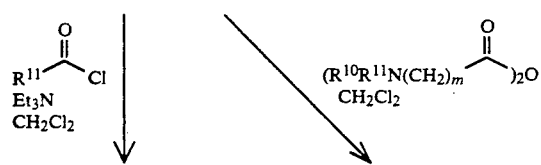
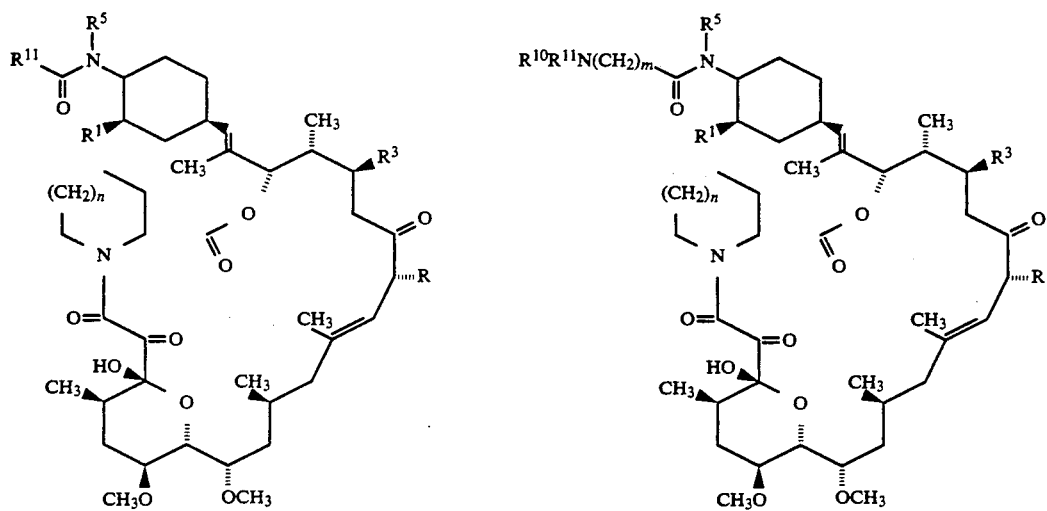

REACTION SCHEME F
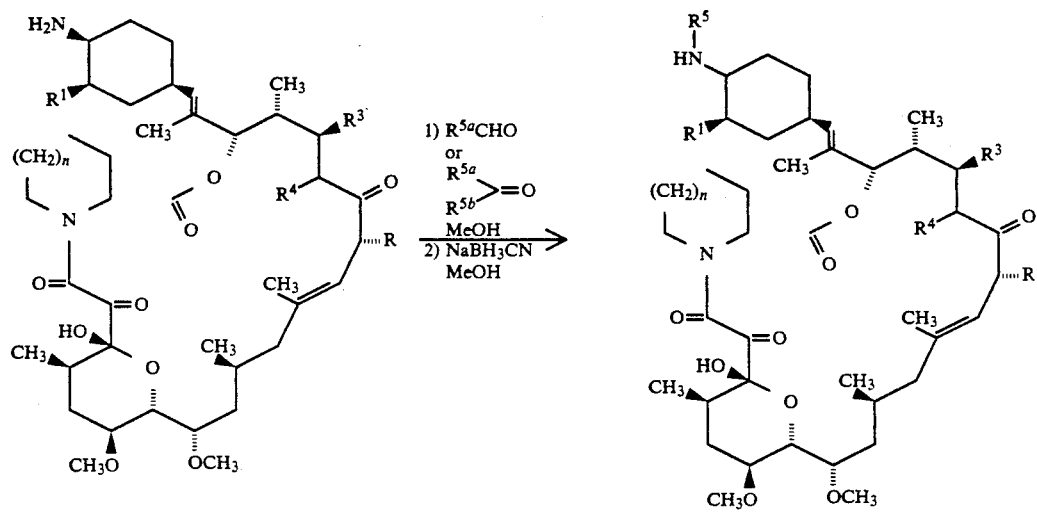
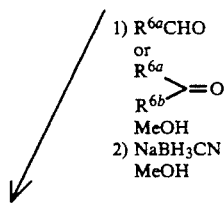
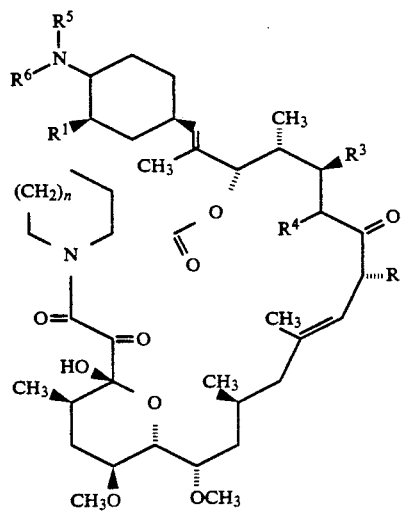

REACTION SCHEME G
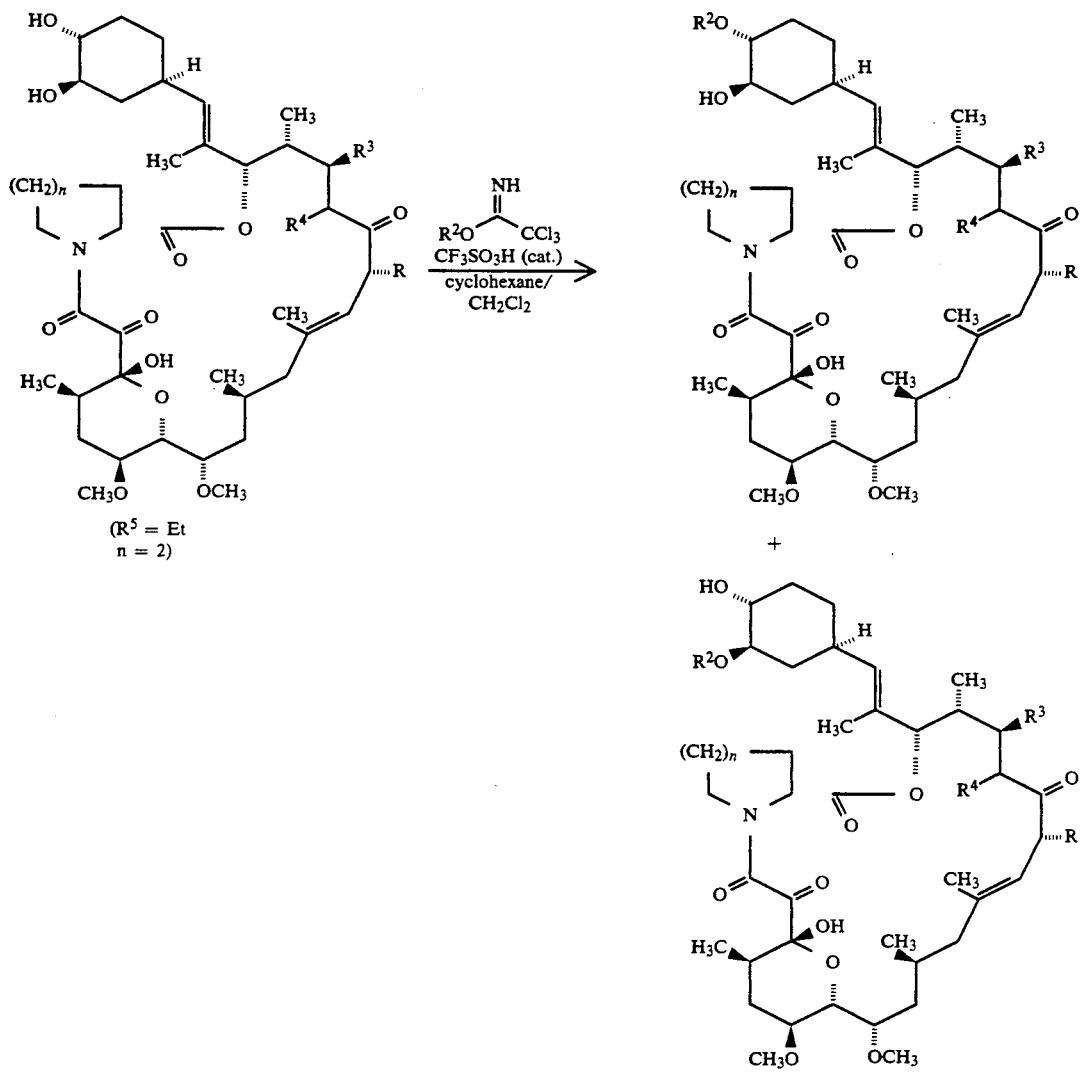
REACTION SCHEME H
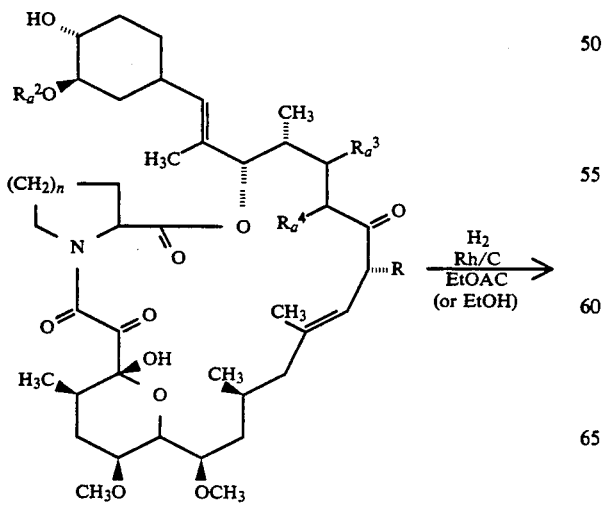
-continued
REACTION SCHEME H
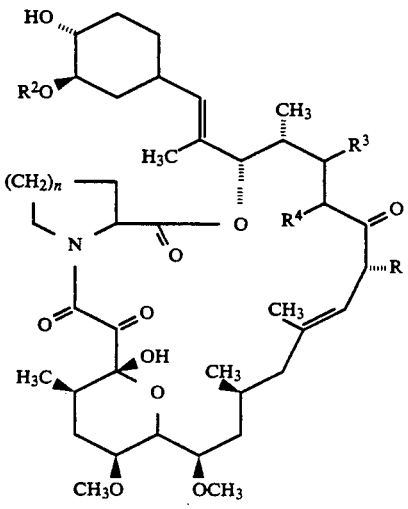

Suitable protecting groups for amino include those groups well known in the art which are: benzyl, benzyloxymethyl, benzyloxycarbonyl (carbobenzyloxy), benzylsulfonyl, 2-bromoethyloxycarbonyl, t-butyloxycarbonyl, 2-chlorobenzyloxycarbonyl, 2-chloroethyloxycarbonyl, di-t-amyloxycarbonyl, 9-fluoroenylmethyloxycarbonyl, isopropoxycarbonyl, 4-methoxybenzyloxycarbonyl, 4-nitrobenzyloxycarbonyl, 2-nitrophenylsulfonyl, phthaloyl, 2,2,2-trichloro-t-butyloxycarbonyl, trifluoroacetyl, triphenylmethane and vinyloxycarbonyl groups and the like in which the preferred ones are the t-butyloxycarbonyl, benxyloxycarbonyl (carbobenzyloxy), 2-chlorobenzyloxycarbonyl, 4-methoxybenzyloxycarbonyl and 4-nitrobenzyloxycarbonyl groups and in which the more preferred ones are the t-butyloxycarbonyl and the benzyloxycarbonyl (carbobenzyloxy) groups.

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereo isomer(s) of starting and object compounds due to asymmetric carbon atom(s) or double bond(s) of the object compounds of Formula I may occasionally be transformed into the other stereo isomer(s), and such cases are also included within the scope of the present invention.

In the present invention, compounds with asymmetric centers may occur as racemates, racemic mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (see for example, *J. Am. Chem. Soc.* 1989, 111, 1157; *J. Am. Chem. Soc.* 1990, 112, 2998; *J. Org. Chem.* 1990, 55, 2786; *J. Am. Chem. Soc.* 1990, 112, 5583. *Tetrahedron Lett.* 1988, 29, 277; *Tetrahedron Lett.* 1988, 29, 281; *Tetrahedron Lett.* 1988, 29, 3895; *J. Org. Chem.* 1988, 53, 4643; *Tetrahedron Lett.* 1988, 29, 4245; *Tetrahedron Lett.* 1988, 29, 4481; *J. Org. Chem.* 1989, 54, 9; *J. Org. Chem.* 1989, 54, 11; *J. Org. Chem.* 1989, 54, 12; *J. Org. Chem.* 1989, 54, 15; *J. Org. Chem.* 1989, 54, 17; *Tetrahedron Lett.* 1989, 30, 919; *Tetrahedron Lett.* 1989, 30, 1037; *J. Org. Chem.* 1989, 54, 2785; *J. Org. Chem.* 1989, 54, 4267; *Tetrahedron Lett.* 1989, 30, 5235; *Tetrahedron Lett.* 1989, 30, 6611; *Tetrahedron Lett.* 1989, 30, 6963; Synlett 1990, 38; *J. Org. Chem.* 1990, 55, 2284; *J. Org. Chem.* 1990, 55, 2771; *J. Org. Chem.* 1990, 55, 2776; *Tetrahedron Lett.* 1990, 31, 1439; *Tetrahedron Lett.* 1990, 31, 1443; *Tetrahedron Lett.* 1990, 31, 3007; *Tetrahedron Lett.* 1990, 31, 3283, 3287).

The compounds of the present invention are capable of forming salts with various inorganic and organic acids and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, maleate, methanesulfonate, 2-naphthalenesulfonate, oxalate, pamoate, persulfate, picrate, pivalate, propionate, succinate, tartrate, tosylate, and undecanoate. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others.

C. Utility of the compounds within the scope of the invention

The compounds of Formula I may be employed as immunosuppressants or antimicrobial compounds by methods and in dosages known in the prior art for compounds of Formula II. These compounds possess pharmacological activity such as immunosuppressive activity, antimicrobial activity, and the like, and therefore are useful for the treatment and prevention of the resistance to transplantation or transplantation rejection of organs or tissues such as heart, kidney, liver, duodenum, small-bowel, medulla ossium, skin, pancreatic-islet-cell, etc., graft-versus-host diseases by medulla ossium transplantation, autoimmune diseases such as rheumatoid arthritis, systemic lupus erythematosis, Hashimoto's thyroiditis, multiple sclerosis, myasthenia gravis, type I diabetes, uveitis, allergic encephalomyelitis, glomerulonephritis, etc., and infectious diseases caused by pathogenic microorganisms. The compounds of Formula I are also useful for treating inflammatory and hyperproliferative skin diseases and cutaneous manifestations of immunologically-mediated illnesses such as: psoriasis, atopical dermatitiis, contact dermatitis and further eczematous dermatitises, seborrhoeic dermatitis, *Lichen planus*, Pemphigus, bullous Pemphigoid, *Epidermolysis bullosa*, urticaria, angioedemas, vasculitides, erythemas, cutaneous eosinophilias or *Alopecia areata*.

The compounds of Formula I are further useful for treating reversible obstructive airways disease, including conditions such as asthma, including bronchial asthma, allergic asthma, intrinsic asthma, extrinsic asthma and dust asthma, particularly chronic or inveterate asthma (for example late asthma and airway hyperreponsiveness), bronchitis and the like. The compounds of Formula I may also be useful for treating hepatic injury associated with ischemia.

The compounds of Formula I may also antagonize the immunosuppressive effects of FK-506-type immunosuppressants and so be useful in reversing their immunosuppressive activity and/or diminishing their toxic effects.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semi-solid, or liquid form, and in addition auxiliary, stabilizing, thickening and coloring agents and perfumes may be used. For example, the compounds of Formula I nay be utilized with hydroxypropyl methylcellulose essentially as described in U.S. Pat. No. 4,916,138, issued Apr. 10, 1990. The active object compound is included in the pharmaceutical composition in an amount sufficient to produce the desired effect upon the process or condition of diseases.

For the treatment of these conditions and diseases caused by immmunoirregularity a compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For modifying the activity and/or toxicity of FK-506-type immunosuppressants of Formula II, a compound of Formula I may be administered prior to, in conjunction with or subsequent to the administration of a compound of Formula II.

Dosage levels of the compounds of the present invention are of the order from about 0.001 mg to about 50 mg per kilogram of body weight per day, preferably from about 0.01 mg to about 1.0 mg per kilogram body weight per day, are useful in the treatment of the above-indicated conditions (from about 0.07 mg to about 3.5 g per patient per day, assuming a 70 kg patient). In addition, the compounds of the present invention may be administered on an intermittent basis; i.e. at semiweekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain from about 0.5 mg to about 500 mg of active ingredient. For topical administration in larger mammals a preparation containing a 1-3% concentration of active agent may be utilized.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

17-Ethyl-1,14-dihydroxy-12-[2'-(4"-azido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A: Preparation of 17-Ethyl-1-hydroxy-12-[2'-(4"-triisopropylsilyloxy-3"-methoxycyclohexyl)-1'-methylvinyl]-14-triisopropylsilyloxy-23,25-dimethoxy13,19,21,27-tetramethyl-11,28-dioxa-4-azatricyclo[22.3.1.0$^{4,9}$]octacos-18-ene-2,3,10,16-tetraone To a cooled solution (0° C.) of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (120 mg) in dry methylene chloride (15 ml) was added 2,6-lutidine (64.3 mg) followed by triisopropylsilyl trifluoromethanesulfonate (184 mg). Reaction temperature was raised to r.t. and stirred overnight under nitrogen atmosphere. The reaction was quenched with 10 ml of water and extracted with ethyl acetate. Organic layer was washed (water, sat'd NaHCO$_3$, sat'd NaCl) and dried (anhydrous MgSO$_4$). Removal of solvent followed by chromatography on silica gel (70% hexane/ethyl acetate) gave 150 mg of product.

MASS: (FAB) 1110 (M+ +Li).

Step B: Preparation of 17-Ethyl-1-hydroxy-12-[2'-(4"-hydroxy-3"-methoxycyclohexyl)-1'-methylvinyl]-14-triisopropylsilyloxy-23,25-dimethoxy-13,19,21,27-tetramethyl-11,28-dioxa-4-azatricyclo[22.3.1.0$^{4,9}$]octacos-18-ene-2,3,10,16-tetraone The title compound from Example 1A (680 mg) was dissolved in methylene chloride (45 ml) and 10% solution of p-toluenesulfonic acid in methanol (45 ml) was added with stirring. The mixture was stirred at room temperature and the progress was followed by tlc analysis. After 4 hr, reaction was quenched with sat'd sodium bicarbonate and extracted with ethyl acetate three times. Normal work-up and removal of solvent followed by purification on silica gel column (80% ethyl acetate/hexane) gave 560 mg of the product as a white solid.

MASS: (FAB) 954 (M+ +Li).

Step C: Preparation of 17-Ethyl-1-hydroxy-12-[2'-(4"-azido-3"-methoxycyclohexyl)-1'methylvinyl]-14-triisopropylsilyloxy-23,25-dimethoxy-13,19,21,27-tetramethyl-11,28-dioxa-4-azatricyclo[22.3.1.0$^{4,9}$]octacos-18-ene-2,3,10,16-tetraone A solution of triphenylphosphine (78.6 mg) and diethyl azodicarboxylate (52.2 mg) in dry tetrahydrofuran (THF, 2 ml) was added to a solution of the title compound from Example 1B (284 mg) in THF (10 ml) followed by a solution of diphenylphosphorylazide (82.6 mg in 1 ml of THF). The reaction mixture was stirred at 45° C. and the progress was monitored by tlc analysis. Reaction was quenched with water and extracted with ethyl acetate. Solvent was removed in vacuo and the residue was purified by preparative tlc on silica gel (66% ethyl acetate/hexane) to give the product (96 mg).

MASS: (FAB) 979 (M+ +Li).
IR: 2080$^{-cm}$(-N$_3$).
$^1$H NMR: δ4.6(bs, 1H, 4"-H).

Step D: Preparation of 17-Ethyl-1,14-di hydroxy-12-[2'-(4"-azido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of the title compound from Example 1C (10 mg) in acetonitrile (1 ml) was added 0.2 ml of hydrogen fluoride (48%) at room temperature. The reaction mixture was stirred for 6 hr, quenched with aqueous sodium bicarbonate and extracted with ethyl acetate. Removal of solvent, followed by chromatography on silica gel (5% i-PrOH/CH$_2$Cl$_2$) gave 6.5 mg of the title compound (Mass, IR, $^1$H and $^{13}$C NMR data consistent with the proposed structure).

MASS: (FAB) 823 (M$^+$ +Li).
IR: 2080$^{-cm}$(-N$_3$).

EXAMPLE 2

17-Ethyl-1,14-dihydroxy-12-[2'-(4"-azido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (ALTERNATE ROUTE)

Step A: Preparation of 17-Ethyl-1-hydroxy-1-2-[2'-(4"-t-butyldimethylsilyloxy-3"-methoxycyclohexyl)-1'-methylvinyl]-14-t-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone To a cooled solution (0° C.) of 17-ethyl-1,14-dihydroxy-12-[2'-(4"-hydroxy-3"-methoxycyclohexyl)1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (395 mg) in dry methylene chloride (15 ml) was added 2,6-lutidine (160 mg) followed by t-butyldimethylsilyl triflouromethanesulfonate (250 mg).

Reaction temperature was raised to r.t. and stirred under nitrogen atmosphere. After 6 hr, the reaction was quenched with 10 ml of water and extracted with ethyl acetate. Organic layer was washed (water, sat'd NaHCO$_3$, sat'd NaCl) and dried (anhydrous MgSO$_4$). Removal of solvent under reduced pressure gave 500 mg of crude product.

MASS: (FAB) 1023 (M$^+$ +Li).

Step B: Preparation of 17-Ethyl-1-hydroxy-12-[2'-(4"-hydroxy-3"-methoxycyclohexyl)-1'-methylvinyl]-14-t-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone The crude product from Example 2A (500 mg) was dissolved in acetonitrile (20 ml) and 100 µl of hydrogen fluoride (48%) was added. Reaction was stirred for 20 minutes at room temperature, quenched with sat'd sodium bicarbonate, then extracted with ethyl acetate. Removal of solvent in vacuo followed by chromatography on silica gel (80% ethyl acetate/hexane) gave 300 mg of product (Mass, $^1$H and $^{13}$C NMR data consistent with the proposed structure).

Step C: Preparation of 17-Ethyl-1-hydroxy-12-{2'-{4"-(2'''-nitrobenzenesulfonyl)-3"-methoxycyclohexyl}1'-methylvinyl]-14-t-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone To a solution of the title compound of Example 2B (721.8 mg) in dry methylene chloride (20 mL) was added diisopropylethylamine (247.4 mg) followed by 2-nitrobenzenesulfonyl chloride (358.8 mg) and then N,N-dimethylaminopyridine (122.2 mg). The yellow solution was stirred at room temperature under a nitrogen atmosphere for 4 hr, and quenched with sat'd aqueous sodium bicarbonate. Organic layer was washed (water, sat'd NaHCO$_3$, sat'd NaCl), dried (anhydrous Na$_2$SO$_4$) and the solvent was removed in vacuo. Chromatography on silica gel (65% ethyl acetate/hexane) gave 700 mg of the title compound (Mass, $^1$H and $^{13}$C NMR data consistant with the proposed structure).

Step D: Preparation of 17-Ethyl-1-hydroxy-12-[2'-(4"-azido-3"-methoxycyclohexyl)-1'-methylvinyl]-14-t-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of the title compound of Example 2C (390 mg) in dry dimethylformamide (5 ml) was added sodium azide (115.7 mg) in one portion. The reaction was heated at 80° C. under nitrogen atmosphere for 4.5 hr. Reaction mixture was cooled to r.t., poured into water (50 ml), and extracted with ethyl acetate. Normal work-up followed by purification via preparative tlc on silica gel (2000 microns, 33% ethyl acetate/hexane) gave 170 mg of product (Mass, $^1$H and $^{13}$C NMR data consistent with the proposed structure).

Step E: Preparation of 17-Ethyl-1,14-dihydroxy-12-[2'-(4"-azido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of the title compound of Example 2D (150 mg) in acetonitrile at room temperature was added hydrofluoric acid (48%, 1.5 ml). The reaction was stirred for 1.5 hr., quenched with sat'd aqueous sodium bicarbonate and extracted with ethyl acetate. The solvent was removed and the residue was purified by preparative tlc on silica gel (2000 microns, 50% ethyl acetate/hexane) to give 128 mg of the title compound.

MASS: (FAB) 823 (M$^+$ +Li).

EXAMPLE 3

17-Ethyl-1,14-dihydroxy-12-[2'-(4"-amino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1,14-dihydroxy-12-[2'-(4"-azido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (28 mg) and triphenylphosphine (9 mg) in 1 ml of wet toluene was stirred at 70° C. overnight. The solvent was removed under reduced pressure, and the residue was purified by preparative tlc on silica gel (1000 microns, 1% NH$_4$OH in 5% i-PrOH/CH$_2$Cl$_2$) to give 19 mg of the title compound.

MASS: (FAB) 791 (M$^+$ +H).

EXAMPLE 4

17-Ethyl-1,14-dihydroxy-12-[2'-(4"-acetylamino-3"-methoxycyclohexyl)-1'-methylvinyl]-23,25-dimethoxy-13,19,21,27-tetramethyl-11,28-dioxa-4-azatricyclo[22.31.0$^{4,9}$]octacos-18-ene-2,3,20,26-tetraone To a solution of 17-ethyl-1,14-dihydroxy-12-[2'-(4"-amino-3"-methoxy-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (30 mg) in dry methylene chloride (0.2 ml) was added triethylamine (10 µl) followed by a solution of acetic anhydride in methylene chloride (10 mg in 1 ml) at r.t. Reaction was stirred for 30 minutes and the solvent was removed under nitrogen flow. The crude product was purified by preparative tlc on silica gel (100 microns, 6% i-PrOH/CH$_2$Cl$_2$) to give 25 mg of the title compound.

MASS: (FAB) 833 (M+ +H).

$^1$H NMR: δ5.6 (d, 1H, NH), 4.21 (b.s, 1H, 4''-H), 2.0 (s, 3H's, COCH$_3$).

$^{13}$C NMR: δ170 (CH$_3$CONH-).

EXAMPLE 5

17-Ethyl-1,14-dihydroxy-12-[2'-(4''-N-(2-propenyl)amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The compound 17-ethyl-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (30 mg) was placed in a dry flask equipped with stir bar and condenser. Dry toluene (1 ml) was added followed by diisopropylethylamine (13 mg) and freshly distilled allyl bromide (40.5 mg) at 0° C. with stirring. Reaction temperature was raised to 70° C. gradually and stirred for 2 hr. The reaction mixture was cooled, and the solvent was removed under nitrogen flow. The residue was purified by preparative tlc on silica gel (1000 microns, 10% MeOH/CH$_2$Cl$_2$) to give 20 mg of the title compound.

MASS: (FAB) 831 (M+ +H).

$^1$H NMR: 5.89 (ddt, 1H, Vinyl H).

EXAMPLE 6

17-Ethyl-1,14-dihydroxy-12-[2'-[4''-(N'-t-butoxycarbonyl-D-phenylalanine)amido-3''-methoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (44.7 mg) in dry methylene chloride (2 ml) was added 102 mg of freshly prepared BOC-D-phenylalanine anhydride (prepared as described in *Solid Peptide Sythesis*, p. 32, J. M. Steward and J. D. Young, Pierce Chemical Company) under nitrogen Reaction was stirred at room temperature and the process was followed by tlc analysis. After 2.5 hr, the reaction mixture was subjected to work-up and preparative tlc on silica gel (1000 microns, 5% i-PrOH/CH$_2$Cl$_2$) to give 50 mg of the title compound.

MASS: (FAB) 1044 (M+ +Li).

$^1$H NMR: δ7.23 (m, 5H's, aromatic), 5.89 (d, 1H, 4''-NH), 4.3 (bt, 1H, CH(CO)N), 1.42 (s, 9H's, t-butyl).

EXAMPLE 7

17-Ethyl-1,14-dihydroxy-12-[2'-[4''-(N'-t-butoxycarbonyl-L-phenylalanine)amido-3''-methoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared by the method of Example 6 utilizing BOC-L-phenylalanine anhydride.

MASS: (FAB) 1044 (M+ +Li).

EXAMPLE 8

17-Ethyl-1,14-dihydroxy-12-[2'-(4''-acetoxyacetylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg) in dry methylene chloride (0.4 ml) was cooled to 0° C. To this solution was added a solution of acetoxyacetyl chloride (9 mg) in methylene chloride (0.5 ml). The reaction mixture was stirred at 0° C. for 30 minutes, and quenched with a drop of methanol. Purification by preparative tlc on silica gel (1000 microns, 5% i-PrOH/CH$_2$Cl$_2$) gave 36 mg of the title compound.

MASS: (FAB) 891 (M+ +H).

$^1$H NMR: δ6.25 (d, 1H, 4''-NH), 4.52 (s, 2H's, COCH$_2$CO), 2.13 (s, 3H's, COCH$_3$).

EXAMPLE 9

17-Ethyl-1,14-dihydroxy-12-[2'-(4''-1'''-adamantane carboxamido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (35 mg) in dry methylene chloride (0.4 ml) was cooled to 0° C. To this solution was added triethylamine (10 μl) followed by a solution of 1-adamantane carbonyl chloride (9 mg) in methylene chloride (0.1 ml). The reaction mixture was stirred at 0° C. for 20 minutes. The reaction was purified by preparative tlc on silica gel (1000 microns, 5% i-PrOH/CH$_2$Cl$_2$) to give 26 mg of the title compound. (Mass, $^1$H and $^{13}$C data were consistent with the proposed structure).

EXAMPLE 10

17-Ethyl-1,14-dihydroxy-12-[2'-(4''-cyclopropanecarboxamido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 32 mg of 17-ethyl-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (from Example 3) in dry methylene chloride (0.4 ml) was cooled to 0° C. To this solution was added triethylamine (10 μl) followed by a solution of cyclopropane carbonyl chloride (5 mg) in methylene chloride (0.1 ml). The reaction mixture was stirred at 0° C. for 30 min. The reaction mixture was purified by preparative tlc on silica gel (1000 microns, 5% i-PrOH/CH$_2$Cl$_2$) to give 20 mg of the title compound. (Mass, $^1$H and $^{13}$C data were consistent with the proposed structure).

EXAMPLE 11

17-Ethyl-1,14-dihydroxy-12-[2-(4'''-formamido-3'''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The compound 17-ethyl-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (30 mg) was mixed with methyl formate (0.5 ml) and stirred at 0° C. for 1 hr. The reaction mixture was allowed to warm to room temperature and then stirred overnight. The excess methylformate was removed with nitrogen flow and the crude mixture was purified by preparative tlc on silica gel (1000 microns, 5% i-PrOH/CH$_2$Cl$_2$) to give 25 mg of the title compound. (Mass, $^1$H and $^{13}$C data were consistent with the proposed structure).

EXAMPLE 12

17-Ethyl-1,14-dihydroxy-12-{2'-[4'''',5''''-dicarboethoxy-1''',2''',3'''-triazole)-3''-methoxycyclohexyl]-1'-methylvinyl}-23,25-dimethoxy-13,19,21,27-tetramethyl-11,28-dioxa-4-azatricyclo[22.3.1.0$^{4,9}$]octacos-18-ene-2,3,10,16-tetraone A mixture of 17-ethyl-1,14-dihydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (20 mg) in neat diethylacetylene dicarboxylate (0.1 ml) was stirred at room temperature overnight. The cycloaddition product was isolated by preparative tlc on silica gel (1000 microns, 5% i-PrOH/CH$_2$Cl$_2$) to give 20 mg of the title compound.

MASS: (FAB) 993 (M+ +Li).

EXAMPLE 13

17-Ethyl-1-hydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 500 mg of 17-ethyl-1,14-dihydroxy-12-[2'-(4''-hydroxy-3-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in 7 ml of benzene was treated with 10 mg of p-toluenesulfonic acid and the solution was heated at 60° C. for two hours. The reaction mixture was quenched into saturated sodium bicarbonate solution and extracted with ethyl acetate. Combined organic layers were washed with water and saturated sodium chloride solution. The organic solution was dried with anhydrous magnesium sulfate and concentrated. The residue was flash chromatographed on silica gel (66% ethyl acetate: 33% hexane: 1% methanol) to give 350 mg of product. This material was dissolved in 10 ml of ethyl acetate and treated with 15 mg of 5% Rh/C. A balloon with hydrogen was placed over the reaction mixture and the mixture stirred until the reaction was complete. The mixture was filtered through diatomaceous earth, concentrated and the residue subjected to flash chromatography (75% CH$_2$Cl$_2$: 5% MeOH: 20% Hexane) to give 294 mg of product. A solution of 61 mg of this material, diisopropylethyl anine (33 μl) and N, N-dimethylaminopyridine (23.2 mg) in 2 ml of methylene chloride was treated with 35.4 mg of o-nitrobenzenesulfonyl chloride under nitrogen. The reaction mixture was stirred for 4.5 hours and then diluted with aqueous sodium bicarbonate solution. The mixture was repeatedly extracted with ethyl acetate. The combined organic layers were then dried with anhydrous magnesium sulfate, concentrated and flash chromatograped on silica gel to afford 72.5 mg of product. This material was dissolved in 1.1 ml of DMF and then treated with sodium azide (24.4 mg). The reaction mixture was stirred at 80° C. under nitrogen for 4 hours and then diluted with water. The mixture was extracted with ethyl acetate and the combined fractions were washed with water, brine, dried with anhydrous magnesium sulfate and concentrated. The residue was purified by preparative TLC (66% ethyl acetate: 33% hexane: 1% MeOH) to give 28 mg of azide. A solution of this azide (23 mg) in 0.5 ml of wet toluene containing 7.8 mg of triphenylphosphine was heated at 70° C. for 17 hours. The reaction mixture was subjected to preparative TLC (88% CH$_2$Cl$_2$: 10% MeOH: 2% NH$_4$OH) to give 9 mg of the title compound.

MASS: (FAB) 775 (M+).

EXAMPLE 14

17-Ethyl-1,14-dihydroxy-12-{2'-[4''-(o-nitrobenzenesulfonyl)-3''-hydroxycyclohexyl]-1'-methylvinyl}-23,25-dimethoxy-13,19,21,27-tetramethyl-11,28-dioxa-4-azatricyclo[22.3.1.0$^{4,9}$]octacos-18-ene-2,3,10,16-tetranone and 17-Ethyl-1,14-dihydroxy-12-{2'-[4''-hydroxy-3''-(o-nitrobenzenesulfonyl)cyclohexyl]-1'-methylvinyl}-23,25-dimethoxy-13,19,21,27-tetramethyl-11,28-dioxa-4-azatricyclo[22.3.1.0$^{4,9}$]octacos-18-ene-2,3,10,16-tetraone To a cooled solution (0° C.) of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (787mg) in dry methylene chloride (15 ml) is added diisopropylethyl amine (492.4 mg) followed by o-nitrobenzenesulfonyl chloride (281 mg) and a catalytic amount of N,N-dimethylaminopyridine. The yellow solution is stirred at room temperature under a nitrogen atmosphere for 3 hr., and then quenched with sat'd aqueous sodium bicarbonate. Organic layer is washed (water, sat'd NaHCO$_3$, sat'd NaCl), dried (anhydrous Na$_2$SO$_4$) and the solvent is removed in vacuo. Chromatography on silica gel gives the title compounds.

EXAMPLE 15

17-Ethyl-1,14-dihydroxy-12-[2'-(4''-azido-3''-hydroxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a stirred solution of 17-ethyl-1,14-dihydroxy-12-{2'-[4''-(o-nitrobenzenesulfonyl)-3''-hydroxycyclohexyl]-1'-methylvinyl}-23,25-dimethoxy-13,19,21,27-tetramethyl-11,28-dioxa-4-azatricyclo[22.3.1.0$^{4,9}$ ]octacos-18-ene-2,3,10,16-tetraone (87 mg) in dry dimethylformamide (1 ml) is added sodium azide (16.7 mg) in one portion. The reaction is heated at 80° C. under nitrogen atmosphere for 3 hr. The reaction mixture is cooled, poured into water (5 ml) and extracted with ethyl acetate. Normal work-up followed by preparative tlc on silica gel gives the title compound.

EXAMPLE 16

17-Ethyl-1,14-dihydroxy-12-[2'-(4''-hydroxy-3''-azidocyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone The title compound is prepared by the method of Example 15 utilizing 17-ethyl-1,14-dihydroxy-12-{2'-[-4''-hydroxy-3''-(o-nitrobenzenesulfonyl)cyclohexyl]-1'-methylvinyl}-23,25-dimethoxy-13,19,21,27-tetramethyl-11,28-dioxa-4-azatricyclo[22.3.1.0$^{4,9}$]-octacos-18-ene-2,3,10,16-tetraone.

EXAMPLE 17

17-Ethyl-1,14-dihydroxy-12-[2'-(4''-amino-3''-hydroxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone A solution of 17-ethyl-1,14-dihydroxy-12-[2'-(4''-azido-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (28 mg) and triphenylphosphine (9 mg) in 1 ml of wet toluene is stirred at 70° C. overnight. The solvent is removed under reduced pressure, and the residue is purified by preparative tlc on silica gel to give the title compound.

EXAMPLE 18

17-Ethyl-1,14-dihydroxy-12-[2'-(4''-hydroxy-3''-aminocyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone The title compound is prepared by the method of Example 17 utilizing 17-ethyl-1,14-dihydroxy-12-[2'-(4''-hydroxy-3''-azidocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

EXAMPLE 19

17-Ethyl-1-hydroxy-12-[2'-(3''-methoxy-4''-oxocyclohexyl)-1'-methylvinyl]-14-triisopropylsilyloxy-23,25-dimethoxy-13,19,21,27-tetramethyl-11,28-dioxa-4-azatricyclo[22.3.1.0$^{4,9}$]octacos-18-ene-2,3,10,16-tetraone To a cooled solution (−78° C.) of oxalyl chloride (1.5 ml of 2M solution in CH$_2$Cl$_2$) was added dimethyl sulfoxide (361 mg) dropwise, followed by a solution of 17-ethyl-1-hydroxy-12-[2'-(4''-hydroxy-3''-methoxycyclohexyl)-1'-methylvinyl]-14-triisopropylsiloxy-23,25-dimethoxy-13,19,21,27-tetramethyl-11,28-dioxa-4-azatricyclo[22.3.1.0$^{4,9}$]octacos-18-ene-2,3,10,16-tetraone (947 mg) in dry methylene chloride (3 ml). The reaction mixture was stirred for 30 min. at −78° C. and then triethylamine (1 ml) was added. The reaction temperature was raised to room temperature, reaction was poured into water (20 ml), and extracted with ethyl acetate (three times). Combined organic layers were washed (water, sat'd NaHCO$_3$), dried (anhydrous Na$_2$SO$_4$), and filtered. Removal of solvent followed by purification (silica gel column chromatography, 40% ethyl acetate: 60% hexane) gave 870 mg of the title compound.

EXAMPLE 20

17-Ethyl-1,14-dihydroxy-12-[2'-(3''-methoxy-4''-oxocyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a stirred solution of 17-ethyl-1-hydroxy-12-[2'-(3''-methoxy-4''-oxocyclohexyl)-1'-methylvinyl]-14-triisopropylsilyloxy-23,25-dimethoxy-13,19,21,27-tetramethyl-11,28-dioxa-4-azatricyclo[22.3.1.0$^{4,9}$]-octacos-18-ene-2,3,10,16-tetraone from Example 19 (870 mg) in acetonitrile (20 ml) was added hydrofluroic acid (48%, 1 ml) at room temperature. The reaction progress was monitored by tlc analysis and after 4 hr. the reaction mixture was quenched with sat'd aqueous sodium bicarbonate. The organic layer was separated and the aqueous layer was extracted with ethyl acetate three times. Combined organic layers were washed (sat'd NaHCO$_3$, sat'd NaCl), dried (anhydrous Na$_2$SO$_4$), and filtered. Removal of solvent followed by purification (silica gel column chromatography, 50% ethyl acetate/hexane) gave 600 mg of the title compound.

EXAMPLE 21

17-Ethyl-1,14-dihydroxy-12-[2'-(4''-benzylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-]2'-(3''-methoxy-4''-oxocyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone from Example 20 (79.7 mg) in dry isopropyl alcohol (3 ml) is added benzyl amine (86.5 mg). The mixture is stirred at r.t. for 30 min., and cooled to −78° C. To this solution is added a solution of sodium cyanoborohydride (6.7 mg) in isopropyl alcohol (0.5 ml). The reaction is stirred at −78° C. and poured into ice water. Extraction with ethyl acetate, followed by purification gives the title compound as a mixture of epimers at C-4''.

EXAMPLE 22

17-Ethyl-1-hydroxy-12-[2'-(4''-trimethylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Iodide 17-Ethyl-1-hydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, from Example 13, was dissolved in absolute ethanol in a heavy walled glass tube. Methyl iodide (large excess) and NaHCO$_3$ was added, the tube was sealed, and the tube was heated. Progress of the reaction was followed by watching disappearance of the starting amine on thin layer chromatography and the appearance of a more polar new spot. Upon completion of reaction, the quaternary iodide was obtained by evaporation of excess methyl iodide and solvent.

EXAMPLE 23

17-Ethyl-1,2,14-trihydroxy-12-[2'-(4''-acetylamino-3''-methoxycyclohexyl)-1'-methylvinyl]-23,25-dimethoxy-13,1927-tetramethyl-11,28-dioxa-4-azatricyclo[22.3.1.0$^{4,9}$]octacos-18-ene-3,10,16-trione To a suspension of samarium (63 mg) in dry THF (1 ml) is added a solution of diiodoethane (56 mg in 1 ml THF) at r.t., and stirred for 1 hr. The dark blue solution is cooled to −78° C., and to this mixture is added a solution of 17-ethyl-1,14-dihydroxy-12-[2'-(4''-acetylamino-3''-methoxycyclohexyl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,16-tetraone (166 mg, Example 4) in 50% THF/MeOH (3 ml). The reaction is stirred for −78° C. for 10 minutes., allowed to warm to room temperature over a period of 10 min., and then quenched with saturated potassium carbonate solution. The organic layer is extracted with ether/ethyl acetate, washed (sat'd NaCl), and dried (anhydrous Na$_2$SO$_4$). Removal of solvent followed by chromatography on silica gel gives the title compound.

EXAMPLE 24

17-Ethyl-1,14-dihydroxy-12-[2'-(4''-oxadecahydroquinol-2-on-6''-yl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a cooled (0° C.) solution of 17-ethyl-1,14-dihydroxy-12-[2'-(4''-amino-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (77 mg) in methylene chloride (5 ml) is added triethylamine (20 μl) followed by a solution of chloroacetyl chloride (12 mg) in methylene chloride (1 ml). The reaction temperature is raised to room temperature and the reaction is stirred until all the starting material is consumed. The reaction is quenched with water, extracted with ethyl acetate, and the combined organic layers are dried (anhydrous sodium sulfate). Removal of solvent gives the crude chloroacetylamide. To a solution of this crude compound in dry ethanol (2 ml) is added a solution of sodium ethoxide in ethanol (5 ml, 0.1 mmole) and the solution is stirred at room temperature. The reaction is quenched with sat'd ammonium chloride solution and concentrated under reduced pressure. Purification of the residue via preparative tlc on silica gel gives the title compound.

EXAMPLE 25

17-Ethyl-1,14-dihydroxy-12-[2'-(4''-oxadecahydroquinol-2-on-7''-yl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound is prepared by the method of Example 24 utilizing 17-ethyl-1,14-dihydroxy-12-[2'-(3''-amino-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as a starting material.

EXAMPLE 26

17-Ethyl-1,14-dihydroxy-12-{2'-[4''-(N'-phenylaminocarbonyl)amino-3''-methoxycyclohexy]-1'-methylvinyl}-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg) in methylene chloride (2 ml) is added phenyl isocyanate (12 mg) at 0° C. with stirring. The reaction mixture is warmed to room temperature and the reaction progress is followed by tlc analysis. The reaction mixture is concentrated under a stream of nitrogen and purified by preparative tlc on silica to give the title compound.

EXAMPLE 27

17-Ethyl-1,14-dihydroxy-12-{2'-[4''-(ethoxycarbonyl)amino-3''-methoxycyclohexyl]-1'-methylvinyl}-23,25-dimethoxy-13,19,21,27-tetramethyl-11,28-dioxa-4-azatri-cyclo[22.3.1.0$^{4,9}$]octacos-18-ene-2,3,10,16-tetraone To a solution of 17-ethyl-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg) in methylene chloride (2 ml) was added triethylamine (10 μl), followed by ethyl chloroformate (15 μl) at 0° C. with stirring. The reaction mixture was warmed to room temperature and the reaction progress was followed by tlc analysis. The solution was quenched with a drop of methanol and purified by preparative tlc on silica (5% iPA/CH$_2$Cl$_2$) to give 38 mg of the title compound.

MASS:(FAB) 863 (M+ +H).

EXAMPLE 28

17-Ethyl-1-hydroxy-12-{2'-[4''-(acetylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-{2'-(4''-amino-3''-methoxycyclohexyl)-1'-methylvinyl]-23,25-dimethoxy-13,19,21,27-azatricyclo[22.3.1.0$^{4,9}$]octacos-18-ene-2,3,10,16-tetraone (60 mg) from Example 13 in dry CH$_2$Cl$_2$ (0.5 ml) is added Et$_3$N (20 μl) followed by a solution of acetic anhydride (20 mg in 1 ml) as described in Example 4. Work-up and purification on silica gel affords the title compound.

EXAMPLE 29

17-Ethyl-1,14-dihydroxy-12-[2'-(4''-amino-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (145 mg) (Example 56) in dry methylene chloride (4 ml) was added an excess of 2,6-lutidine (62 μl) and the mixture was stirred at room temperature. After 10 minutes, tert-butyldimethylsilyl trifluoromethanesulfonate (81 μl) was added via syringe. After 15 minutes the reaction mixture was diluted with ethyl acetate, extracted with saturated sodium bicarbonate, washed with brine and the organic phase dried over magnesium sulfate. Removal of the solvent in vacuo and flash chromatography on silica gel (ethyl acetate:hexane (1:2)+1% methanol) gave the bis-protected compound (130 mg). To a solution of this compound in acetonitrile (4 ml) was added a solution of 2% HF in aqueous acetonitrile (70 μ), and the mixture stirred at room temperature. After 5.5 hours, the solution was diluted with ethyl acetate, extracted with saturated sodium bicarbonate solution and the organic phase dried over magnesium sulfate. Purification of the concentrate by flash chromatography on silica gel (ethyl acetate:hexane (1:2)+1% methanol) gave the mono-protected compound (80 mg). To a solution of this compound in dry methylene chloride (1 ml) was added an excess of diisopropylethylamine (36 μl) and o-nitrophenylsulfonyl chloride (39 mg) followed by addition of 4-dimethylaminopyridine (22 mg). The mixture was stirred at room temperature for 5 hours at which time it was diluted with ethyl acetate, extracted from half saturated sodium bicarbonate solution and washed with brine. The combined organics were dried over magnesium sulfate and the concentrate purified by flash chromatography on silica gel (ethyl acetate:hexane (1:2)+1% methanol) to give product (87 mg). To a solution of this compound in N,N-dimethylformamide (1 ml) was added an excess of sodium azide (25 mg) and the mixture heated to 70° C. After 7.5 hours the reaction mixture was cooled to room temperature, diluted with ethyl acetate, extracted from half-saturated ammonium chloride, and washed with brine. The combined organics were dried over sodium sulfate and purified by flash chromatography on silica gel (ethyl acetate:hexane (1:2)+1% methanol) to give the azide compound (38 mg). To a solution of this protected azide in acetonitrile (1 ml) was added a solution of 2% HF in aqueous acetonitrile (150 μl), and the mixture stirred at room temperature. After 4.5 hours, the solution was diluted with ethyl acetate, extracted with saturated sodium bicarbonate solution and the organic phase dried over magnesium sulfate. Purification of the concentrate by flash chromatography on silica gel (ethyl acetate:hexane (1:2)+1% methanol) gave the deprotected compound (22.5 mg). To a solution of the azido compound in 10% aqueous toluene (0.5 ml) was added triphenylphosphine (10.7 mg) and the mixture heated to 70° C. with stirring. After 18 hours the reaction mixture was cooled, then concentrated to 10% volume in vacuo, and purified by preparative TLC on silica gel (2% ammonium hydroxide, 5% methanol in methylene chloride) to give the title compound (5.5 mg). partial $^1$H NMR δ: 5.19 (brs, 1H); 4.59 (brd, J=4 Hz, 1H); 4.41 (brd, J=14 Hz, 1H); 1.16 (d, J=7 Hz); 1.13 (d, J=7 Hz, 3H).

EXAMPLE 30

17-Ethyl-1-hydroxy-12-[2'-(4''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (158 mg) (Example 55) in dry methylene chloride (3.5 ml) was added an excess of diisopropylethylamine (82 μl) and o-nitrophenylsulfonyl chloride (87 mg) followed by addition of 4-dimethylaminopyridine (58 mg). The mixture was stirred at room temperature for 23 hours at which time it was diluted with ethyl acetate, extracted from saturated sodium bicarbonate solution and washed with brine. The combined organics were dried over magnesium sulfate and the concentrate purified by flash chromatography on silica gel (ethyl acetate:hexane (1:1)+1% methanol) to give the activated compound (130 mg). To a solution of this compound in N,N-dimethylformamide (2 ml) was added an excess of sodium azide (43 mg) and the mixture heated to 70° C. After 4 hours the reaction mixture was cooled to room temperature, diluted with ethyl acetate, extracted from half-saturated ammonium chloride, and washed with brine. The combined organics were dried over magnesium sulfate and purified by flash chromatography on silica gel (ethyl acetate:hexane (1:2)+1% methanol) to give the azido compound (50 mg). To a solution of this compound in 10% aqueous benzene (1.7 ml) was added triphenylphosphine (24 mg) and the mixture heated to 70° C. with stirring. After 17 hours, the reaction mixture is cooled, concentrated to 10% volume in vacuo and applied directly to a column of silica gel for purification by flash chromatography (ethyl acetate:hexane (1:1)+1% methanol then 2% ammonium hydroxide, 5% methanol in methylene chloride) to give the title compound (38 mg).

MASS: (FAB) 802 (M+)

partial $^1$H NMR δ: 4.58 (brs, J=4 Hz, 1H); 4.41 (brd, J=4 Hz, 1H); 3.87 (dd, J=12, 3 Hz, 1H).

EXAMPLE 31

17-Ethyl-1-hydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-14,18-diene-2,3,10,16-tetraone A solution of 17-ethyl-1,14-dihydroxy-12-[2'-(4''-azido-3''-methoxycyclohexyl)-1'-methylvinyl]-23,25-dimethoxy-13,19,21,27-tetramethyl-11,28-dioxa-4-4-azatricyclo[22.3.1.0$^{4,9}$]octacos-18-ene-2,3,10,16-tetraone (210 mg, example 2, step E) and a catalytic amount of p-toluenesulfonic acid in 40 ml of dry benzene was refluxed for 2.5 h under nitrogen atmosphere. The solvent was removed under reduced pressure and the dark brown residue was purified by column chromatography on silica gel (40% ethyl acetate/hexane) to give the title compound.

MASS: (FAB) 799 (M+H).

EXAMPLE 32

17-Ethyl-1-hydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone (55 mg, Example 31), tetrakistriphenylphosphine palladium (10 mg), and acetic acid (10 μl) in 3 ml of dry toluene was stirred for 5 min at room temperature under nitrogen atmosphere. To this yellow solution was added tributyltin hydride (40 μl) and stirred an additional 45 min at room temperature. The brown colored reaction mixture was subjected to column chromatography on silica gel (eluted first with hexane and then with 50% ethyl acetate/hexane) to give 50 mg of the title compound (Mass and $^1$H NMR data were consistent with the proposed structure).

EXAMPLE 33

17-Ethyl-1,14-dihydroxy-12-[2'-(4"-acetamidine-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of ethyl acetamidate hydrochloride (6.3 mg) in 500 µl of dimethylacetamide (DMAC) was added 9 µl of diisopropylethylamine and stirred at 0° C. until the solution became clear. This solution was added to a solution of 17-ethyl-1,14-dihydroxy-12-[2'-(4"-amino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg, Example 3) in 500 µl of DMAC at −10° C. The reaction temperature was gradually raised to room temperature and the reaction progress was monitored by tlc analysis. After stirring 2 h at room temperature, 100 µl of trifluoroacetic acid (TFA) was added and the product was isolated by tritiation with water as a TFA salt.

MASS: (FAB) 832 (M+H-TFA).

EXAMPLE 34

17-Ethyl-1-hydroxy-12-[2'-(4"-benzamidine-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-(4"-amino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg, example 13) and methyl benzimidate hydrochloride (11 mg) in 500 µl of DMAC was cooled to 0° C. To this solution was added 30 µl of diisopropylethylamine under nitrogen atmosphere. The reaction temperature was raised to room temperature and stirring was continued for additional 2 h at this temperature. TFA (100 µl) was added and the product was isolated by tritiation with water as a TFA salt.

MASS: (FAB) 864 (M+H-TFA).

EXAMPLE 35

17-Ethyl-1-hydroxy-12-[2'-[4"-formamidine-3"-methoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-(4"-amino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (35 mg, example 13) in 500 µl of dry DMAC was cooled to −10° C. To this solution was added a freshly prepared benzyl formimidate hydrochloride (10 mg) followed by diisopropylethylamine (27 µl) and the mixture was stirred under nitrogen atmosphere. The reaction temperature was raised to room temperature and stirred at this temperature for 2 h. During that time all of the starting material was converted to the product. TFA was added (200 µl) and the product was isolated by trituration with water as a TFA salt.

EXAMPLE 36

17-Ethyl-1-hydroxy-12-[2'-(4"'-methylcarbamate-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4"-amino-3"-methoxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone (37 mg, Example 13) in dry methylene chloride (500 µl) was added diisopropylethylamine (15 µl) followed by methyl chloroformate (5 µl) under nitrogen atmosphere. The reaction mixture was stirred at room temperature for 15 min, then quenched with methanol. The crude material was purified by preparative tlc on silica gel (5% MeOH/CH$_2$Cl$_2$) to give 36 mg of the title compound.

MASS: (FAB) 871 (M+Na).

EXAMPLE 37

17-Ethyl-1-hydroxy-12-[2'-(4"-benzylcarbamate-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 7-ethyl-1-hydroxy-12-[2'-(4"-amino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg, Example 13) in dry methylene chloride (500 µl) was added diisopropylethylamine (24 µl) followed by benzyl chloroformate (17 µl) under nitrogen atmosphere. The reaction mixture was stirred at room temperature for 30 min, then quenched with methanol. The crude material was purified by preparative tlc on silica gel (5% MeOH/CH$_2$Cl$_2$) to give 28 mg of the title compound.

MASS: (FAB) 847 (M+Na).

EXAMPLE 38

17-Ethyl-1-hydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1,14-dihydroxy-12-[2'-(3",4'-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (210 mg) and a catalytic amount of p-toluenesulfonic acid in 40 ml of dry benzene was refluxed for 4 h under nitrogen atmosphere. The solvent was removed under reduced pressure and the dark brown residue was purified by column chromatography on silica gel (7% i-PrOH/CH$_2$Cl$_2$) to give 17-ethyl-1-hydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone (180 mg) as a white solid. This material was dissolved in ethanol (20 ml) and treated with 5% Rh/C (40 mg). Hydrogen was introduced via balloon for 30 min and the mixture was filtered through celite. Removal of the solvent followed by column chromatography on silica gave 172 mg of the title compound (Mass, $^1$H and $^{13}$C NMR data were consistent with the desired structure).

EXAMPLE 39

17-Ethyl-1-hydroxy-12-[2'-[4''-(2'''-nitrobenzenesulfonyloxy)-3''-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (A) and 17-Ethyl-1-hydroxy-12-[2'-[3''-(2'''-nitrobenzenesulfonyloxy)-4''-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (B)

To a solution of 17-ethyl-1-hydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg, Example 38) in dry methylene chloride (20 ml) was added diisopropylethylamine (150 μl) followed by 2-nitrobenzenesulonyl chloride (60 mg), then 4-dimethylaminopyridine (27 mg). The yellow solution was stirred at room temperature under nitrogen atmosphere for 4 h, then quenched with sat'd aqueous sodium bicarbonate solution. The organic layer was washed (water, sat'd NaHCO$_3$, sat'd NaCl), dried (anhydrous Na$_2$SO$_4$) and the solvent was removed in vacuo. Chromatography on silica gel (2:1 ethyl acetate/hexane) gave 70 mg of the title compound A and 60 mg of the title compound B (Mass, $^1$H and $^{13}$C NMR data were consistent with the structures).

EXAMPLE 40

17-Ethyl-1-hydroxy-12-[2'-(3''(R),4''(S)-epoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-[4''-(2'''-nitrobenzenesulfonyloxy)-3''-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (60 mg, Compound A, Example 39) in 3 ml of dry methylene chloride was added triethylamine (1 ml) and stirred at room temperature for 3 days. The solvent was removed under reduced pressure and the residue was purified by column chromatography on silica gel (2:3 hexane/ethyl acetate) to give 42 mg of the title compound.

Mass: (FAB) 744 (M+H), 766 (M+Na).

EXAMPLE 41

17-Ethyl-1-hydroxy-12-[2'-(3''(S),4''(R)-epoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared by the method of Example 40 utilizing 17-ethyl-1-hydroxy-12-[2'-[3''-(2'''-nitrobenzenesulfonyloxy)-4''-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (Example 39, compound B) as starting material.

EXAMPLE 42

17-Ethyl-1-hydroxy-12-[2'-(4'''-azido-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3''(R),4''(S)-epoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg, Example 40) in ethanol (5 ml) was added a mixture of sodium azide (100 mg) and ammonium chloride (14 mg) in warm water (250 μl). The reaction mixture was heated at 60° C. for 4 h in an oil bath and cooled to room temperature. Removal of solvent in vacuo followed by chromatography on silica gel (60% ethyl acetate/hexane) gave 132 mg of the title compound.

IR: 2100 cm$^{-1}$ (N$_3$).

EXAMPLE 43

17-Ethyl-1-hydroxy-12-[2'-(3''-azido-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared by the method of Example 42 utilizing 17-ethyl-1-hydroxy-12-[2'-(3''(S),4''(R)-epoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (Example 41) as starting material.

EXAMPLE 44

17-Ethyl-1-hydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A suspension of 17-ethyl-1-hydroxy-12-[2'-(4''-azido-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (20 mg, Example 42)) and silver oxide (20 mg) in 1.5 ml of methyl iodide was refluxed in a gas-tight bottle for 4 days. The yellow solid was filtered off and the excess methyl iodide was removed. Purification of crude material by preparative tlc on silica gel (1:1 hexane/ethyl acetate) gave 4 mg of the title compound.

Mass: (FAB) 807 (M+Li).

EXAMPLE 45

17-Ethyl-1-hydroxy-12-[2'-(4''-alpha-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-(4''-alpha-azido-3''-methoxycyclohexyl)-1'-methylvinyl]-23,25-di-methoxy-13,19,21,27-tetramethyl-11,28-dioxa-4-azatricyclo[22.3.1.0$^{4,9}$]octacos-18-ene-2,3,10,16-tetraone (20 mg, Example 44) and triphenylphosphine (7 mg) in 3 ml of 10% water/benzene was refluxed for 16 h in an oil bath. The solvent was removed in vacuo and the crude material was purified by column chromatography on silica gel (eluted first with 5% MeOH/CH$_2$Cl$_2$, then 1% NH$_4$OH in 5% MeOH/CH$_2$Cl$_2$) to give 12 mg of the title compound.

Mass: (FAB) 775 (M+H), 799 (M+Na).

EXAMPLE 46

17-Ethyl-1-hydroxy-12-[2'-(4''-hydroxy-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg, Example 38) in ether (6 ml) is added borontrifluoride etherate (10 μl) followed by freshly prepared diazoethane (100 fold excess). The mixture is stirred at room temperature for 15 min and quenched with sat'd aqueous sodium bicarbonate solution. The organic layer is separated, washed (sat'd aqueous NaCl) and dried over anhydrous magnesium sulfate. Removal of solvent followed by preparative tlc on silica to separate the regioisomers gives the title compound.

EXAMPLE 47

17-Ethyl-1-hydroxy-12-[2'-[4''-(2'''-nitrobenzenesulfonyloxy)-3''-ethoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-hydroxy-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg, Example 46) in dry methylene chloride (2 ml) is added diisopropylethylamine (150 μl) followed by 2-nitrobenzenesulonyl chloride (60 mg), then 4-dimethylaminopyridine (27 mg). The yellow solution is stirred at room temperature under nitrogen atmosphere for 4 h, then quenched with sat'd aqueous sodium bicarbonate solution. The organic layer is washed (water, sat'd NaHCO$_3$, sat'd NaCl), dried (anhydrous Na$_2$SO$_4$) and the solvent is removed in vacuo. Chromatography on silica gel gives the title compound.

EXAMPLE 48

17-Ethyl-1-hydroxy-12-[2'-[4''-azido-3''-ethoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1-hydroxy-12-[2'-[4''-(2'''-nitrobenzenesulfonyloxy)-3''-ethoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (87 mg, Example 47) in dry DMF (1 ml) is added sodium azide (16.7 mg) in one portion. The reaction is heated at 80° C. under nitrogen atmosphere for 3 h. The reaction mixture is cooled, poured into water (5 ml) and extracted with ethyl acetate. Normal work-up followed by preparative tlc on silica gel gives the title compound.

EXAMPLE 49

17-Ethyl-1-hydroxy-12-[2'-[4''-amino-3''-ethoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-[4''-azido-3''-ethoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (28 mg, Example 48) and triphenylphosphine (9 mg) in 1 ml of wet benzene is refluxed overnight. The solvent is removed in vacuo and the residue is purified on silica gel column to give the title compound.

EXAMPLE 50

17-Ethyl-1-hydroxy-12-[2'-(4''-hydroxy-3''-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg, Example 38) in ether (6 ml) is added borontrifluoride etherate (10 μl) followed by freshly prepared 1-diazopropane (100 fold excess). The mixture is stirred at room temperature for 15 min and quenched with sat'd aqueous sodium bicarbonate solution. The organic layer is separated, washed (sat'd aqueous NaCl) and dried over anhydrous magnesium sulfate. Removal of solvent followed by preparative tlc on silica gives the title compound.

EXAMPLE 51

17-Ethyl-1-hydroxy-12-[2'-[4''-amino-3''-n-propyloxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-hydroxy-3''-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (130 mg, Example 50) in dry methylene chloride (2 ml) was added diisopropylethylamine (67 μl) followed by 2-nitrobenzenesulonyl chloride (72 mg), then 4-dimethylaminopyridine (47 mg). The yellow solution was stirred at room temperature under nitrogen atmosphere for 16 h, then quenched with sat'd aqueous sodium bicarbonate solution. The organic layer is washed (water, sat'd NaHCO$_3$, sat'd NaCl), dried (anhydrous Na$_2$SO$_4$) and the solvent is removed in vacuo. Chromatography on silica gel gave 17-ethyl-1-hydroxy-12-[2'-[4''-(2'''-nitrobenzenesulfonyloxy)-3''-n-propyloxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as an off-white solid. This off-white solid (111 mg) was dissolved in dry DMF (1 ml) and to this solution was added sodium azide (32 mg) in one portion and heated at 80° C. under nitrogen atmosphere for 5.5 h. The reaction mixture was cooled, poured into water (5 ml) and extracted with ethyl acetate. The combined organic layers were washed with brine, dried over sodium sulfate and purified by column chromatography on silica gel (2:1 ethyl acetate/hexane) to gave 52 mg of 17-ethyl-1-hydroxy-12-[2'-(4''-azido-3''-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. This material (46 mg) and triphenylphosphine (29 mg) in 1 ml of wet benzene was refluxed for 6.5 h. The solvent was removed in vacuo and the residue was purified on silica gel column (eluted first with 5% MeOH/CH$_2$Cl$_2$, then 1% NH$_4$OH in 5% MeOH/CH$_2$Cl$_2$) to give 37 mg of the title compound. MASS: (FAB) 803 (M+H).

EXAMPLE 52

17-Ethyl-1-hydroxy-12-[2'-(3'',4''-dihydroxycyclohexyl)-1'-methylvinyl]-14-tert-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone To a cooled solution (0° C.) of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (500 mg) in dry methylene chloride (10 ml) was added 2,6-lutidine (740 μl) followed by t-butyldimethylsilyltriflate (580 μl) and stirred at room temperature overnight. The reaction was quenched with 1N HCl and extracted with methylene chloride. The combined organic layers were washed (sat'd. NaHCO$_3$ solution and brine), dried (anhydrous magnesium sulfate) and filtered. Evaporation of the solvent gave 680 mg of crude 17-ethyl-1-hydroxy-12-[2'-(3'',4''-di-tert-butyldimethylsilyloxycyclohexyl)-1'-methylvinyl]-14-tert-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone as a light yellow foam. This material (600 mg) was dissolved in methylene chloride (40 ml) and 10% solution of p-toluenesulfonic acid in methanol (40 ml) was added with stirring. After 4 h, the reaction was quenched with sat'd. sodium bicarbonate solution and extracted with ethyl acetate. Normal work-up and removal of solvent followed by purification on silica gel column (7% MeOH/CH$_2$Cl$_2$) gave 420 mg of the title compound as a white solid.

EXAMPLE 53

17-Ethyl-1-hydroxy-12-[2'-[4''-(2'''-nitrobenzenesulfonyloxy)-3''-hydroxycyclohexyl]-1'-methylvinyl]-14-tert-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone (A)
and
17-Ethyl-1-hydroxy-12-[2'-[3''-(2'''-nitrobenzenesulfonyloxy)-4''-hydroxycyclohexyl]-1'-methylvinyl]-14-tert-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone (B)

The title compounds were prepared by the method of Example 39 utilizing 17-ethyl-1-hydroxy-12-[2'-(3'',4''-dihydroxycyclohexyl)-1'-methylvinyl]-14-tert-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone (Example 52) as a starting material.

EXAMPLE 54

17-Ethyl-1-hydroxy-12-[2'-[4''-alpha-amino-3''-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-[4''-(2'''-nitrobenzenesulfonyloxy)-3''-hydroxycyclohexyl]-1'-methylvinyl]-14-tert-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone (120 mg, Example 53, compound A) in methylene chloride (5 ml) with triethylamine (1 ml) was stirred at room temperature. After 18 h, the solvent was removed and the yellow residue was purified by column chromatography on silica gel (3:2 hexane/ethyl acetate) to give 17-ethyl-1-hydroxy-12-[2'-[3''(R),4''(S)-epoxycyclohexyl]-1'-methylvinyl]-14-tert-butyldimethylsilyloxy-23,25-dimethoxy-13,19,21,27-tetramethyl-11,28-dioxa-4-aza-tricyclo[22.3.1.0$^{4,9}$]octacos-18-ene-2,3,10,16-tetraone (105 mg) as a white solid. This solid (100 mg) was dissolved in ethanol (4 ml) and to this solution was added a mixture of sodium azide (75 mg) and ammonium chloride (12 mg) in warm water (120 μl). The reaction was refluxed for 3 h and cooled to room temperature. The solvent was removed and the residue was purified by preparative tlc on silica (4:3 hexane/ethyl acetate) to give 17-ethyl-1-hydroxy-12-[2'-(4''-azido-3''-hydroxycyclohexyl)-1'-methylvinyl]-14-tert-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone (80 mg). This material (76 mg) was treated with 5 ml of 10% HF (40% in water)/acetonitrile for 45 min, diluted with ethyl acetate and washed with aqueous sat'd sodium bicarbonate solution and brine. The organic layer was dried (anhydrous MgSO$_4$), filtered and the solvent was removed in vacuo. The crude material was purified by column chromatography on silica gel (1:1 ethyl acetate/hexane) to give 17-ethyl-1-hydroxy-12-[2'-(4''-azido-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as a white solid (65 mg). This material (20 mg) in wet benzene (5 ml) with triphenylphosphine (14 mg) was refluxed for 16 h, concentrated in vacuo and directly chromatographed on silica gel (first eluted with 5% MeOH/CH$_2$Cl$_2$, then 1% NH$_4$OH in 7% MeOH/CH$_2$Cl$_2$) to give 14 mg of the title compound. MASS: (FAB) 791 (M+H).

EXAMPLE 55

17-Ethyl-1-hydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg) in ether (6 ml) is added boron trifluoride etherate (10 μl) followed by freshly prepared 2-diazopropane (100 fold excess). The mixture is stirred at room temperature for 15 min and quenched with sat'd aqueous sodium bicarbonate solution. The organic layer is separated, washed (sat'd. aqueous NaCl) and dried over anhydrous magnesium sulfate. Removal of solvent followed by preparative tlc on silica gives the title compound and its 4''-isomer.

EXAMPLE 56

17-Ethyl-1,14-dihydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg) in ether (6 ml) is added boron trifluoride etherate (10 μl) followed by freshly prepared 2-diazopropane (100 fold excess). The mixture is stirred at room temperature for 15 min and quenched with sat'd. aqueous sodium bicarbonate solution. The organic layer is separated, washed (sat'd. aqueous NaCl) and dried over anhydrous magnesium sulfate. Removal of solvent followed by preparative tlc on silica gives the title compound and its 4"-isomer.

EXAMPLE 57

17-Allyl-1-hydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (800 mg) and a catalytic amount of p-toluenesulfonic acid in 40 ml of dry benzene was refluxed for 1.5 h under nitrogen atmosphere. The solvent was removed under reduced pressure and the dark brown residue was purified by column chromatography on silica gel (eluted with ether) to give 720 mg of 17-allyl-1-hydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone as a white solid. This material (500 mg) was dissolved in dry toluene (30 ml) and to this solution was added tetrakistriphenylphosphine palladium° (50 mg) and acetic acid (50 μl) at room temperature. To this yellow solution was added tri-n-butyltin hydride (200 mg) and the mixture was stirred for 1 h. The Brown colored solution was directly applied to column chromatography on silica gel (first eluted with hexane, then with ether) to give 380 mg of the title compound.

MASS: (FAB) 788 (M+H), 810 (M+Na).

EXAMPLE 58

17-Allyl-1-hydroxy-12-[2'-(4"-amino-3"-methoxycyclohexyl)-1'-methylvinyl]-14-t-butyldimethyl-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-allyl-1-hydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (176 mg, Example 57) in dry methylene chloride (10 ml) is added diisopropylethylamine (117 μl) followed by 2-nitrobenzenesulfonyl chloride (104 mg), then 4-dimethylaminopyridine (55 mg). The yellow solution is stirred at room temperature under nitrogen atmosphere for 5 h, then quenched with sat'd. aqueous sodium bicarbonate solution. The organic layer is washed (water, sat'd. NaHCO$_3$, sat'd. NaCl), dried (anhydrous Na$_2$SO$_4$) and the solvent is removed in vacuo. Chromatography on silica gel gave 17-allyl-1-hydroxy-12-[2'-[4"-(2'''-nitrobenzenesulfonyloxy)-3"-methoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as an off-white solid (120 mg). This off-white solid (100 mg) was dissolved in dry DMF (1 ml) and to this solution was added sodium azide (33 mg) in one portion and heated at 80° C. under nitrogen atmosphere for 5.5 h. The reaction mixture was cooled, poured into water (5 ml) and extracted with ethyl acetate. The combined organic layers were washed with brine, dried over sodium sulfate and purified by column chromatography on silica gel (1:1 ethyl acetate/hexane) to give 17-allyl-1-hydroxy-12-[2'-(4"-azido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (66 mg). This material (60 mg) and triphenylphosphine (19 mg) in wet benzene (2 ml) was refluxed for 6.5 h. The solvent was removed in vacuo and the residue was purified on silica gel (eluted first with 5% MeOH/CH$_2$Cl$_2$, then 1% NH$_4$OH in 5% MeOH/CH$_2$Cl$_2$) to give 36 mg of the title compound.

MASS: (FAB) 787 (M+H).

EXAMPLE 59

17-Ethyl-1,14-dihydroxy-12-[2'-(4"-trimethylamino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone iodide A supension of 17-ethyl-1,14-dihydroxy-12-[2'-(4"-amino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (30 mg, Example 3) and sodium bicarbonate (10 mg) in 0.5 ml of methyl iodide was stirred in a gas-tight bottle for 27 h. The solid was filtered off and the excess methyl iodide was removed. Tritiation of crude material with ether gave 30 mg of the title compound as an off-white solid.

MASS: (FAB) 833 (M-127).

EXAMPLE 60

17-Ethyl-1,14-dihydroxy-12-[2'-(4"-L-phenyl alanineamido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone 17-Ethyl-1,14-dihydroxy-12-[2'-[4"-(N'-t-butoxy-carbonyl-L-phenylalanine)amido-3"-methoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (50 mg, Example 7) was placed in a small flask and cooled to −15° C. in an ice-acetone bath. To this cooled solution was added TFA (300 μl) and stirred at this temperature. After 30 min, the reaction mixture was cooled to −78° C. and freeze-dried to give the yellow solid. Purification of the crude material by preparative tlc on silica gel (1% NH$_4$OH in 5% i-PrOH/CH$_2$Cl$_2$) gave 34 mg of the title compound.

MASS: (FAB) 938 (M+H).

EXAMPLE 61

17-Ethyl-1,14-dihydroxy-12-[2'-(4"-D-phenyl alanineamido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared by the method of Example 60 utilizing 17-ethyl-1,14-dihydroxy-12-[2'-[4"-(N'-t-butoxy-carbonyl-D-phenylalanine)amido-3"-methoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (Example 6) as starting material.

EXAMPLE 62

17-Ethyl-1-hydroxy-12-[2'-[4''-(2'''-hydroxypropyl)amino-3''-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (52 mg, Example 13) in dry methanol (1 ml) was added a large excess of propylene oxide (200 μl) followed by a catalytic amount of p-toluenesulfonic acid at room temperature. After stirring at this temperature for 20 h, the solution was concentrated and purified by preparative tlc on silica gel (1% NH$_4$OH in 5% i-PrOH/CH$_2$Cl$_2$) to give 35 mg of the title compound.

MASS: (FAB) 832 (M+H+Li).

EXAMPLE 63

17-Ethyl-1,14-dihydroxy-12-[2'-(4'-azabicyclo[4.1.0]heptane)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1,14-dihydroxy-12-[2'-[4''-azido-3''-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (31 mg, Example 15) in wet toluene (2 ml) with triphenylphosphine (15 mg) was heated to 70° C. After 5 h at this temperature, the solution was concentrated and the crude material was purified on preparative tlc on silica (5% MeOH/CH$_2$Cl$_2$) to give 3.5 mg of the title aziridine.

MASS: (FAB) 765 (M+Li).

EXAMPLE 64

17-Ethyl-1,14-dihydroxy-12-[2'-[4''-(2'''-nitrobenzenesulfonyloxy)-3''-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (A) and 17-Ethyl-1,14-dihydroxy-12-[2'-[3''-(2'''-nitrobenzenesulfonyloxy)-4''-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (B)

To a solution of 17-ethyl-1,14-dihydroxy-12-[2'-(3''',4'''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (389 mg) in methylene chloride (10 ml) was added 2-nitrobenzenesulfonyl chloride (122 mg) and diisopropylethylamine (217 μl) followed by N,N-dimethylaminopyridine (40 mg). The yellow solution was stirred at room temperature for 3 h and quenched with 1N HCl, then extracted with methylene chloride. Normal work-up followed by column chromatography on silica gel (4:1 ethyl acetate/hexane) gave 75 mg of compound A and 45 mg of Compound B.

EXAMPLE 65

17-Ethyl-1,14-dihydroxy-12-[2'-[4''-amino-3''-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1,14-dihydroxy-12-[2'-[4''-(2'''-nitrobenzenesulfonyloxy)-3''-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (105 mg, Example 64, compound A) in dry DMF (1 ml) with sodium azide (22 mg) was heated to 50° C. for 3 h. The reaction mixture was cooled, poured into water and extracted with ethyl acetate. The combined organic layers were washed with brine, dried over sodium sulfate and purified by column chromatography on silica gel (2:1 ethyl acetate/hexane) to gave 32 mg of 17-ethyl-1,14-dihydroxy-12-[2'-(4''-azido-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. This material (30 mg) and triphenylphosphine (15 mg) in 1 ml of wet benzene was refluxed for 6.5 h. The solvent was removed in vacuo and the residue was purified on silica gel (eluted first with 5% MeOH/CH$_2$Cl$_2$, then 1% NH$_4$OH in 5% MeOH/CH$_2$Cl$_2$) to give 12 mg of the title compound.

EXAMPLE 66

17-Ethyl-1,14-dihydroxy-12-[2'-[3''-amino-4''-hydroxycyclohexyl]-1'-methylvinyl](23,25-dimethoxy-13,19,21,27-tetramethyl-11,28-dioxa-4-azatricyclo[22.3.1.0$^{4,9}$]octacos-18-ene-2,3,10,16-tetraone The title compound was prepared by the method of Example 65 utilizing 17-ethyl-1,14-dihydroxy-12-[2'-[3''-(2'''-nitrobenzenesulfonyloxy)-4''-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (Example 64, Compound B) as starting material.

EXAMPLE 67

17-Ethyl-1-hydroxy-12-[2'-(4''-azido-3''-(2,2-dimethoxyethoxy)-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A suspension of 17-ethyl-1-hydroxy-12-[2'-(4''-azido-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (25 mg, Example 42) and silver oxide (25 mg) in 2 ml of bromoacetaldehyde dimethyl acetal is heated at 70° C. for 4 days. The solids are removed by filtration, washed with ethyl acetate, and concentrated in vacuo. The resulting oil is purified by preparative tlc on silica gel to give the title compound.

Alternatively, a solution of 17-ethyl-1-hydroxy-12-[2'-(4''-azido-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (25 mg, Example 42, in 0.2 ml dry DME) is added to a stirring suspension of potassium hydride (1 equivalent in 0.5 ml DME) followed immediately by addition of a large excess of bromoacetaldehyde dimethyl acetal (0.2 ml). After 2 hours the mixture is quenched with saturated ammonium chloride and extracted with ethyl acetate. The combined organics are dried over magnesium sulfate and concentrated in vacuo. The product is purified by preparative tlc on silica gel to give the title compound.

EXAMPLE 68

17-Ethyl-1-hydroxy-12-[2'-(4''-azido-3''-ethanaloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-azido-3''-(2,2-dimethoxyethoxy)-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (10 mg in 1 ml acetone) is added 15 mg of an acidic ion exchange resin (e.g. Amberlyst-15) and the mixture stirred at room temperature. After 4 hours, the suspension is filtered over diatomaceous earth and concentrated in vacuo. The product is purified by preparative TLC on silica gel to give the title compound.

EXAMPLE 69

17-Ethyl-1-hydroxy-12-[2'-(1-aza-4-oxa-bicyclo[4.4.0]dec-1-ene-6-yl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-azido-3''-ethanaloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (5.0 mg in 1 ml benzene), is added distilled water (200 µl) followed by triphenylphosphine (3.0 mg) and the mixture heated to 70° C. on a mantle. After 6 hours, the mixture is diluted with ethyl acetate and the layers separated. The organic portion is concentrated in vacuo and purified by preparative TLC on silica gel to give the title compound.

EXAMPLE 70

17-Ethyl-1-hydroxy-12-[2'-(1-aza-4-oxa-bicyclo[4.4.0]dec-6-yl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(1-aza-4-oxa-bicyclo[4.4.0]dec-1-ene-6-yl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (5 mg in 400 µl tetrahydrofuran) is added acetic acid (10 µl) and the mixture is cooled to −78° C. Potassium triphenylborohydride (26 µl of a 0.5M THF solution) is added and the mixture stirred at −78° C. After 1.5 hours the reaction is quenched by the addition of half-saturated ammonium chloride solution then diluted with ethyl acetate and the layers separated. The organic portion is dried over sodium sulfate and concentrated in vacuo. Purification by preparative TLC on silica gel gives the title compound.

EXAMPLE 71

17-Ethyl-1-hydroxy-12-[2'-(4'-β-benzylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-(4'-β-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (77 mg), benzaldehyde (25 mg) and activated molecular sieves in dry methanol (2 ml) was stirred at room temperature for 3 hr. and to this solution was added acetic acid (10 µl) followed by a solution of sodium cyanoborohydride (350 µl, 0.1 mole solution) in methanol. After stirring at room temperature for 15 min., the solid was filtered off and the solvent was removed in vacuo. The residue was purified by prep tlc on silica gel (60% hexane/ethyl acetate) to give 62 mg of the title compound as a white solid.

MASS: (FAB) 867 (M+H), 873 (M+Li), 889 (M+Na).

EXAMPLE 72

17-Ethyl-1-hydroxy-12-[2'-(4''-β-N,N-dimethylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-(4'-β-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (38 mg), and formaldehyde (100 µl, 37 wt % solution in water) was stirred at room temperature for 30 min. and to this solution was added a drop of acetic acid followed by a solution of sodium cyanoborohydride (100 µl, 0.1 mole solution) in methanol. After stirring at room temperature for 30 min., the solvent was removed in vacuo and the residue was purified by prep tlc on silica gel (5% MeOH in methylene chloride with 1% ammonium hydroxide) to give 24 mg of the title compound as an off white solid.

MASS: (FAB) 803 (M+H).

EXAMPLE 73

A.

17-Ethyl-1,14-dihydroxy-12-[2'-(4''-allyloxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(3''-allyloxy-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg in 1.5 ml 33% methylene chloride in cyclohexane) allyl trichloroacetimidate (53 µl neat) was added and the reagents allowed to mix for 5 minutes. Trifluoromethanesulfonic acid (2 µl neat) was added slowly via syringe and the mixture stirred at room temperature. After 3 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate: hexane (1:1)+1% methanol) gave the title compounds (21 mg 4''-ether; 17 mg 3''-ether).

A. (4"-ether): Partial ¹H NMR δ: 5.93 (m, 1H); 4.87m, 4.19M (brs, 1H); 4.59 (brd J=4.0 Hz, 1H); 4.41 (brd J=14 Hz, 1H); 2.67 (brd J=3.7 Hz, 1H).

B. (3"-ether): Partial ¹H NMR δ: 5.93 (m, 1H); 4.83m, 4.23M (brs, 1H); 4.59 (brd J=4.0 Hz, 1H); 4.41 (brd J=14 Hz, 1H); 2.63 (brs, 1H).

EXAMPLE 74

A.

17-Ethyl-1,14-dihydroxy-12-[2'-(3"-hydroxy-4"-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(4"-hydroxy-3"-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (110 mg in 1.5 ml 33% methylene chloride in cyclohexane) isopropyl trichloroacetimidate (52 μl neat) was added and the reagents allowed to mix for 5 minutes. Trifluoromethanesulfonic acid (2 μl neat) was added slowly via syringe and the mixture stirred at room temperature. After 3 hours the reaction was quenched by the addition of saturated sodium bicarbonate and extracted with ethyl acetate (3×5 ml). The combined organics were washed with brine and dried over magnesium sulfate. Purification of the concentrate by preparative TLC on silica gel (ethyl acetate: hexane (1:1)+1% methanol) gave the title compounds (15 mg 4"-ether; 16 mg 3"-ether).

A. (4"-ether):

MASS: (FAB) 826 (M+Li).

Partial ¹H NMR δ: 5.31 (d J=3.0 Hz,1H); 4.85m, 4.18M (brs, 1H); 4.58 (brd J=4.0 Hz, 1H); 4.40 (brd J=14 Hz, 1H); 2.63(brs, 1H).

B. (3"-ether):

MASS: (FAB) 826 (M+Li).

Partial ¹H NMR δ: 5.32; 5.18m (br d J=3.0 Hz, 1H); 4.82m, 4.21M (brs, 1H); 4.59 (brd, J=4.0 Hz,1H); 4.41 (brd, J=14 Hz, 1H); 2.61(brs, 1H).

EXAMPLE 75

A.

17-Ethyl-1,14-dihydroxy-12-[2'-(4"-sec-butenyloxy-3'-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(3"-sec-butenyloxy-4'-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg in 3 ml 33% methylene chloride in cyclohexane) sec-butenyl trichloroacetimidate (62 μl neat) was added and the reagents allowed to mix for 5 minutes. Trifluoromethanesulfonic acid (2 μl neat) was added slowly via syringe and the mixture stirred at room temperature. After 15 minutes the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:1)+1% methanol) gave the title compounds (11 mg 4"-ether; 13 mg 3"-ether).

A. (4"-ether):

MASS: (FAB) 831 (M+Na).

Partial ¹H NMR δ: 5.65 (m, 1H); 5.32 (brd J=3.0 Hz, 1H); 4.87m, 4.18M (brs, 1H); 4.58 (brd J=4.0 Hz, 1H); 4.41 (brd J=14 Hz, 1H).

B. (3"-ether):

MASS: (FAB) 831 (M+Na).

Partial ¹H NMR δ: 5.65 (m, 1H); 5.31 (brs, 1H); 4.82m, 4.22M (brs, 1H); 4.58 (brd J=4.0 Hz, 1H); 4.41 (brd J=14 Hz, 1H).

EXAMPLE 76

A.

17-Ethyl-1,14-dihydroxy-12-[2'-(4"-(trans-2-butenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(3"-(trans-2-butenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (115 mg in 3 ml 33% methylene chloride in cyclohexane) trans-2-butenyl trichloroacetimidate (48 μl neat) was added and the reagents allowed to mix for 5 minutes. Trifluoromethanesulfonic acid (2 μl neat) was added slowly via syringe and the mixture stirred at room temperature. After 35 minutes the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:1)+1% methanol) gave the title compounds (14 mg 4"-ether; 12 mg 3"-ether).

A. (4"-ether):

MASS: (FAB) 831 (M+Na).

Partial ¹H NMR δ: 5.65(m, 1H); 5.31 (brd J=3.0 Hz, 1H); 4.86m, 4.19M (brs, 1H); 4.59 (brd J=4.0 Hz, 1H); 4.41 (brd J=14 Hz, 1H); 2.68 (brs, 1H).

B. (3"-ether):

MASS: (FAB) 831 (M+Na).

Partial ¹H NMR δ: 5.65 (m,1H); 5.30 (brs, 1H); 4.81m, 4.22M (brs, 1H); 4.59 (brd J=4.0 Hz, 1H); 4.41 (brd J=14 Hz, 1H); 2.64 (brs, 1H).

EXAMPLE 77

A.
17-Ethyl-1,14-dihydroxy-12-[2'-(3"-hydroxy-4"-(3-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.
17-Ethyl-1,14-dihydroxy-12-[2'-(4"-hydroxy-3"-(3-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg in 2 ml methylene chloride) 3-methyl-2-butenyl trichloroacetimidate (39 μl neat) was added and the reagents allowed to mix for 5 minutes. Camphorsulfonic acid (5 mg) was added and the mixture stirred at room temperature. After 21 hours the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:1)+1% methanol) gave the title compounds (24 mg 4"-ether; 21 mg 3"-ether).

A. (4"-ether):
MASS: (FAB) 845 (M+Na).
Partial $^1$H NMR δ: 4.87m, 4.19M (brs, 1H); 4.58 (brd J=4.0 Hz, 1H); 4.41 (brd J=14 Hz, 1H); 2.70 (brs, 1H); 1.75 (s, 3H); 1.67(s, 3H).

B. (3"-ether):
MASS: (FAB) 845 (M+Na).
Partial $^1$H NMR δ: 4.82m, 4.23M (brs, 1H);4.58 (brd J=4.0 Hz, 1H); 4.41 (brd J=14 Hz, 1H); 2.67 (brs, 1H); 1.75 (s,3H); 1.67 (s, 3H).

EXAMPLE 78

A.
17-Ethyl-1,14-dihydroxy-12-[2'-(3"-hydroxy-4"-(2-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.
17-Ethyl-1,14-dihydroxy-12-[2'-(4"-hydroxy-3"-(2-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg in 3 ml 33% methylene chloride in cyclohexane), 2-methylpropenyl trichloroacetimidate (84 μl neat) was added and the reagents allowed to mix for 5 minutes. Trifluoromethanesulfonic acid (2 μl neat) was added slowly via syringe and the mixture stirred at room temperature. After 1 hour the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:1)+1% methanol) gave the title compounds (34 mg 4"-ether; 24 mg 3"-ether).

A. (4"-ether):
MASS: (FAB) 831 (M+Na).
Partial $^1$H NMR δ: 5.32 (brs, 1H); 4.87 (brs, 1H); 4.59 (brs, 1H); 4.41 (brd J=14 Hz, 1H); 4.19M (brs, 1H); 2.60 (brs, 1H); 1.74(s, 3H).

B. (3"-ether):
MASS: (FAB) 831 (M+Na).
Partial $^1$H NMR δ: 5.32 (brs, 1H); 4.87 (brs, 1H); 4.81m, 4.23M (brs, 1H); 2.63 (brs, 1H); 1.74 (s, 3H).

EXAMPLE 79

17-Ethyl-1-hydroxy-12-[2'-(4"-hydroxy-3"-isopropoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a solution of 17-ethyl-1-hydroxy-12-[2'-(3",4"'-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (69 mg in 3 ml 33% methylene chloride in cyclohexane), isopropyl trichloroacetimidate (22 μl neat) was added and the reagents allowed to mix for 5 minutes. Trifluoromethanesulfonic acid (2 μl neat) was added slowly via syringe and the mixture stirred at room temperature. After 24 hours the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:1)+1% methanol) gave the title compound (12 mg).
MASS: (FAB) 803 (M+Li).
Partial $^1$H NMR δ: 4.87 (brd J=10 Hz, 1H); 4.56 (d J=4.0 Hz, 1H); 4.42m, 4.33M (brs, 1H); 2.61 (brs, 1H); 1.16 (d J=7.0 Hz, 6H).

EXAMPLE 80

17-Ethyl-1,14-dihydroxy-12-[2'-(4"-azido-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A: 17-Ethyl-1,14-dihydroxy-12-[2'-(4"-hydroxy-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (616 mg in 12 ml 33% methylene chloride in cyclohexane), isopropyl trichloroacetimidate (244 μl neat) was added and the reagents allowed to mix for 5 minutes. Trifluoromethanesulfonic acid (4 μl neat) was added slowly via syringe and the mixture stirred at room temperature. After 22 hours the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (2:1)+1% methanol) gave the title compound (145 mg 3"-ether).

3"-ether MASS: (FAB) 826 (M+Li).

Partial $^1$H NMR δ: 5.32M, 5.18m (brd J=3 Hz, 1H); 4.82m, 4.21M(brs, 1H); 4.59 (brd J=4 Hz, 1H); 4.41 (brd J=14 Hz, 1H); 3.08 (d J=4 Hz,1H); 2.61 (s, 1H); 1.16 (d J=7 Hz, 6H).

Step B: 17-Ethyl-1-hydroxy-14-(tert-butyldimethylsiloxy)-12-[2'-(4"-(tert-butyldimethylsiloxy)-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (145 mg) in dry methylene chloride (4 ml) was added an excess of 2,6-lutidine (62 μl) and the mixture was stirred at room temperature. After 10 minutes, tert-butyldimethylsilyl trifluoromethanesulfonate (81 μl) was added via syringe. After 15 minutes the reaction mixture was diluted with ethyl acetate, extracted from saturated sodium bicarbonate, washed with brine and the organic phase dried over magnesium sulfate. Removal of the solvent in vacuo and flash chromatography on silica gel (ethyl acetate:hexane (1:2)+1% methanol) gave the title compound (130 mg).

Partial $^1$H NMR δ: 5.48m, 4.18M (brs, 1H); 4.80 (brd J=11 Hz, 1H); 2.78 (dd J=14, 7 Hz).

Step C: 17-Ethyl-1-hydroxy-14-(tert-butyldimethylsiloxy)-12-[2'-(4"-hydroxy-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(tert-butyldimethyl-siloxy)-3"-isopropyloxycyclohexyl)-1'-methylvinyl]-23,25-dimethoxy-13,19,21,27-tetramethyl11,28-dioxa-4-azatricyclo[22.3.1.0$^{4,9}$]octacos18-ene-2,3,10,16-tetraone (130 mg) in acetonitrile (4 ml) was added a solution of 2% HF in aqueous acetonitrile (70 μl), and the mixture stirred at room temperature. After 5.5 hours, the solution was diluted with ethyl acetate, extracted with saturated sodium bicarbonate solution and the organic phase dried over magnesium sulfate. Purification of the concentrate by flash chromatography on silica gel (ethyl acetate: hexane (1:2)+1% methanol) gave the title compound (80 mg).

Partial $^1$H NMR δ: 5.43m, 4.20M (brs, 1H); 5.03 (brd J=11 Hz, 1H); 4.81 (brd J=11 Hz, 1H); 2.78 (dd J=14, 7 Hz, 1H); 2.61 (s, 1H).

Step D: 17-Ethyl-1-hydroxy-14-(tert-butyldimethylsiloxy)-12-[2'-(4"-(o-nitrophenylsulfonyloxy)-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-hydroxy-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (80 mg) in dry methylene chloride (1 ml) was added an excess of diisopropylethyl amine (36 μl) and o-nitrophenylsulfonyl chloride (39 mg) followed by addition of 4-dimethylaminopyridine (22 mg). The mixture was stirred at room temperature for 5 hours at which time it was diluted with ethyl acetate, extracted from half saturated sodium bicarbonate solution and washed with brine. The combined organics were dried over magnesium sulfate and the concentrate purified by flash chromatography on silica gel (ethyl acetate:hexane (1:2)+1% methanol to give the title compound (87 mg).

Partial $^1$H NMR δ: 8.18 (m, 1H); 7.75 (m, 3H); 5.46m, 4.19M (brs, 1H); 4.80 (brd J=11 Hz, 1H); 4.57 (m, 1H); 2.76 (dd J=14, 7 Hz, 1H).

Step E: 17-Ethyl-1-hydroxy-14-(tert-butyldimethylsiloxy)-12-[2'-(4"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(o-nitrophenyl-sulfonyloxy)-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (87 mg) in N,N-dimethyl formamide (1 ml) was added an excess of sodium azide (25 mg) and the mixture heated to 70° C. After 7.5 hours the reaction was cooled to room temperature, diluted with ethyl acetate, extracted from half-saturated ammonium chloride, and washed with brine. The combined organics were dried over sodium sulfate and purified by flash chromatography on silica gel (ethyl acetate:hexane (1:2)+1% methanol) to give the title compound (38 mg).

Partial $^1$H NMR δ: 5.59m, 4.19M (brs, 1H); 4.81 (brd J=11 Hz, 1H); 2.75 (dd J=14, 7 Hz, 1H).

Step F: 17-Ethyl-1,14-dihydroxy-12-(2'-(4"-azido-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tertbutyldimethylsiloxy)-12-[2'-(4"-azido-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (38 mg) in acetonitrile (1 ml) was added a solution of 2% HF in aqueous acetonitrile (150 μl), and the mixture stirred at room temperature. After 4.5 hours, the solution was diluted with ethyl acetate, extracted with saturated sodium bicarbonate solution and the organic phase dried over magnesium sulfate. Purification of the concentrate by flash chromatography on silica gel (ethyl acetate:hexane (1:2)+1% methanol) gave the title compound (22.5 mg).

Partial $^1$H NMR δ: 5.31M, 5.18m (brs, 1H); 4.94m, 4.19M (brs, 1H); 4.59 (brd J=4 Hz, 1H); 4.41 (brd J=14 Hz, 1H); 3.16 (d J=4 Hz, 1H).

EXAMPLE 81

17-Ethyl-1,14-dihydroxy-12-[2'-(4"-amino-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4'-azido-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (22 mg) in 10% aqueous toluene (0.5 ml) was added triphenylphosphine (10.7 mg) and the mixture heated to 70° C. with stirring. After 18 hours, the stir bar was removed and the reaction cooled to room temperature. The mixture was concentrated to 10% volume in vacuo and purified by preparative TLC on silica gel (2% ammonium hydroxide, 5% methanol in methylene chloride) to give the title compound (5.5 mg).

Partial $^1$H NMR δ: 5.31M, 5.19 m (brs, 1H); 4.59 (brd J=4 Hz, 1H); 4.41 (brd J=14 Hz, 1H); 1.16 (d J=7 Hz, 3H); 1.13 (d J=7 Hz, 3H).

EXAMPLE 82

17-Ethyl-1-hydroxy-12-[2'-(4''-azido-3''-isopropyloxy cyclohexyl)-1'-methylvinyl]-23,25-dimethoxy-13,19,21,27-tetramethyl-11,28-dioxa-4-4-azatricyclo[22.3.1.0$^{4,9}$]octacos-18-ene-2,3,10,16-tetraone Step A: 17-Ethyl-1-hydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3'',4'-'-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (792 mg in 18 ml 33% methylene chloride in cyclohexane) isopropyl trichloroacetimidate (320 μl neat) was added and the reagents allowed to mix for 5 minutes. Trifluoromethanesulfonic acid (75 μl neat) was added slowly via syringe and the mixture stirred at room temperature. After 48 hours the reaction was quenched by the addition of saturated sodium bicarbonate and extracted with ethyl acetate (3×10 ml). The combined organics were washed with brine and dried over magnesium sulfate. Purification of the concentrate by flash chromatography on silica gel (ethyl acetate:hexane (1:1)+1% methanol) gave the title compound (158 mg). 3''-ether:

MASS: (FAB) 810 (M+Li)

Partial $^1$H NMR δ: 4.87(brd J=11 Hz, 1H); 4.58 (brd J=4 Hz, 1H); 4.42 m, 4.33 M (brs, 1H); 2.61 (s, 1H); 1.15(d J=7 Hz, 6H).

Step B: 17-Ethyl-1-hydroxy-12-[2'-(4''-(o-nitrophenylsulfonyloxy)-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (158 mg) in dry methylene chloride (3.5 ml) was added an excess of diisopropylethyl amine (82 μl) and o-nitrophenylsulfonyl chloride (87 mg) followed by addition of 4-dimethylaminopyridine (58 mg). The mixture was stirred at room temperature for 23 hours at which time it was diluted with ethyl acetate, extracted from saturated sodium bicarbonate solution and washed with brine. The combined organics were dried over magnesium sulfate and the concentrate purified by flash chromatography on silica gel (ethyl acetate: hexane (1:1)+1% methanol to give the title compound (130 mg).

Partial $^1$H NMR δ: 8.16 (m, 1H); 7.75(m, 3H); 4.88 (brd J=11 Hz, 1H); 4.58 (brd J=4 Hz, 1H); 4.57 (m, 1H); 4.42 m, 4.31M (brs, 1H).

Step C: 17-Ethyl-1-hydroxy-12-[2'-(4''-azido-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-(o-nitrophenylsulfonyloxy)-3''-isopropyloxycyclohexyl)-1'-methylvinyl[-23,25-dimethoxy-13,19,21,27-tetramethyl-11,28-dioxa-4-azatricyclo[22.3.1.0$^{4,9}$]octacos-18-ene-2,3,10,16-tetraone (130 mg) in N,N-dimethyl formamide (2 ml) was added an excess of sodium azide (43 mg) and the mixture heated to 70° C. After 4 hours the reaction was cooled to room temperature, diluted with ethyl acetate, extracted from half-saturated ammonium chloride, and washed with brine. The combined organics were dried over magnesium sulfate and purified by flash chromatography on silica gel (ethyl acetate: hexane (1:2)+1% methanol) to give the title compound (50 mg).

MASS: (FAB) 851 (M+Na)

Partial $^1$H NMR δ: 4.59 (brd J=4 Hz, 1H); 4.47 m, 4.32M(brs, 1H); 4.41 (brd J=14 Hz, 1H).

EXAMPLE 83

17-Ethyl-1-hydroxy-12-[2'-(4''-amino-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-azido-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (50 mg) in 10% aqueous benzene (1.7 ml) was added triphenylphosphine (24 mg) and the mixture heated to 70° C. with stirring. After 17 hours, the stir bar was removed and the reaction cooled to room temperature. The mixture was concentrated to 10% volume in vacuo and applied directly to a column of silica gel for purification by flash chromatography (ethyl acetate: hexane (1:1)+1% methanol then 2% ammonium hydroxide, 5% methanol in methylene chloride) to give the title compound (38 mg).

MASS: (FAB) 802 (M$^+$).

Partial $^1$H NMR δ: 4.58 (brd J=4 Hz, 1H); 4.41 (brd J=4 Hz, 1H); 3.87(dd J=12, 3 Hz, 1H).

EXAMPLE 84

17-Ethyl-1-hydroxy-12-[2'-(4''-azido-3''-propyloxcyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A: 17-ethyl-1-hydroxy-12-[2'-(4''-hydroxy-3''-propyloxycyclohexyl)-1'-methylvinyl[23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-hydroxy-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (45.5 mg in 0.75 ml ethyl acetate) (Example 86) was added 6 mg of 5% rhodium on carbon catalyst. The reaction flask was fitted with a hydrogen balloon, evacuated and recharged with hydrogen (3 times) and stirred at room temperature. After 30 minutes, the mixture was filtered over Celite, concentrated and purified by flash chromatography on silica gel (ethyl acetate: hexane (1:1)+1% methanol) to give the title compound (40 mg).

Partial $^1$H NMR δ: 4.87 (brd J=11 Hz, 1H); 4.58 (brd J=4 Hz, 1H); 4.44 m, 4.34M(brs, 1H); 4.41 (brd J=14 Hz, 1H); 3.07 (m, 1H); 2.69(s, 1H).

Step B: 17-Ethyl-1-hydroxy-12-[2'-(4''-(o-nitrophenylsulfonyloxy)-3''-propyloxycyclohexyl)-1'- methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-hydroxy-3''-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (130 mg) in dry methylene chloride (1.75 ml) was added an excess of diisopropylethyl amine (67 μl) and o-nitrophenylsulfonyl chloride (72 mg) followed by addition of 4-dimethylaminopyridine (47 mg). The mixture was stirred at room temperature for 16 hours at which time it was diluted with ethyl acetate, extracted from half-saturated sodium bicarbonate solution and washed with brine. The combined organics were dried over magnesium sulfate and the concentrate purified by flash chromatography on silica gel (ethyl acetate: hexane (1:2)+1% methanol to give the title compound (111 mg).

Partial $^1$H NMR δ: 8.18 (m, 1H); 7.73(m, 3H); 4.88 (brd J=11 Hz, 1H); 4.59(m, 1H); 4.58 (brd J=4 Hz, 1H); 4.44 m, 4.34M (brs, 1H)

Step C: 17-Ethyl-1-hydroxy-12-[2'-(4''-azido-3''-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-(o-nitrophenylsulfonyloxy)-3''-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (111 mg) in N,N-dimethyl formamide (1.1 ml) was added an excess of sodium azide (32 mg) and the mixture heated to 70° C. After 5.5 hours the reaction was cooled to room temperature, diluted with ethyl acetate, extracted from half-saturated ammonium chloride, and washed with brine. The combined organics were dried over sodium sulfate and purified by flash chromatography on silica gel (ethyl acetate: hexane (1:2)+1% methanol) to give the title compound (52 mg).

Partial $^1$H NMR δ: 4.59 (brd J=4 Hz, 1H); 4.47 m, 4.35M (brs, 1H); 4.41(brd J=14 Hz, 1H); 4.04 (brs, 1H).

EXAMPLE 85

17-Ethyl-1-hydroxy-12-[2'-(4''-amino-3''-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-azido-3''-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (46 mg) in 10% aqueous benzene (900 μl) was added triphenylphosphine (29 mg) and the mixture heated to 70° C. with stirring. After 6.5 hours, the stir bar was removed and the reaction cooled to room temperature. The mixture was concentrated to 10% volume in vacuo and applied directly to a column of silica gel for purification by flash chromatography (ethyl acetate: hexane (1:1)+1% methanol then 2% ammonium hydroxide, 5% methanol in methylene chloride) to give the title compound (37 mg).

MASS: (FAB) 803 (M+).

Partial $^1$H NMR: 4.56 (brd J=4 Hz, 1H); 4.41(brd J=14 Hz, 1H); 3.87(dd J=9, 3 Hz, 1H); 3.68 (brd J=10 Hz, 1H).

EXAMPLE 86

17-Ethyl-1-hydroxy-12-[2'-(4''-hydroxy-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A: 17-Ethyl-1-hydroxy-12-[2'-(4''-(tert-butyldimethylsiloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (1.04 g) in dry methylene chloride (25 ml) was added an excess of imidazole (280 mg) followed by tert-butyldimethylsilyl chloride (228 mg). After 21 hours of stirring at room temperature, the mixture was quenched by the addition of half-saturated sodium bicarbonate and extracted with ethyl acetate. The combined organics were washed with brine, dried over magnesium sulfate and purified by flash chromatography (ethyl acetate: hexane (1:2)+1% methanol) to give the title compound (370 mg).

Partial $^1$H NMR δ: 4.58 (brd J=4 Hz, 1H); 4.42 m, 4.31M (brs, 1H); 4.41 (brd J=14 Hz, 1H); 2.43(s, 1H); 0.88(s, 9H); 0.09(s, 3H); 0.07 (s, 3H).

Step B: 17-Ethyl-1-hydroxy-12-[2'-(4''-(tert-butyldimethylsiloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''(tert-butyldimethylsiloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (186 mg in 6 ml 33% methylene chloride in cyclohexane) allyltrichloroacetimidate (62 μl neat) was added and the reagents allowed to mix for 5 minutes. Trifluoromethanesulfonic acid (5 μl neat) was added slowly via syringe and the mixture stirred at room temperature. After 24 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate: hexane (1:4)+1% methanol) gave the title compound (80 mg).

Partial $^1$H NMR δ: 5.90 (m, 1H); 4.57(brd J=4 Hz, 1H); 4.42 m, 4.33M (brs, 1H); 4.41(brd, J=14 Hz, 1H); 4.09(m, 2H).

Step C: 17-Ethyl-1-hydroxy-12-[2'-(4''-hydroxy-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-(tert-butyldimethylsiloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (80 mg) in acetonitrile (5 ml) was added a solution of 2% HF in aqueous acetonitrile (100 μl), and the mixture stirred at room temperature. After 24 hours, the solution was diluted with ethyl acetate, extracted with saturated sodium bicarbonate solution and the organic phase dried over magnesium sulfate.

Purification of the concentrate by flash chromatography on silica gel (ethyl acetate: hexane (1:1)+1% methanol) gave the title compound (66 mg).

Partial $^1$H NMR $\delta$: 5.90 (m, 1H); 4.87 (d J=11 Hz, 1H); 4.57 (brd J=4 Hz, 1H); 4.45 m, 4.33M (brs, 1H); 4.41 (brd, J=14 Hz, 1H); 2.65 (s, 1H).

EXAMPLE 87

17-Ethyl-1-hydroxy-12-[2'-(4''-acetylamino-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,20,26-tetraone To a solution of 17-ethyl-1-hydroxy-12-[2'-(4'-amino-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (30 mg) in dry methylene chloride (0.2 ml) is added triethylamine (10 $\mu$l) followed by a solution of acetic anhydride in methylene chloride (10 mg in 1 ml) at r.t. Reaction is stirred for 30 minutes and the solvent was removed under nitrogen flow. The crude product is purified by preparative tlc on silica gel to give of the title compound.

EXAMPLE 88

17-Ethyl-1-hydroxy-12-[2'-(4''-N-(2-propenyl)amino-3''-isopropyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone The compound 17-ethyl-1-hydroxy-12-[2'-(4'-amino-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone(30 mg) is placed in a dry flask equipped with stir bar and condenser. Dry toluene (1 ml) is added followed by diisopropylethylamine (13 mg) and freshly distilled allyl bromide (40.5 mg) at 0° C. with stirring. Reaction temperature is raised to 70° C. gradually and stirred for 2 hr. The reaction mixture is cooled, and the solvent is removed under nitrogen flow. The residue is purified by preparative tlc on silica gel to give the title compound.

EXAMPLE 89

17-Ethyl-1-hydroxy-12-[2'-[4''-(D-phenylalanine)amido3''-propyloxycyclohexyl]-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-amino-3''-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (46 mg) in dry methylene chloride (2 ml) is added 102 mg of freshly prepared BOC-D-phenylalanine anhydride (prepared as described in *Solid Peptide Synthesis*, p. 32, J. M. Steward and J. D. Young, Pierce Chemical Company) under nitrogen. Reaction is stirred at room temperature and the process was followed by tlc analysis. After 2.5 hr, the reaction mixture is subjected to work-up and preparative tlc on silica gel. The isolated compound in a small flask under nitrogen is cooled to −15° C. and treated with TFA. After 30 minutes the reaction mixture is cooled to −78° C. and freeze-dried to give the crude product. Purification by preparative TLC (silica gel) gives the title compound.

EXAMPLE 90

17-Ethyl-1-hydroxy-12-[2'-[4''-(L-phenylalanine)amido3''-propyloxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound is prepared by the method of Example 89 utilizing BOC-L-phenylalanine anhydride.

EXAMPLE 91

17-Ethyl-1-hydroxy-12-[2'-(4''-acetoxyacetylamino-3''-ethoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone A solution of 17-ethyl-1-hydroxy-12-[2'-(4''-amino-3'-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg) in dry methylene chloride (0.4 ml) is cooled to 0° C. To this solution is added a solution of acetoxyacetyl chloride (9 mg) in methylene chloride (0.5 ml). The reaction mixture is stirred at 0° C. for 30 minutes, and quenched with a drop of methanol. Purification by preparative tlc on silica gel gives the title compound.

EXAMPLE 92

17-Ethyl-1-hydroxy-12-[2'-(4''-(1''''-adamantane carboxamido)-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-(4''-amino-3'-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (35 mg) in dry methylene chloride (0.4 ml) is cooled to 0° C. To this solution is added triethylamine (10 $\mu$l) followed by a solution of 1-adamantane carbonyl chloride (9 mg) in methylene chloride (0.1 ml). The reaction mixture is stirred at 0° C. for 20 minutes. The reaction is purified by preparative tlc on silica gel.

EXAMPLE 93

17-Ethyl-1-hydroxy-12-[2'-(4''-cyclopropanecarboxamido-3''-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 32 mg of 17-ethyl-1-hydroxy-12-[2'-(4''-amino-3''-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in dry methylene chloride (0.4 ml) is cooled to 0° C. To this solution is added triethylamine (10 $\mu$l) followed by a solution of cyclopropane carbonyl chloride (5 mg) in methylene chloride (0.1 ml). The reaction mixture is stirred at 0° C. for 30 min. The reaction mixture is purified by preparative tlc on silica gel to give the title compound.

EXAMPLE 94

17-Ethyl-1-hydroxy-12-[2-(4''-formamido-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The compound 17-ethyl-1-hydroxy-12-[2'-(4''-amino-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone(30 mg) is mixed with methyl formate (0.5 ml) and is stirred at 0° C. for 1 hr. The reaction mixture is allowed to warm to room temperature and then is stirred overnight. The excess methylformate is removed with nitrogen flow and the crude mixture is purified by preparative tlc on silica gel to give the title compound.

EXAMPLE 95

17-Ethyl-1-hydroxy-12-{2'-[4''',5'''-dicarboethoxy-1-''',2''',3'''-triazole)-3''-ethoxycyclohexyl]-1'-methylvinyl}-23,25-dimethoxy-13,19,21,27-tetramethyl-11,28-dioxa-4-azatricyclo[22.3.1.0$^{4,9}$]octacos-18-ene-2,3,10,16-tetraone A mixture of 17-ethyl-1-hydroxy-12-[2'-(4''-azido-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16tetraone(20 mg) in neat diethylacetylene dicarboxylate (0.1 ml) is stirred at room temperature overnight. The cycloaddition product is isolated by preparative tlc on silica gel to give the title compound.

EXAMPLE 96

17-Ethyl-1-hydroxy-12-[2'-(3''-propyloxy-4''-oxocyclohexyl)-1'-methylvinyl]-14-triisopropylsilyloxy-23,25-dimethoxy-13,19,21,27-tetramethyl-11,28-dioxa-4-azatricyclo[22.3.1.0$^{4,9}$]octacos-18-ene-2,3,10,16-tetraone To a cooled solution (−78° C.) of oxalyl chloride added dimethyl sulfoxide dropwise, followed by a solution of 17-ethyl-1-hydroxy-12-[2'-(4''-hydroxy-3''-propyloxycyclohexyl)-1'-methylvinyl]-14-triisopropylsiloxy-23,25-dimethoxy-13,19,21,27-tetramethyl-11,28-dioxa-4-azatricyclo[22.3.1.0$^{4,9}$]octacos18-ene-2,3,10,16-tetraone in dry methylene chloride. The reaction mixture is stirred for 30 min. at −78° C. and then triethylamine is added. The reaction temperature is raised to room temperature, reaction was poured into water, and extracted with ethyl acetate (three times). Combined organic layers were washed (water, sat'd NaHCO$_3$), dried (anhydrous Na$_2$SO$_4$), and filtered. Removal of solvent followed by purification (silica gel column chromatography) gives the title compound.

EXAMPLE 97

17-Ethyl-1,14-dihydroxy-12-[2'-(3''-propyloxy-4'-'-oxocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1-hydroxy-12-[2'-(3''-propyloxy-4''-oxocyclohexyl)-1'-methylvinyl]14-triisopropylsilyloxy-23,25-dimethoxy-13,19,21,27-tetramethyl-11,28-dioxa-4-azatricyclo[22.3.1.0$^{4,9}$]octacos-18-ene-2,3,10,16-tetraone from Example 96 in acetonitrile was added hydrofluoric acid at room temperature. The reaction progress is monitored by tlc analysis and then the reaction mixture is quenched with sat'd aqueous sodium bicarbonate. The organic layer is separated and the aqueous layer is extracted with ethyl acetate three times. Combined organic layers are washed (sat'd NaHCO$_3$, sat'd NaCl), dried (anhydrous Na$_2$SO$_4$), and filtered. Removal of solvent followed by purification (silica gel column chromatography) gives the title compound.

EXAMPLE 98

17-Ethyl-1,14-dihydroxy-12-[2'-(4''-benzylamino-3''-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3''-propyloxy-4''-oxocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in dry isopropyl alcohol (3 ml) is added benzyl amine (86.5 mg). The mixture is stirred at r.t. for 30 minutes, and cooled to −78° C. To this solution is added a solution of sodium cyanoborohydride (6.7 mg) in isopropyl alcohol (0.5 ml). The reaction is stirred at −78° C. and poured into ice water. Extraction with ethyl acetate, followed by purification gives the title compound as a mixture of epimers at C-4''.

EXAMPLE 99

17-Ethyl-1-hydroxy-12-[2'-(4''-trimethylamino-3''-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Iodide 17-Ethyl-1-hydroxy-12-[2'-(4''-amino-3''-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone is dissolved in absolute ethanol in a heavy walled glass tube. Methyl iodide (large excess) and NaHCO$_3$ is added, the tube is sealed, and the tube is heated. Progress of the reaction is followed by watching dissappearance of the starting amine on thin layer chromatography and the appearance of a more polar new spot. Upon completion of reaction, the quarternary iodide is obtained by evaporation of excess methyl iodide and solvent.

EXAMPLE 100

17-Ethyl-1,2,14-trihydroxy-12-[2'-(4''-acetylamino-3''-propyloxycyclohexyl)-1'-methylvinyl]-23,25-dimethoxy-13,1927-tetramethyl-11,28-dioxa-4-azatricyclo[22.3.1.0$^{4,9}$]octacos-18-ene-3,10,16-trione To a suspension of samarium (63 mg) in dry THF (1 ml) is added a solution of diiodoethane (56 mg in 1 ml THF) at r.t., and stirred for 1 hr. The dark blue solution is cooled to −78° C., and to this mixture is added a solution of 17-ethyl-1,14-dihydroxy-12-[2'-(4''-a cetylamino-3''-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (166 mg) in 50% THF/MeOH (3 ml). The reaction is stirred for −78° C. for 10 minutes., allowed to warm to room temperature over a period of 10 min., and then quenched with saturated potassium carbonate solution. The organic layer is extracted with ether/ethyl acetate, washed (sat'd NaCl), and dried (anhydrous Na$_2$SO$_4$). Removal of solvent followed by chromatography on silica gel gives the title compound.

EXAMPLE 101

17-Ethyl-1-hydroxy-12-{2'-[4"-(N'-phenylaminocarb onyl)amino-3"-isopropyloxycyclohexy]-1'-methylvinyl}23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4'-amino-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg) in methylene chloride (2 ml) is added phenyl isocynate (12 mg) at 0° C. with stirring. The reaction mixture is warmed to room temperature and the reaction progress is followed by tlc analysis. The reaction mixture is concentrated under a stream of nitrogen and purified by preparative tlc on silica to give the title compound.

EXAMPLE 102

17-Ethyl-1-hydroxy-12-{2'-[4"-(ethoxycarbonyl)amino-3"-propyloxycyclohexyl]-1'-methylvinyl}-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4"-amino-3"-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg) in methylene chloride (2 ml) is added triethylamine (10 µl), followed by ethyl chloroformate (15 µl) at 0° C. with stirring. The reaction mixture is warmed to room temperature and the reaction progress is followed by tlc analysis. The solution is quenched with a drop of methanol and purified by preparative tlc on silica to give the title compound.

EXAMPLE 103

17-Ethyl-1-hydroxy-12-[2'-(4"-acetylamino-3"-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-{2'-(4"-amino-3"-propyloxycyclohexyl)-1'-methylvinyl]-23,25-dimethoxy-13,19,21,27-azatricyclo[22.3.1.0$^{4,9}$]octacos-18-ene-2,3,10,16-tetraone (60 mg) in dry CH$_2$Cl$_2$ (0.5 ml) is added Et$_3$N (20 µl) followed by a solution of acetic anhydride (20 mg in 1 ml). Work-up and purification on silica gel affords the title compound.

EXAMPLE 104

17-Ethyl-1-hydroxy-12-[2'-(4"-morpholino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 100 mg of 17-ethyl-1-hydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in 5 ml of dichloromethane at 0° C. was treated with 47 mg of 4-dimethylaminopyridine, 0.067 ml of N,N-diisopropylethylamine and 0.043 ml of trifluoromethanesulphonic anhydride and the reaction mixture stirred for 30 minutes. The reaction mixture was poured into saturated sodium chloride solution and extracted with ethyl acetate. The combined organic layers were dried with anhydrous magnesium sulphate and concentrated. The residue was purified by flash chromatography on silica gel eluting with 70% hexane: 30% acetone to give 96 mg of pure product. A solution of morpholine in 0.5 ml of tetrahydrofuran at ambient temperature was treated with 2.3 mg of sodium hydride and stirred for 10 minutes before adding 0.16 ml of this solution to a solution of 22 mg of the pure product above in 0.3 ml of tetrahydrofuran. The resulting mixture was heated to 60° C. for 2 hours and then the cooled reaction mixture was poured into saturated ammonium chloride solution and extracted with ethyl acetate. The combined organic layers were dried with anhydrous magnesium sulphate and concentrated. The residue was purified by flash chromatography on silica gel eluting with 70% hexane: 30% acetone to give 8.4 mg and 4.1 mg of two isomers of the title compound.

EXAMPLE 105

17-Ethyl-1-hydroxy-12-[2'-(4"-N-(3-(4-hydroxyphenyl)propenyl)amino-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 100 mg of 17-ethyl-1-hydroxy-12-[2'-[4"'-amino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (30 mg) in dry toluene/DMF (9:1, 2 ml) was added freshly prepared 3-(4-(tert-butyldimethylsiloxy)-phenyl)propenyl chloride (3 fold excess) followed by diisopropylethylamine (30 µl). After 16 hours of stirring at 80° C., the solvent was removed in vacuo and the residue was purified by preparative tlc on silica gel (50% ethyl acetate/hexane) to give 12 mg of the hydroxy protected compound. The material was dissolved in 5% HF (48% solution) in acetonitrile (1 ml) and stirred at room temperature for 1 hour. The reaction was quenched with aqueous saturated sodium bicarbonate solution and extracted with ethyl acetate. The combined organic layers were washed with brine, dried over anhydrous magnesium sulfate and purified by preparative tlc on silica gel (5% MeOH/CH$_2$Cl$_2$) to give the title compound.

Partial $^1$H NMR δ: 7.21 (d J=9.6 Hz, 1H); 6.7 (d J=9.6 Hz, 1H), 6.48 (brd J=17.6 Hz, 1H), 6.4(m, 1H) MASS: (FAB) 913(M+Li).

EXAMPLE 106

17-Ethyl-1-hydroxy-12-{2'-[4"-(2-methyl-3'''-(4-hydroxyphenyl)propenylamino-3"-methoxycyclohexyl)-1'-methylvinyl}-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-[amino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (77 mg) in dry toluene/DMF (9:1, 2 ml) was added a freshly prepared 3-(4-OTBDMS-phenyl)-2-methylpropenyl chloride (3 fold excess) followed by diisopropylethylamine (150 µl). After 16 hours of stirring at 80°, the solvent was removed in vacuo and the residue was purified by preparative tlc on silica gel (50% ethyl acetate/hexane) to give 18 mg of the hydroxy protected compound. This material was solvated in 5% HF (48% solution) in acetonitrile (1 ml) and stirred at room temperature for 1 hour. The reaction was quenched with aqueous saturated sodium bicarbonate solution and extracted with ethyl acetate. The combined organic layers were washed with brine, dried over anhydrous magnesium sulfate and purified by preparative tlc on silica gel (5% MeOH/CH$_2$Cl$_2$) to give the title compound (8 mg).

EXAMPLE 107

17-Ethyl-1,14-dihydroxy-12-[2'-[4''-(aminoacetyl)amino3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4'''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in (100 mg) in dry methylene chloride (4 ml) was added 100 mg of freshly prepared BOC-L-glycine anhydride under nitrogen. After stirring at room temperature for 1.5 hours, the reaction mixture was subjected to work-up and the residue was purified on silica gel (5% MeOH/CH$_2$Cl$_2$) to give the 65 mg of BOC protected compound. This material (48 mg) was dissolved in 1 ml of trifluoroacetic acid at $-10°$ and stirred at this temperature. After 30 minutes, the reaction mixture was cooled to $-78°$ and freeze-dried to give the yellow solid. Purification of the crude material by preparative tlc on silica gel (1% NH$_4$OH in 5% MeOH/CH$_2$Cl$_2$) gave 28 mg of the title compound.

MASS: (FAB) 848 (M+H).

EXAMPLE 108

17-Ethyl-1-hydroxy-12-[2'-(4''-(L-Trpamido)-3''-methoxycyclohexyl)-1'-methylvinyl}-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4'''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg) in dry methylene chloride (3 ml) was added 59 mg of freshly prepared BOC-L-tryptophan anhydride under nitrogen. After stirring at room temperature for 30 minutes, the reaction mixture was subjected to work-up and the residue was purified on silica gel (5% MeOH/CH$_2$Cl$_2$) to give 50 mg of BOC protected compound. This material (50 mg) was dissolved in 1 ml of trifluoroacetic acid at $-10°$ C. and stirred at this temperature. After 30 minutes, the reaction mixture was cooled to $-78°$ and freeze-dried to give the yellow solid. Purification of the crude material by preparative tlc on silica gel (5% MeOH/CH$_2$Cl$_2$) gave 32 mg of the title compound.

MASS: (FAB) 968 (M+Li).

Essentially employing the procedures described in the preceeding examples, there are prepared the compounds of Formula I (wherein R$^4$ is hydrogen, R is ethyl, X is O, and n is 2) listed in Table I.

TABLE I

| Example | R$^1$ | R$^2$ | R$^3$ |
|---------|-------|-------|-------|
| 109 | isopropyl | NH$_2$ | OH |
| 110 | isopropyl | NH$_2$ | H |
| 111 | n-propyl | NH$_2$ | OH |
| 112 | n-propyl | NH$_2$ | H |
| 113 | isobutyl | NH$_2$ | OH |
| 114 | isobutyl | NH$_2$ | H |

EXAMPLE 115

T-Cell Proliferation Assay

1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at 2.5×10$^5$ cells/ml in complete culture medium composed of RPMI 1640 medium with 10% heat-inactivated fetal calf serum, 100 mM glutamine, 1 mM sodium pyruvate, 2×10$^{-5}$M 2-mercaptoethanol and 50 µg/ml gentamycin. Ionomycin was added at 250 ng/ml and PMA at 10 ng/ml. The cell suspension was immediately distributed into 96 well flat-bottom microculture plates (Costar) at 200 µl/well. The various dilutions of the compound to be tested were then added in triplicate wells at 20 ul/well. The compound 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 µCi/well of tritiated thymidine (NEN, Cambridge, Mass.) After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results expressed as concentration of compound required to inhibit tritiated thymidine uptake of T-cells by 50%.

A selection of compounds were tested according to the previous procedure. The title compounds of the following Examples had activity in inhibiting the proliferation of T-cells in the aforementioned assay:
1, 3, 4, 5, 10, 11, 12, 13, 17, 21, 29, 30, 33, 34, 35, 36, 37, 51, 54, 58, 59, 60, 62, 71, 72, 81, and 83.

The results of this assay are representative of the intrinsic immunosuppressive activity of the compounds of the present invention.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of formula I:

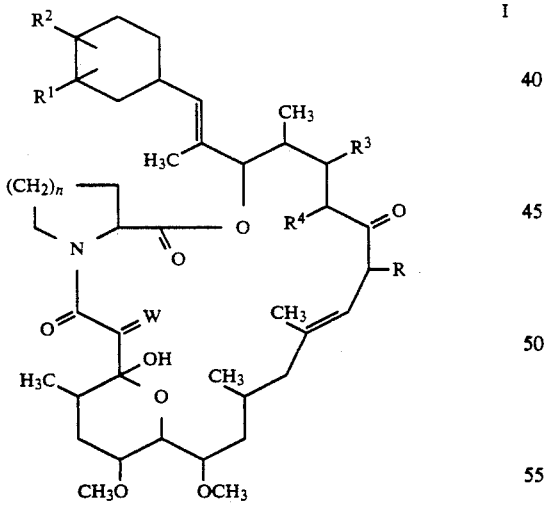

I or a pharmaceutically acceptable salt thereof, wherein:
R is
  1) methyl,
  2) ethyl,
  3) propyl, or
  4) allyl;
$R^1$ and $R^2$ are, independently,
  1) $-N_3$;
  2) $-NHCN$;
  3) $-NR^5R^6$, wherein $R^5$ and $R^6$ are independently,
    a) hydrogen,
    b) $C_1$-$C_{12}$ alkyl, unsubstituted or substituted with $R^7$ and $R^8$, wherein $R^7$ and $R^8$ are independently selected from the group consisting of:
      i) hydrogen,
      ii) $-OH$,
      iii) $C_1$-$C_6$alkoxy,
      iv) $-O-CO-C_1$-$C_6$alkyl,
      v) $-NR^9R^{10}$, wherein $R^9$ and $R^{10}$ are independently, hydrogen, or $C_1$-$C_6$alkyl, unsubstituted or substituted with phenyl
      vi) $-CONR^9R^{10}$,
      vii) $-CO_2H$,
      viii) $-CO-O-C_1$-$C_6$alkyl,
      ix) $-S-C_1$-$C_6$alkyl,
      x) $-SO-C_1$-$C_6$alkyl,
      xi) $-SO_2-C_1$-$C_6$alkyl,
      xii) halo,
      xiii) $-C_3$-$C_7$-cycloalkyl,
      xiv) phenyl, unsubstituted or substituted with M, W and Y, wherein M, W and Y are independently selected from the group consisting of:
        A) hydrogen,
        B) $C_1$-$C_6$alkyl,
        C) $-OH$,
        D) $C_1$-$C_6$alkoxy,
        E) $-O-CO-C_1$-$C_6$alkyl,
        F) $-NR^9R^{10}$, wherein $R^9$ and $R^{10}$ are as defined above,
        G) $-CONR^9R^{10}$,
        H) $-CO_2H$,
        I) $-CO-O-C_1$-$C_6$alkyl,
        J) halo,
        K) $-NO_2$,
        L) $-CN$, and
        N) $-CF_3$,
      xv) naphthyl, unsubstituted or substituted with M, W and Y, wherein M, W and Y are as defined above, and
      xvi) $-CF_3$,
    c) $C_3$-$C_{12}$ alkenyl, unsubstituted or substituted with $R^7$ and $R^8$, wherein $R^7$ and $R^8$ are as defined above,
    d) $C_3$-$C_7$ cycloalkyl, unsubstituted or substituted with $R^7$ and $R^8$, wherein $R^7$ and $R^8$ are as defined above,
    e) phenyl, unsubstituted or substituted with M, W and Y, wherein M, W and Y are as defined above,
    f) naphthyl, unsubstituted or substituted with M, W and Y, wherein M, W and Y are as defined above,
    g) $-SO_2$-phenyl, wherein phenyl is unsubstituted or substituted with with M, W and Y, wherein M, W and Y are as defined above,
    h) $-SO_2-C_1$-$C_6$alkyl,
    i) or where $R^5$ and $R^6$ and the N to which they are attached may form an unsubstituted or substituted 3- to 7-membered heterocyclic ring which may include one or two additional heteroatoms independently selected from the group consisting of O, S, or $NR^9$, wherein $R^9$ is as defined above, and where the substituent(s), attached to the carbon atom(s) in the heterocyclic ring is/are independently selected form the group consisting of:
      i) hydrogen,
      ii) $-OH$,
      iii) $C_1$-$C_6$ alkoxy, iv) —O—CO—C$_1$-C$_6$ alkyl,
v) —NR$^9$R$^{10}$, wherein R$^9$ and R$^{10}$ are independently, hydrogen, or C$_1$-C$_6$alkyl, unsubstituted or substituted with phenyl,
vi) —CONR$^9$R$^{10}$,
vii) —CO$_2$H,
viii) —CO—O—C$_1$-C$_6$ alkyl,
ix) —SH,
x) halo,
xi) phenyl, unsubstituted or substituted with M, W and Y, wherein M, W and Y are as defined above,
xii) naphthyl, unsubstituted or substituted with M, W and Y, wherein M, W and Y are as defined above, and
xiii) —CF$_3$;
4) —N(R$^5$)CO—O—R$^{11}$, wherein R$^5$ is as defined above and R$^{11}$ is C$_1$-C$_{12}$ alkyl, unsubstituted or substituted with R$^7$ and R$^8$, wherein R$^7$ and R$^8$ are as defined above;
5) —N(R$^5$)CO—R$^{12}$, wherein R$^5$ is as defined above and R$^{12}$ is
  a) hydrogen,
  b) C$_1$-C$_{12}$ alkyl, unsubstituted or substituted with R$^7$ and R$^8$, wherein R$^7$ and R$^8$ are as defined above,
  c) C$_3$-C$_{12}$ cycloalkyl, unsubstituted or substituted with R$^7$ and R$^8$, wherein R$^7$ and R$^8$ are as defined above,
  d) phenyl, unsubstituted or substituted with M, W and Y, wherein M, W and Y are as defined above,
  e) naphthyl, unsubstituted or substituted with M, W and Y, wherein M, W and Y are as defined above, or
  f) where R$^5$ and R$^{12}$ and the —NCO— to which they are attached may form an unsubstituted or substituted 5- to 7-membered heterocyclic ring which may include one or two additional heteroatoms independently selected from the group consisting of O, S, or NR$^9$, wherein R$^9$ is as defined above;
6) —N(R$^{13}$)COCH(R$^{17}$)NR$^5$R$^6$ wherein R$^5$ and R$^6$ are as defined above, R$^{13}$ is selected from the definitions of R$^5$, and R$^{17}$ is:
  a) hydrogen,
  b) C$_1$-C$_4$ alkyl, unsubstituted or substituted with R$^{18}$, wherein R$^{18}$ is selected from the group consisting of:
    i) —OH,
    ii) C$_1$-C$_6$alkoxy,
    iii) —O—CO—C$_1$-C$_6$alkyl,
    iv) —SH,
    v) —S—C$_1$-C$_6$alkyl,
    vi) —NR$^9$R$^{10}$, wherein R$^9$ and R$^{10}$ are as defined above,
    vii) —CO$_2$H,
    viii) —CONH$_2$,
    ix) imidazolyl,
    x) indolyl,
    xi) phenyl, and
    xii) p-hydroxyphenyl, or
  c) phenyl;
7) —N(R$^{13}$)CO(CH$_2$)$_m$NR$^5$R$^6$, wherein m is 0 or 2-6, R$^5$ and R$^6$ are as defined above, and R$^{13}$ is selected from the definitions of R$^5$, or where R$^{13}$ and R$^5$ and the —NCO(CH$_2$)$_m$N— to which they are attached may form an unsubstituted or substituted 5- to 7-membered heterocyclic ring;
8) —N=C(R$^{13}$)—NR$^5$R$^6$, wherein R$^5$ and R$^6$ are as defined above, and R$^{13}$ is selected from the definitions of R$^5$, and wherein if either R$^5$ or R$^6$ are hydrogen, the tautomeric structure —NHC(R$^{13}$)=N-R$^{5 or 6}$ is also possible;
9) —N(R$^{14}$)$_3$$^+$A$^-$, wherein R$^{14}$ is C$_1$-C$_6$ alkyl, unsubstituted or substituted with phenyl or naphthyl, and wherein A$^-$ is a counterion;
10)

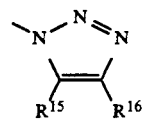

wherein R$^{15}$ and R$^{16}$ are independently,
  a) hydrogen,
  b) phenyl, unsubstituted or substituted with M, W and Y, wherein M, W and Y are as defined above,
  c) naphthyl, unsubstituted or substituted with M, W and Y, wherein M, W and Y are as defined above,
  d) —CN,
  e) —CF$_3$,
  f) —CO—C$_1$-C$_6$alkyl, or
  g) —CO—O—C$_1$-C$_6$alkyl;
11) hydroxy or C$_1$-C$_6$ alkoxy, with the proviso that R$^1$ and R$^2$ are not simultaneously hydroxy, C$_1$-C$_6$ alkoxy, or combinations thereof; or
12) where R$^1$ and R$^2$ may both be connected to form a 3- to 7-membered heterocyclic ring of the form:

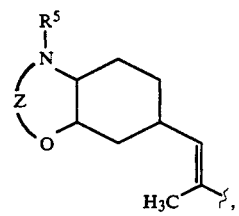

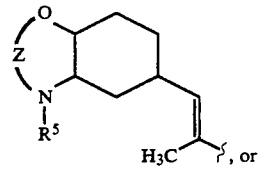

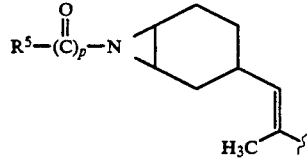

wherein p is zero or one, R$^5$ is as defined above, and Z is
  a) —CO—,
  b) —CS—,
  c) —CO—C$_1$-alkyl,
  d) —CS—C$_1$-alkyl, or e) $C_1$-$C_2$-alkyl, wherein the alkyl may be unsubstituted or substituted with one or more of the following:
  i) —OH,
  ii) $C_1$-$C_6$ alkyl,
  iii) $C_1$-$C_6$ alkoxy,
  iv) —O—CO—$C_1$-$C_6$ alkyl,
  v) —$NR^9R^{10}$, wherein $R^9$ and $R^{10}$ are as defined above,
  vi) —$CONR^9R^{10}$,
  vii) —$CO_2H$,
  viii) —CO—O—$C_1$-$C_6$ alkyl,
  ix) —S—$C_1$-$C_6$ alkyl,
  x) —SO—$C_1$-$C_6$ alkyl,
  xi) —$SO_2$—$C_1$-$C_6$ alkyl,
  xii) halo,
  xiii) phenyl, unsubstituted or substituted with M, W and Y, wherein M, W and Y are as defined above, or
  xiv) naphthyl unsubstituted or substituted with M, W and Y, wherein M, W and Y are as defined above;
$R^3$ is hydrogen, hydroxy, or $C_1$-$C_6$ alkoxyl;
$R^4$ is hydrogen, or $R^3$ and $R^4$ taken together form a double bond;
X is O or (H,OH); and
n is 1 or 2.

2. A compound according to claim 1 wherein the absolute configuration of formula I is as defined in formula III:

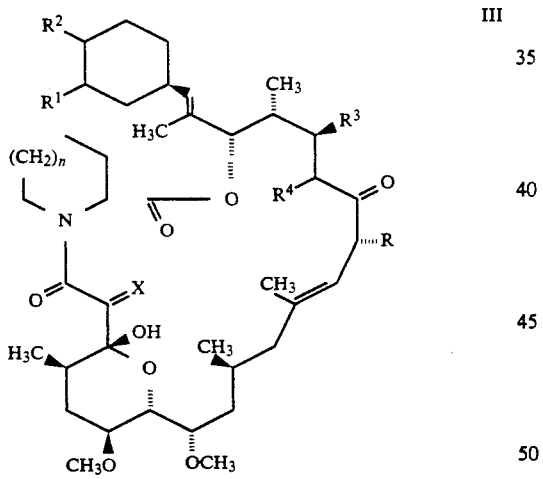

III

3. The compound according to claim 1 wherein:
R is
 1) ethyl,
 2) propyl, or
 3) allyl;
$R^1$ and $R^2$ are, independently,
 1) —$N_3$;
 2) —$NR^5R^6$, wherein $R^5$ and $R^6$ are independently,
  a) hydrogen,
  b) $C_1$-$C_{12}$ alkyl, unsubstituted or substituted with $R^7$ and $R^8$, wherein $R^7$ and $R^8$ are independently selected from the group consisting of:
   i) hydrogen,
   ii) —OH,
   iii) $C_1$-$C_6$alkoxy,
   iv) —O—CO—$C_1$-$C_6$alkyl,
   v) —$NR^9R^{10}$, wherein $R^9$ and $R^{10}$ are independently, hydrogen, or $C_1$-$C_6$alkyl, unsubstituted or substituted with phenyl,
   vi) —$CONR^9R^{10}$,
   vii) —CO—O—$C_1$-$C_6$alkyl,
   viii) halo,
   xiv) phenyl, unsubstituted or substituted with M, W and Y, wherein M, W and Y are independently selected from the group consisting of:
    A) hydrogen,
    B) $C_1$-$C_6$alkyl,
    C) —OH,
    D) $C_1$-$C_6$alkoxy,
    E) —O—CO—$C_1$-$C_6$alkyl,
    F) —$NR^9R^{10}$, wherein $R^9$ and $R^{10}$ are as defined above,
    G) —$CONR^9R^{10}$,
    H) —$CO_2H$,
    I) —CO—O—$C_1$-$C_6$alkyl,
    J) halo,
    K) —$NO_2$,
    L) —CN, and
    N) —$CF_3$,
   xv) naphthyl, unsubstituted or substituted with M, W and Y, wherein M, W and Y are as defined above, and
   xi) —$CF_3$,
  c) $C_3$-$C_{12}$alkenyl, unsubstituted or substituted with $R^7$ and $R^8$, wherein $R^7$ and $R^8$ are as defined above,
  d) $C_3$-$C_7$ cycloalkyl, unsubstituted or substituted with $R^7$ and $R^8$, wherein $R^7$ and $R^8$ are as defined above,
  e) phenyl, unsubstituted or substituted with M, W and Y, wherein M, W and Y are as defined above,
  f) naphthyl, unsubstituted or substituted with M, W and Y, wherein M, W and Y are as defined above,
  g) —$SO_2$-phenyl, wherein phenyl is unsubstituted or substituted with M, W and Y, wherein M, W and Y are as defined above,
  h) —$SO_2$—$C_1$-$C_6$alkyl,
 3) —$N(R^5)CO$—O—$R^{11}$, wherein $R^5$ is as defined above and $R^{11}$ is $C_1$-$C_{12}$ alkyl, unsubstituted or substituted with $R^7$ and $R^8$, wherein $R^7$ and $R^8$ are as defined above;
 4) —$N(R^5)CO$—$R^{12}$, wherein $R^5$ is as defined above and $R^{12}$ is
  a) hydrogen,
  b) $C_1$-$C_{12}$ alkyl, unsubstituted or substituted with $R^7$ and $R^8$, wherein $R^7$ and $R^8$ are as defined above,
  c) $C_3$-$C_{12}$ cycloalkyl, unsubstituted or substituted with $R^7$ and $R^8$, wherein $R^7$ and $R^8$ are as defined above,
  d) phenyl, unsubstituted or substituted with M, W and Y, wherein M, W and Y are as defined above, or
  e) naphthyl, unsubstituted or substituted with M, W and Y, wherein M, W and Y are as defined above;
 5) —$N(R^{13})COCH(R^{17})NR^5R^6$ wherein $R^5$ and $R^6$ are as defined above, $R^{13}$ is selected from the definitions of $R^5$, and $R^{17}$ is:
  a) hydrogen, b) $C_1$-$C_4$ alkyl, unsubstituted or substituted with $R^{18}$, wherein $R^{18}$ is selected from the group consisting of:
 i) —OH,
 ii) $C_1$-$C_6$alkoxy,
 iii) —O—CO—$C_1$-$C_6$alkyl,
 iv) —SH,
 v) —S—$C_1$-$C_6$alkyl,
 vi) —$NR^9R^{10}$, wherein $R^9$ and $R^{10}$ are as defined above,
 vii) —$CO_2H$,
 viii) —$CONH_2$,
 ix) imidazolyl,
 x) indolyl,
 xi) phenyl, and
 xii) p-hydroxyphenyl, or
c) phenyl;
6) —$N(R^{13})CO(CH_2)_mNR^5R^6$, wherein m is 0 or 2–6, $R^5$ and $R^6$ are as defined above, and $R^{13}$ is selected from the definitions of $R^5$;
7) —$N=C(R^{13})$—$NR^5R^6$, wherein $R^5$ and $R^6$ are as defined above, and $R^{13}$ is selected from the definitions of $R^5$, and wherein if either $R^5$ or $R^6$ are hydrogen, the tautomeric structure —$NHC(R^{13})=NR^{5\ or\ 6}$ is also possible;
8) —$N(R^{14})_3{}^+A^-$, wherein $R^{14}$ is $C_1$-$C_6$ alkyl, unsubstituted or substituted with phenyl or naphthyl, and wherein $A^-$ is a counterion;
9) 1-(1,2,3-triazolyl), substituted with $R^{15}$ and $R^{16}$, wherein $R^{15}$ and $R^{16}$ are
 a) hydrogen,
 b) phenyl, or
 c) —CO—O—$C_1$-$C_6$alkyl;
10) hydroxy or $C_1$-$C_6$ alkoxy, with the proviso that $R^1$ and $R^2$ are not simultaneously hydroxy, $C_1$-$C_6$ alkoxy, or combinations thereof; or
11) where $R^1$ and $R^2$ may both be connected to form a 3- to 7-membered heterocyclic ring of the form:

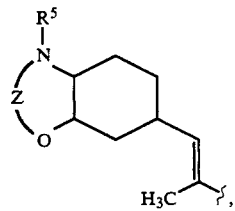

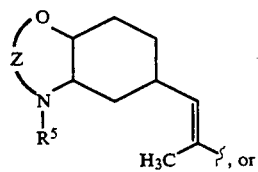

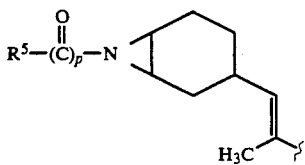

wherein p is one, $R^5$ is as defined above, and Z is
a) —CO—,
b) —CO—$C_1$-alkyl, or
c) $C_1$-$C_2$-alkyl;

$R^3$ is hydrogen or hydroxy;
$R^4$ is hydrogen;
X is O or (H,OH); and
n is 1 or 2;
or a pharmaceutically acceptable salt thereof.

4. A compound of formula I:

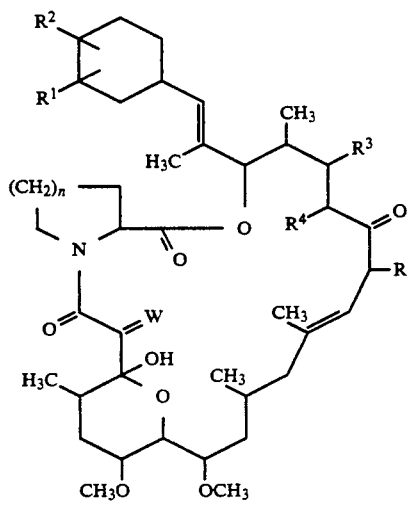

wherein:
R is ethyl, propyl or allyl;
$R^1$ and $R^2$ are, independently, $N_3$—; $H_2N$—; $CH_3NH$—; $(CH_3)_2N$—; $PhCH_2NH$—; $HOCH(CH_3)CH_2NH$—; $CH_2=CHCH_2NH$—; $^+(CH_3)_3N$—; $CH_3CONH$—; $CH_3COOCH_2CONH$—; $PhNHCONH$—; $HCONH$—; $CH_3CH_2OCONH$—; $CH_3OCONH$—; $PhCH_2OCONH$—; $HN=C(CH_3)NH$—; $HN=C(CH_2Ph)NH$—; $HN=CHNH$—; (N'-t-butoxycarbonyl-D-phenylalanine)amido; (N'-t-butoxycarbonyl-L-phenylalanine)amido; (D-phenylalanine)amido; (L-phenylalanine)amido; cyclopropylcarboxamido; adamantylcarboxamido; 1-(4,5-dicarboethoxy-1,2,3-triazole); or hydroxy or $C_1$-$C_6$ alkoxy, with the proviso that $R^1$ and $R^2$ are not simultaneously hydroxy, $C_1$-$C_6$ alkoxy, or combinations thereof;
$R^3$ is hydrogen or hydroxy;
$R^4$ is hydrogen;
X is O; and
n is 2;
or a pharmaceutically acceptable salt thereof.

5. A compound which is selected from:
17-ethyl-1,14-dihydroxy-12-[2'-(4"-azido-3"-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;
17-ethyl-1,14-dihydroxy-12-[2'-(4"-amino-3"-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;
17-ethyl-1,14-dihydroxy-12-[2'-(4"-acetylamino-3"-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;
17-ethyl-1,14-dihydroxy-12-[2'-(4"-N-(2-propenyl)amino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-methylamino-3''-methoxycyclohexyl)-1'-methylvinyl]-23,25-dimethoxy13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(1'''-adamantanecarboxamido)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-cyclopropanecarboxamido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-formamido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-{2'-[4''-(4''',5'''-dicarboethoxy-1''',2''',3'''-triazole)-3''-methoxycyclohexyl]-1'-methylvinyl}-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-acetylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-amino-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-hydroxy-3''-aminocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-amino-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-hydroxy-3''-aminocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-benzylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-benzylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(ethoxycarbonyl)amino-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone;

17-ethyl-1,14-dihydroxy-12-{2'-[4''-(N'-phenylaminocarbonyl)amino-3''-methoxycyclohexyl]-1'-methylvinyl}-23,25-dimethoxy-13,19,21,27-tetramethyl-11,28-dioxa-4-azatricyclo[22.3.1.0$^{4,9}$]-octacos-18-ene-2,3,10,16-tetraone;

17-ethyl-1,14-dihydroxy-12-[2'-(4''-beta-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-alpha-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-beta-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-alpha-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-amino-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-amino-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-amino-3''-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-amino-3''-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-amino-3''-ethoxycyclohexyl)-1'-methylvinyl]-23,25-dimethoxy13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-amino-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-methylcarbamate-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-benzylcarbamate-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-acetamidine-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-benzamidine-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-formamidine-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-allyl-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-allyl-1-hydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(L-phenylalanyl)-amido-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-(L-phenylalanyl)amido-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(D-phenylalanyl)amido-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-(D-phenylalanyl)amido-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(aminoacetylamino)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-(aminoacetylamino)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(2'''-hydroxypropylamino)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-(2'''-hydroxypropylamino)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(1-aza-4-oxabicyclo[4.4.0]dec-6-yl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(1-aza-4-oxabicyclo[4.4.0]dec-6-yl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-trimethylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone iodide;

17-allyl-1,14-dihydroxy-12-[2'-(4''-amino-3''-isopropoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-allyl-1-hydroxy-12-[2'-(4''-amino-3''-isopropoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-propyl-1-hydroxy-12-[2'-(4''-amino-3''-propyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-acetylamino-3''-isopropyloxycyclohexyl)-1'-methylvinyl]-23,25-dimethoxy-13,19,21,27-tetramethyl-11,28-dioxa-4-azatricyclo[22.31.0⁴,⁹]octacos-18-ene-2,3,20,26-tetraone;

17-ethyl-1,14-dihydroxy-12-[2'-[4''-(N'-t-butoxycarbonyl-D-phenylalanine)amido-3''-n-propyloxycyclohexyl]-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-[4''-(N'-t-butoxycarbonyl-L-phenylalanine)amido-3''-n-propyloxycyclohexyl]-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-acetoxyacetylamino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(1'''-adamantanecarboxamido-)3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-cyclopropanecarboxamido-3''-isopropyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2-(4''-formamido-3''-n-propyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-{2'-[4''',5'''-dicarboethoxy-1''',2''',3'''-triazole)-3''-n-propyloxycyclohexyl]-1'-methyl-vinyl}-23,23-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-benzylamino-3''-isopropyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-trimethylamino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone-Iodide;

17-ethyl-1,2,14-trihydroxy-12-[2'-(4''-acetylamino-3''-n-propyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-3,10,16-trione;

17-ethyl-1,14-dihydroxy-12-{2'-[4''-(N'-benzylamino-3''-methoxycyclohexy]-1'-methylvinyl}-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-dihydroxy-12-{2'-[4''-(N'-benzylamino-3''-methoxycyclohexy]-1'-methylvinyl}-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-{2'-[4''-(N'-phenylaminocarbonyl)amino-3''-isopropyloxycyclohexy]-1'-methylvinyl}-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-{2'-[4''-(ethoxycarbonyl)amino-3''-n-propyloxycyclohexyl]-1'-methylvinyl}-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-acetylamino-3''-n-propylcyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-dimethylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-dimethylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-dimethylamino-3''-isopropyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-dimethylamino-3''-n-propylyoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-benzylamino-3''-isopropyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-benzylamino-3''-n-propyloxycyclohexyl)-1'-methylvinyl]-23,25-dimethyoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-(2-phenyl-2-hydroxyethyl)amino-3''-methoxycyclohexyl)-1'-methylvinyl]-23,25-dimethyoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-morpholino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-morpholino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-amino-3''-n-butyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-amino-3''-n-butyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-amino-3''-(3-methylbutyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-amino-3''-(3-methylbutyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-amino-3''-(2-methylbutyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-amino-3''-(2-methylbutyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-(N-(2-methyl-3-(4-hydroxyphenyl)propenyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-(L-Trp)amido-3''-methoxycyclohexyl)-1'-methylvinyl]-23,25-dimethoxy-13,19,21,27-tetramethyl-11,28-dioxa-4-azatricyclo[22.3.1.0⁴,⁹]pctacps-18-ene-2,3,10,16-tetraone;

or a pharmaceutically acceptable salt thereof.

6. The compound of claim 5 which is:

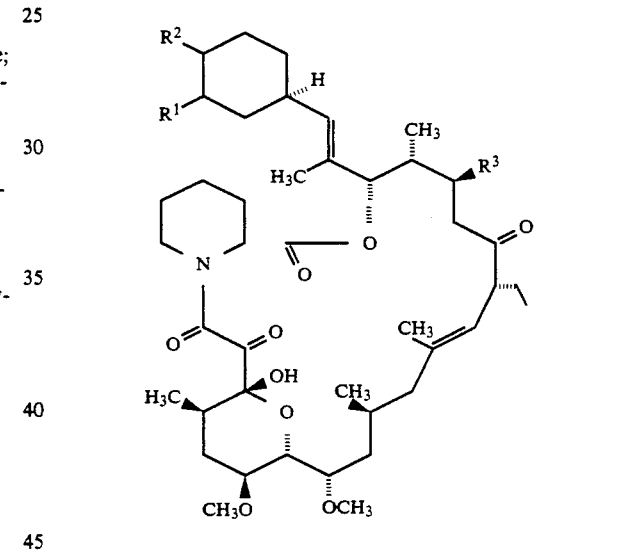

wherein $R^1$, $R^2$ and $R^3$ are selected from:

| $R^1$ | $R^2$ | $R^3$ |
|---|---|---|
| CH₃O▸ | N₃▸ | HO▸ |
| CH₃O▸ | H₂N▸ | HO▸ |
| CH₃O▸ | H₂N▸ | H— |
| CH₃O▸ | H₂N ''' | H— |
| CH₃O▸ | CH₃CONH▸ | H— |
| CH₃O▸ | CH₃NH▸ | H— |
| CH₃O▸ | (CH₃)₂N▸ | H— |
| HO▸ | H₂N▸ | HO▸ |
| HO▸ | H₂N ''' | HO▸ |
| CH₃CH₂O▸ | H₂N▸ | HO▸ |

-continued
| R¹ | R² | R³ |
|---|---|---|
| CH₃CH₂O▶ | H₂N▶ | H— |
| (CH₃)₂CHO▶ | H₂N▶ | HO▶ |
| (CH₃)₂CHO▶ | H₂N▶ | H— |
| CH₃CH₂CH₂O▶ | H₂N▶ | H— |
| CH₃O▶ | PhCH₂NH▶ | H— |
| CH₃O▶ | CH₃CH(OH)CH₂NH▶ | H— |
| CH₃O▶ | morpholino-N▶ | H—. |
7. The compound of claim 5 which is:
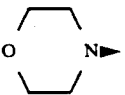
8. The compound of claim 5 which is:
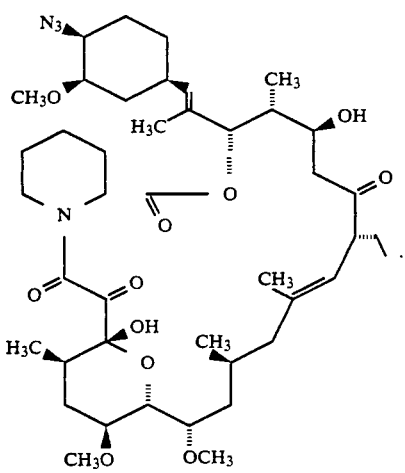
9. The compound of claim 5 which is:
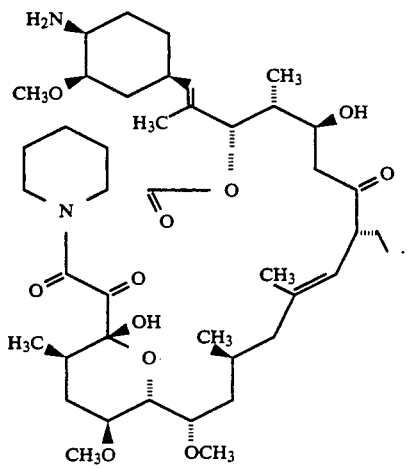
10. The compound of claim 5 which is:
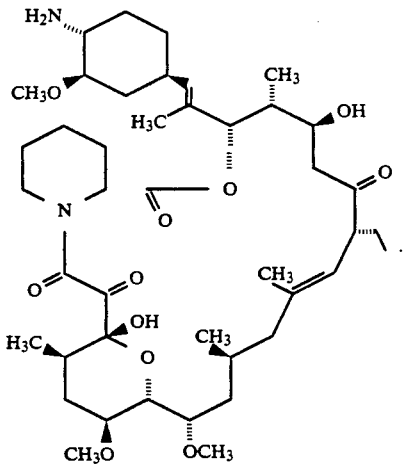
11. The compound of claim 5 which is:
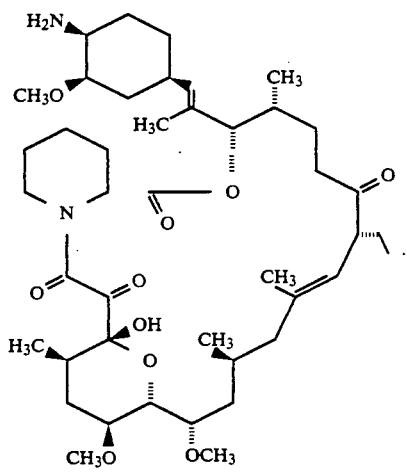
12. The compound of claim 5 which is:
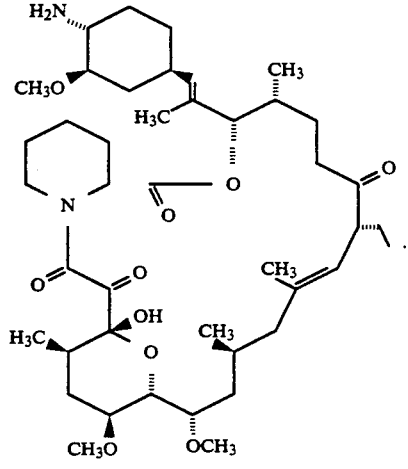

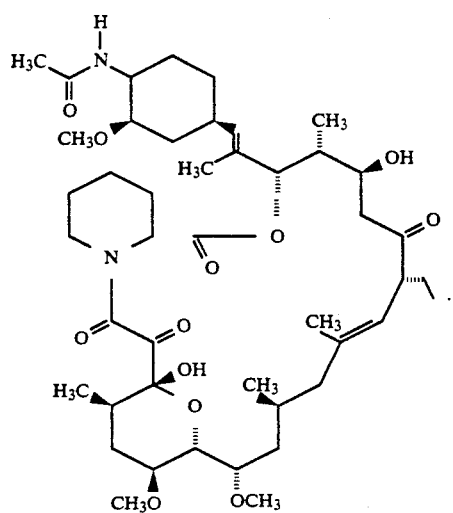
13. The compound of claim 5 which is:
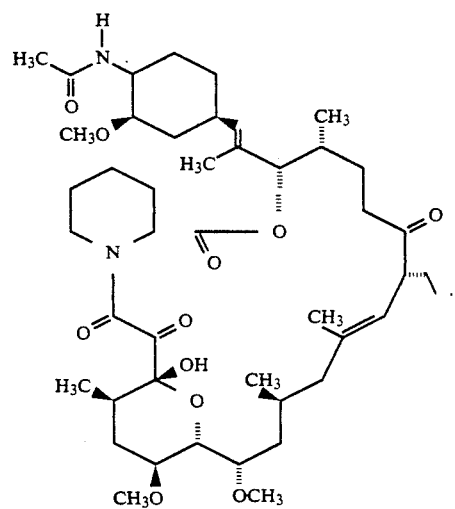
14. The compound of claim 5 which is:
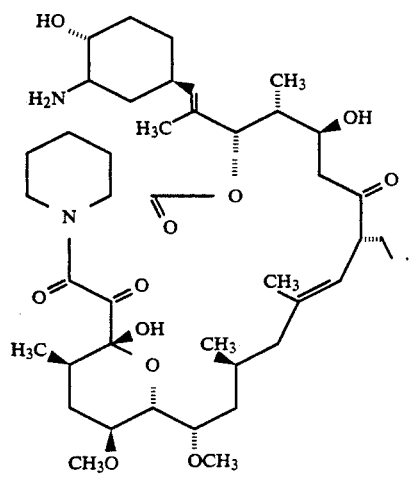
15. The compound of claim 5 which is:
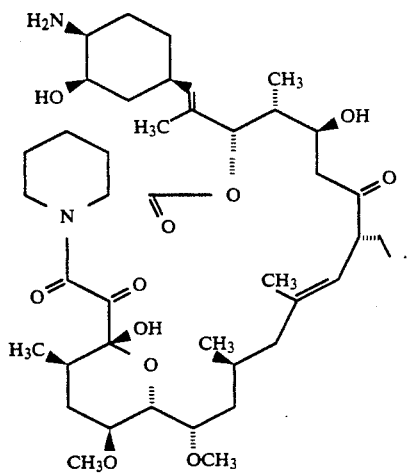
16. The compound of claim 5 which is:
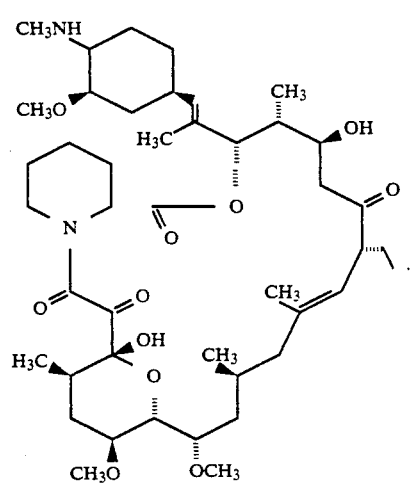
17. The compound of claim 5 which is:
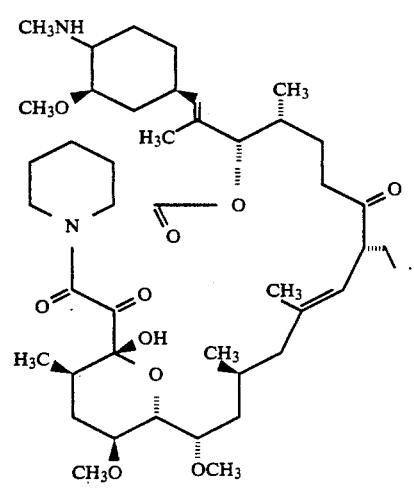
18. The compound of claim 5 which is:

19. The compound of claim 5 which is:

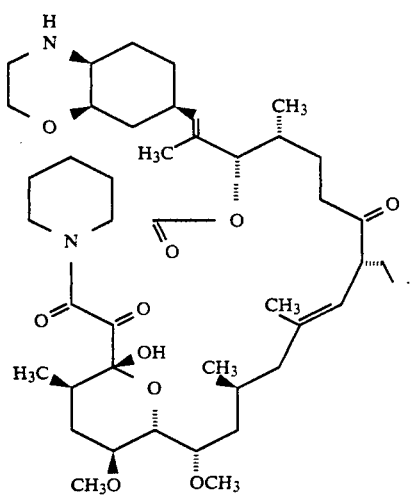

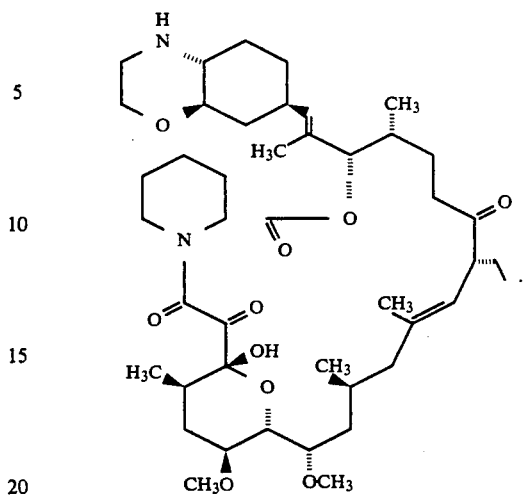

20. A pharmaceutical composition for the treatment of immunoregulatory disorders or diseases comprising a pharmaceutical carrier and a therapeutically effective amount of the compound of claim 1.

21. A pharmaceutical composition for the treatment of resistance to transplantation comprising a pharmaceutical carrier and a therapeutically effective amount of the compound of claim 1.

22. A pharmaceutical composition for the topical treatment of inflammatory and hyperproliferative skin diseases and/or cutaneous manifestations of immunologically-mediated illnesses comprising a pharmaceutical carrier and a therapeutically effective amount of the compound of claim 1.

23. A pharmaceutical composition for the treatment of reversible obstructive airways disease comprising a pharmaceutical carrier and a therapeutically effective amount of the compound of claim 1.

24. A method for the treatment of immunoregulatory disorders or diseases comprising the administration to a mammalian species in need of such treatment an effective amount of the compound of claim 1.

25. A method for the treatment of resistance to transplantation comprising the administration to a mammalian species in need of such treatment an effective amount of the compound of claim 1.

26. A method for the topical treatment of inflammatory and hyperproliferative skin diseases and or cutaneous manifestations of immunologically-mediated illnesses comprising the administration to a mammalian species in need of such treatment an effective amount of the compound of claim 1.

27. A method for the treatment of reversible obstructive airways disease comprising the administration to a mammalian species in need of such treatment of an effective amount of the compound claim 1.

* * * * *